United States Patent
Matula, Jr. et al.

(10) Patent No.: US 8,356,592 B2
(45) Date of Patent: *Jan. 22, 2013

(54) CHIN PIVOT PATIENT INTERFACE DEVICE

(75) Inventors: Jerome Matula, Jr., Apollo, PA (US); Derrick Blake Andrews, Markleton, PA (US); Eugene Nelson Scarberry, Trafford, PA (US); Charles Thomas, Monroeville, PA (US); Erik Kurt Witt, Murrysville, PA (US); Peter Chi Fai Ho, Pittsburgh, PA (US)

(73) Assignee: Ric Investments, LLC, Wilmington, DE (US)

( * ) Notice: Subject to any disclaimer, the term of this patent is extended or adjusted under 35 U.S.C. 154(b) by 55 days.

This patent is subject to a terminal disclaimer.

(21) Appl. No.: 13/011,238

(22) Filed: Jan. 21, 2011

(65) Prior Publication Data

US 2011/0114096 A1    May 19, 2011

Related U.S. Application Data

(63) Continuation of application No. 12/356,948, filed on Jan. 21, 2009, now Pat. No. 7,896,003, which is a continuation of application No. 11/811,126, filed on Jun. 8, 2007, now Pat. No. 7,500,480.

(60) Provisional application No. 60/814,356, filed on Jun. 16, 2006.

(51) Int. Cl.
*A62B 18/08* (2006.01)

(52) U.S. Cl. ......... 128/200.24; 128/206.28; 128/206.29; 128/207.13

(58) Field of Classification Search ............. 128/200.24, 128/200.28, 201.22, 201.23, 203.29, 205.25, 128/206.21, 206.24, 206.27, 206.28, 207.11, 128/207.13, 207.18, 207.17; 2/171.2, 183.9
See application file for complete search history.

(56) References Cited

U.S. PATENT DOCUMENTS

| | | |
|---|---|---|
| 2,241,535 A | 5/1941 | Boothby |
| 4,437,462 A | 3/1984 | Piljay |
| 4,671,271 A | 6/1987 | Bishop |
| 4,677,977 A | 7/1987 | Wilcox |
| 4,782,832 A | 11/1988 | Trimble |
| 4,827,923 A | 5/1989 | Bishop |
| 4,944,310 A | 7/1990 | Sullivan |

(Continued)

FOREIGN PATENT DOCUMENTS

EP    0549299 B1    3/2002

(Continued)

OTHER PUBLICATIONS

Peter C.F. Ho, "Super-Soft Gel Seal and Mask Using Same", U.S. Appl. No. 11/715,760, filed Mar. 8, 2007, pending.

*Primary Examiner* — Steven Douglas
(74) *Attorney, Agent, or Firm* — Michael W. Haas

(57) ABSTRACT

A patient interface device that includes a body portion comprising a pair of arms and a chin support. A first end portion of each arm in the pair of arms is coupled to an opposite end of the chin support. The chin support is adapted to be disposed under the mandible responsive to the patient interface device being donned by a user. At least one headgear attachment element is provided on each arm in the pair of arms. A circuit portion is provided at a second end portion of each arm in the pair of arm. A patient interface portion is coupled to the circuit portion.

18 Claims, 54 Drawing Sheets

U.S. PATENT DOCUMENTS

| | | | |
|---|---|---|---|
| 5,259,373 | A | 11/1993 | Gruenke |
| 5,269,296 | A | 12/1993 | Landis |
| 5,295,480 | A | 3/1994 | Zemo |
| 5,437,273 | A | 8/1995 | Bates |
| 5,560,354 | A | 10/1996 | Berthon-Jones |
| 5,570,689 | A | 11/1996 | Starr |
| 5,647,357 | A | 7/1997 | Barnett |
| 5,687,713 | A | 11/1997 | Bahr |
| 5,724,965 | A | 3/1998 | Handke |
| 5,884,624 | A | 3/1999 | Barnett |
| 5,954,048 | A | 9/1999 | Thornton |
| 6,119,694 | A | 9/2000 | Correa |
| 6,123,082 | A | 9/2000 | Berthon-Jones |
| 6,324,701 | B1 | 12/2001 | Alexander |
| 6,347,631 | B1 | 2/2002 | Hansen |
| 6,397,847 | B1 | 6/2002 | Scarberry |
| 6,431,172 | B1 | 8/2002 | Bordewick |
| 6,470,886 | B1 | 10/2002 | Jestrabek-Hart |
| 6,851,425 | B2 | 2/2005 | Jaffre |
| 6,860,268 | B2 | 3/2005 | Bohn |
| 6,889,689 | B1 | 5/2005 | Neuman |
| 6,895,965 | B2 | 5/2005 | Scarberry |
| 6,926,004 | B2 | 8/2005 | Schumacher |
| 7,000,611 | B2 | 2/2006 | Klemperer |
| 7,047,971 | B2 | 5/2006 | Ho |
| 7,066,179 | B2 | 6/2006 | Eaton |
| 7,069,932 | B2 | 7/2006 | Eaton |
| 2002/0189614 | A1 | 12/2002 | Dominguez |
| 2003/0145859 | A1 | 8/2003 | Bohn |
| 2004/0226566 | A1 | 11/2004 | Gunaratnam |
| 2005/0199242 | A1 | 9/2005 | Matula, Jr. |
| 2005/0205096 | A1 | 9/2005 | Matula, Jr. |
| 2005/0241644 | A1 | 11/2005 | Gunaratnam |
| 2006/0130844 | A1 | 6/2006 | Ho |

FOREIGN PATENT DOCUMENTS

| | | |
|---|---|---|
| WO | WO03027293 | 7/2003 |

CHIN PIVOT PATIENT INTERFACE DEVICE

CROSS-REFERENCE TO RELATED APPLICATIONS

This application is a Continuation under 35 U.S.C. §120 of U.S. patent application Ser. No. 12/356,948, filed Jan. 21, 2009, which is a Continuation under 35 U.S.C. §120 of U.S. patent application Ser. No. 11/811,126, filed Jun. 8, 2007, now U.S. Pat. No. 7,500,480, which claims priority under 35 U.S.C. §119(e) from provisional U.S. patent application No. 60/814,356, filed Jun. 16, 2006, the contents of which are incorporated herein by reference.

BACKGROUND OF THE INVENTION

1. Field of the Invention

The present invention pertains to patient interface device, and, in particular, to a patient interface device is supported, at least in part, under the mandible.

2. Description of the Related Art

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provides a tight enough seal against a patient's face without discomfort. A problem arises in that in order for the mask to maintain a seal without any undue gas leaks around the periphery of the mask, the mask cushion may be compressed against the patient's face. This is most notable, for example, in masks having a bubble type cushion. While the bubble cushion itself is comfortable, it does not provide adequate support, which may cause gas leaks around the periphery of the mask. The bubble effect is diminished when the headgear strap force is increased to improve stability.

Some conventional respiratory masks attempt to enhance mask stability by providing a relatively large structure that must be mounted on the patient's face. Therefore, an advantage exists for a respiratory mask that minimizes the amount of material that must be supported on the patient's head and face, yet provides a relatively high degree of stability, so that that the mask is not easily dislodged from the patient. Another advantage exists for a respiratory mask that evenly distributes the headgear strapping force needed to hold the mask on the patient at locations on the patient's face that are best suited to handle such forces.

A further advantage exists for a respiratory mask that avoids providing any structural features near the patient's eyes. This advantage is particularly important for patient's who desire to where glasses while wearing the mask and for patient's that tend to feel claustrophobic when a structure is provided at or near their eyes. Avoiding the ocular area also eliminates or avoids the leakage of gas into the user's eyes, which can cause great discomfort. A still further advantage exists for a mask that accomplishes these functions while also minimizing the headgear strapping forces needed to pull the mask against the user, so that an effective seal against the user is achieved without undue forces being applied on the user.

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a body portion comprising a pair of arms and a chin support. A first end portion of each arm in the pair of arms is coupled to an opposite end of the chin support. The chin support is adapted to be disposed under the mandible responsive to the patient interface device being donned by a user. At least one headgear attachment element is provided on each arm in the pair of arms. A circuit portion is provided at a second end portion of each arm in the pair of arm. A patient interface portion is coupled to the circuit portion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
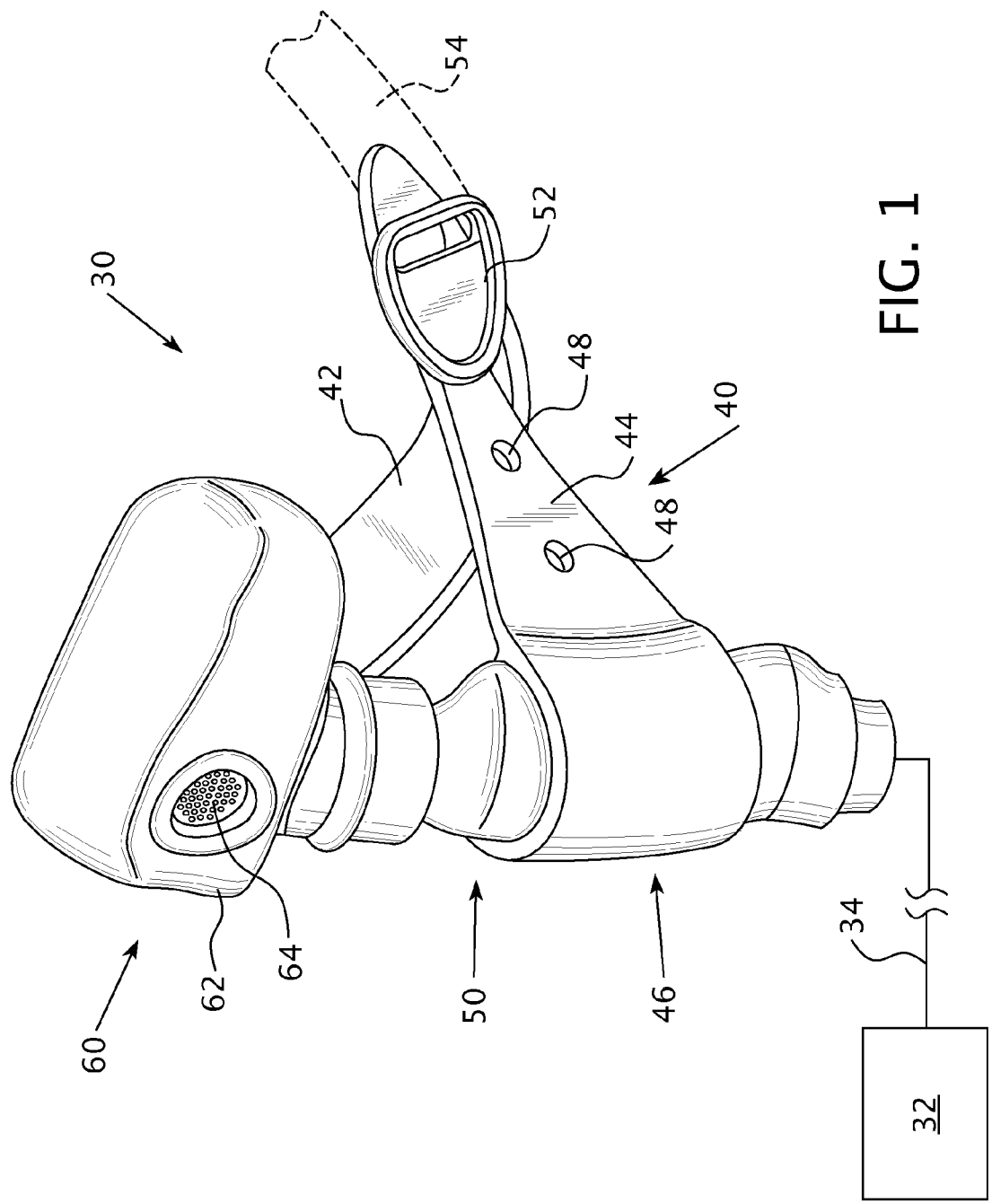
FIG. 1 is a front perspective view of a first embodiment of a patient interface device according to the principles of the present invention.
Figure 2:
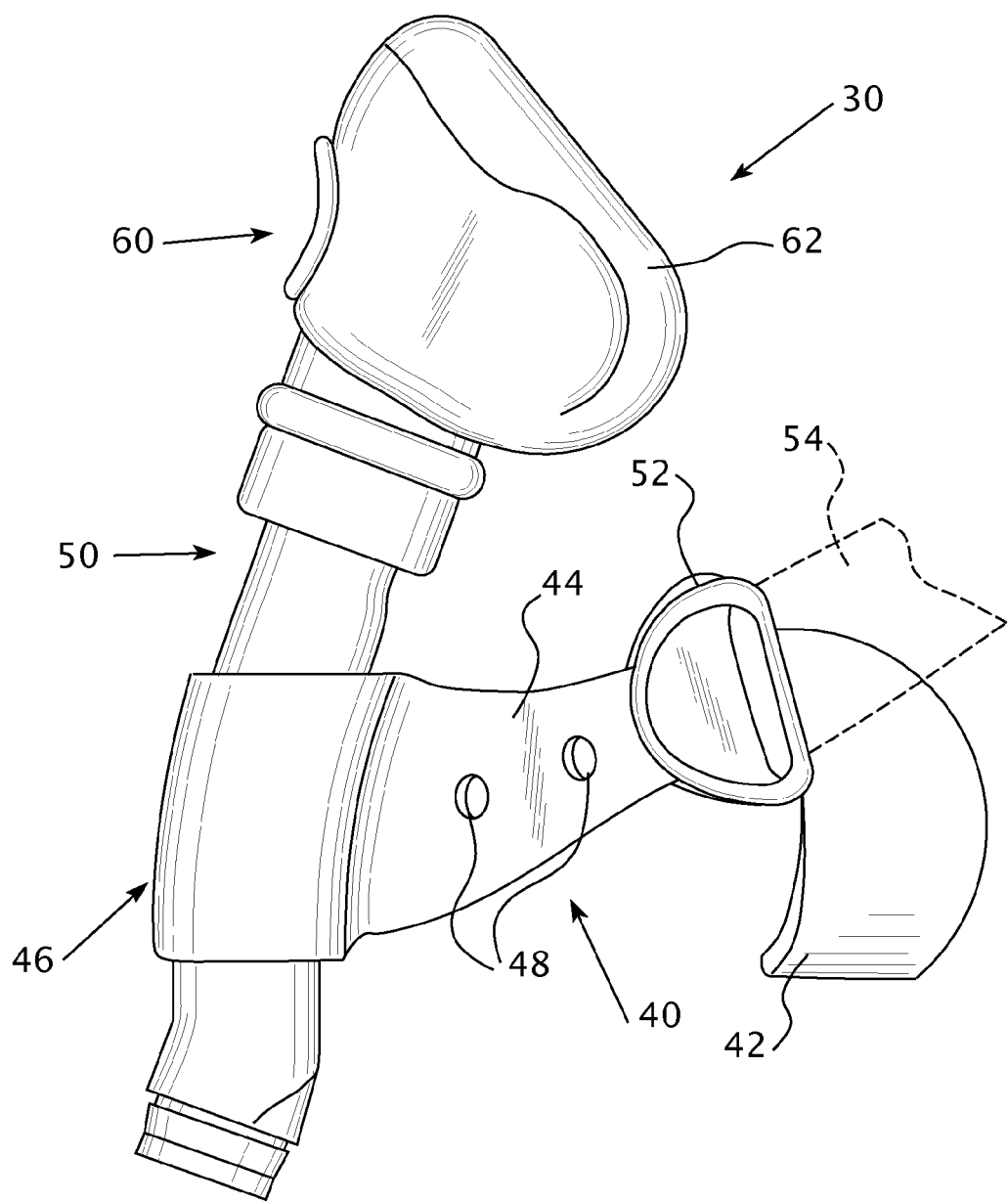
FIGS. 2-4 are a side, front, and exploded views, respectively, of the patient interface device of FIG. 1.
Figure 3:
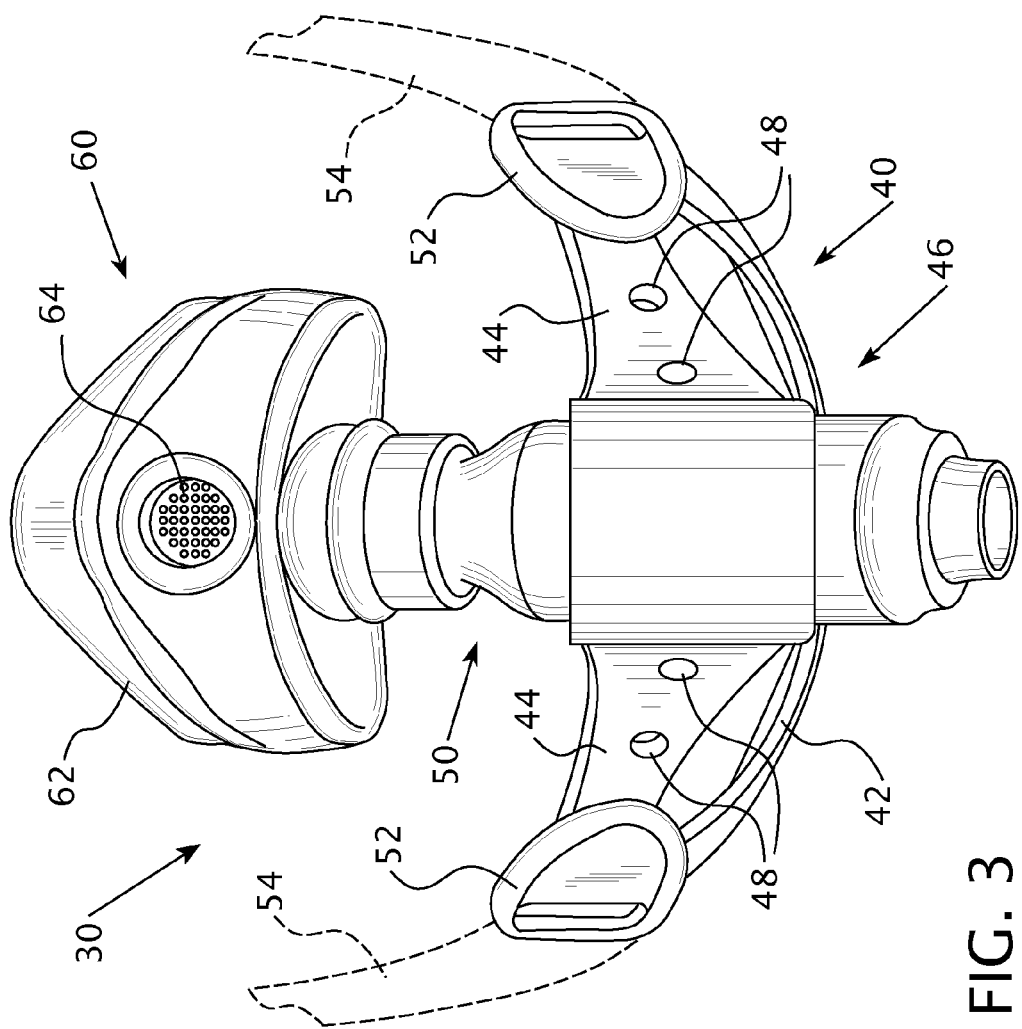
Figure 4:
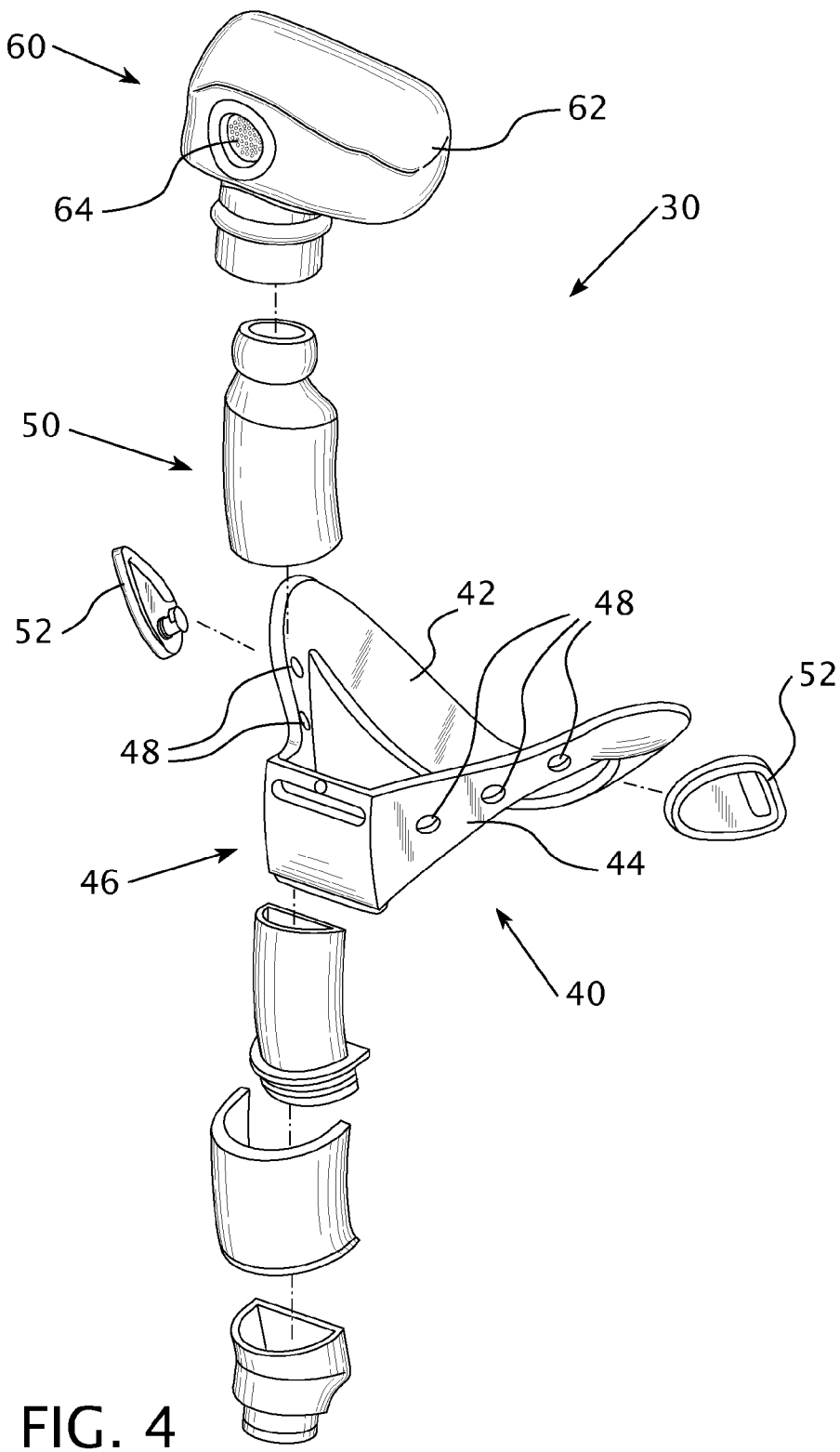
Figure 5:
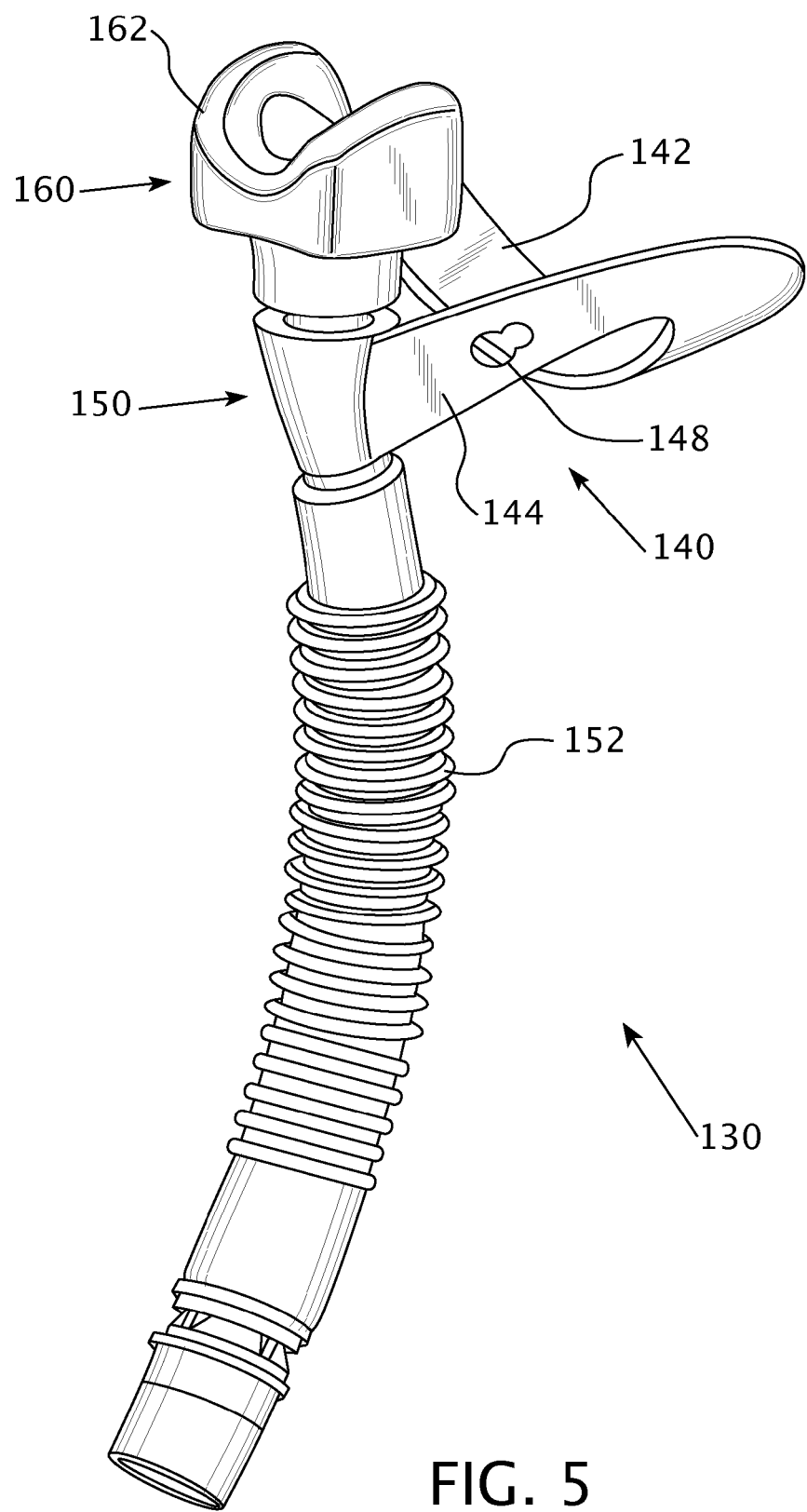
FIG. 5 is a front perspective view of a second embodiment of a patient interface device according to the principles of the present invention.
Figure 6:
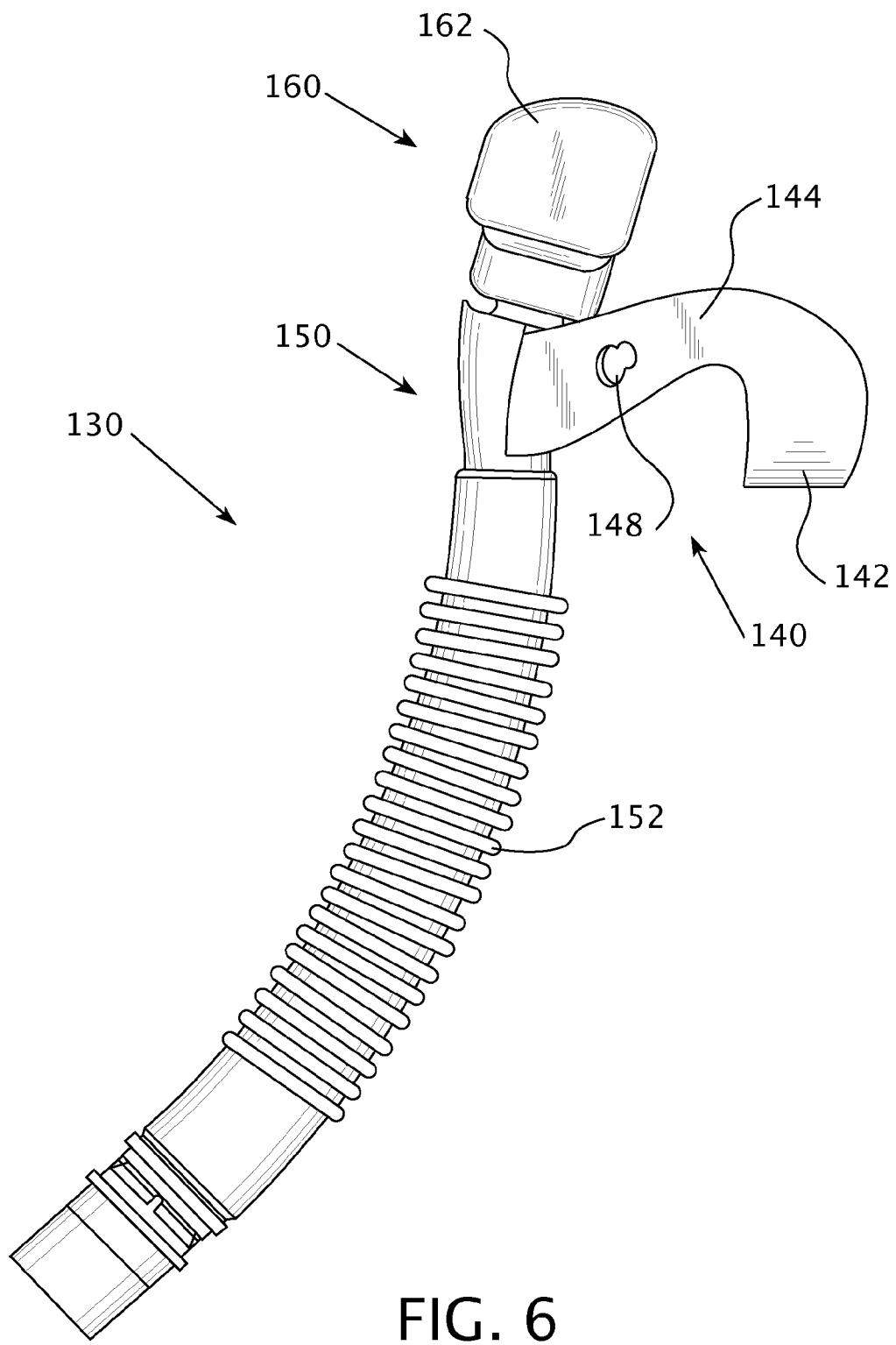
FIGS. 6-8 are a side, front, and exploded views, respectively, of the patient interface device of FIG. 5.
Figure 7:
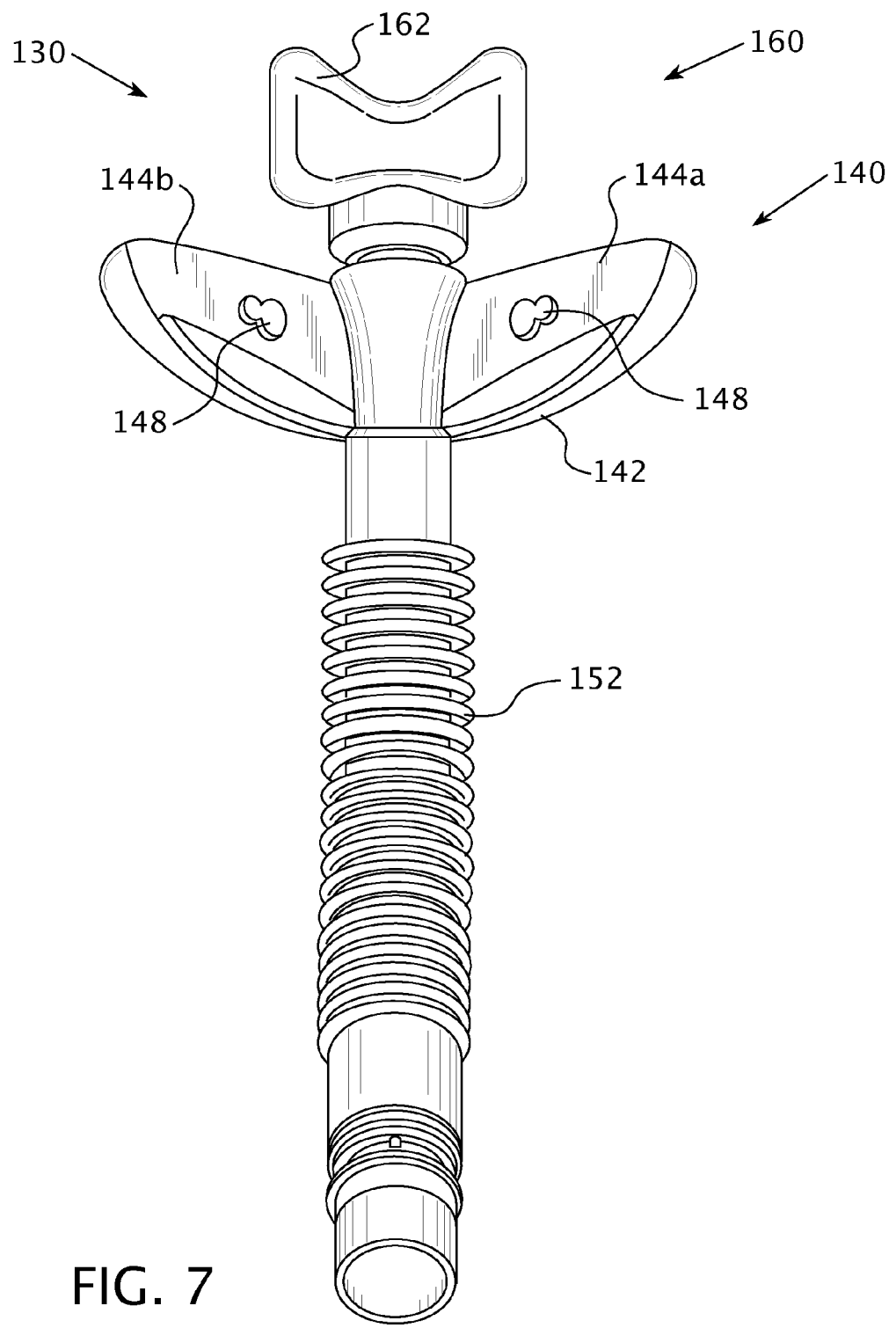
Figure 8:
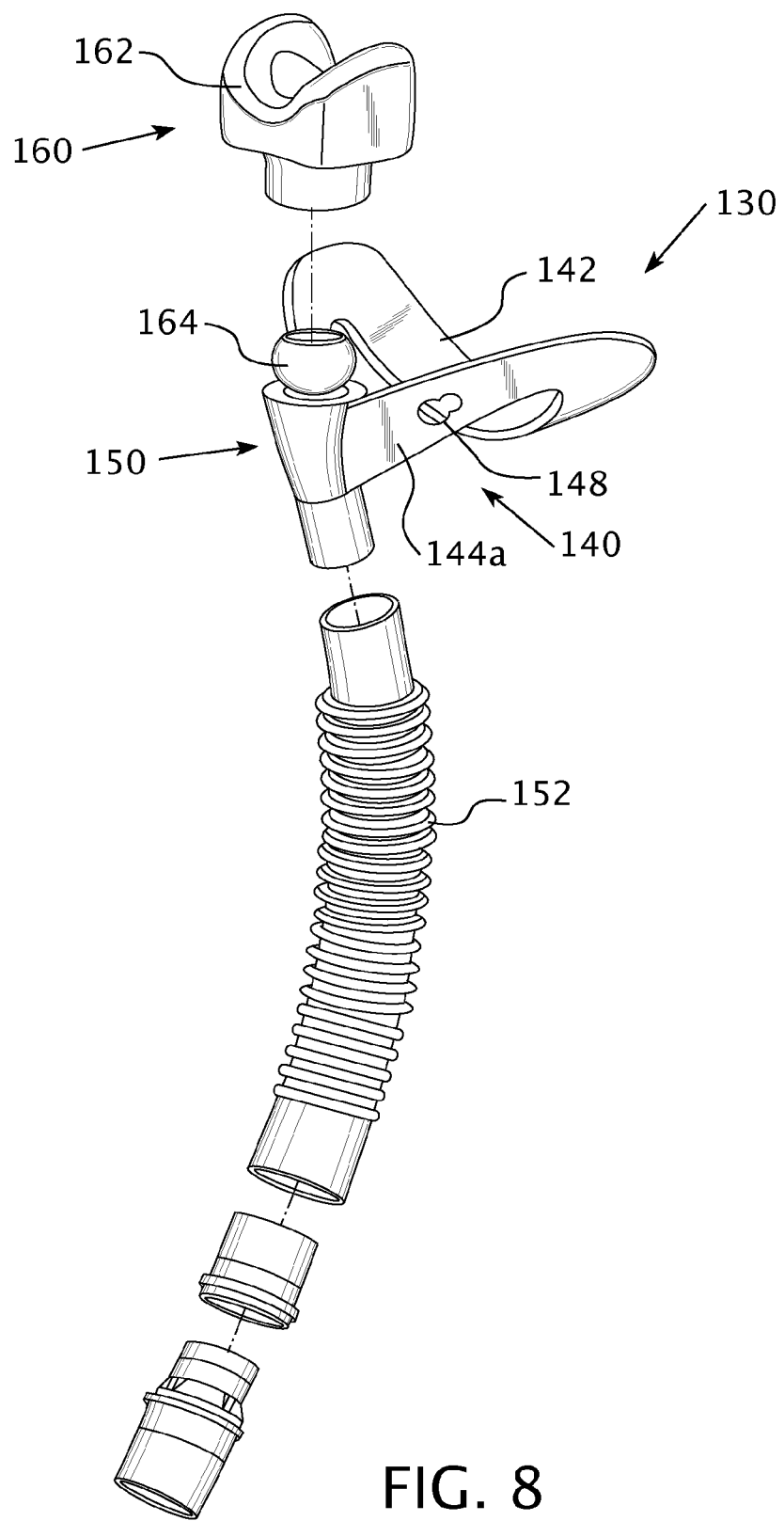
Figure 9:
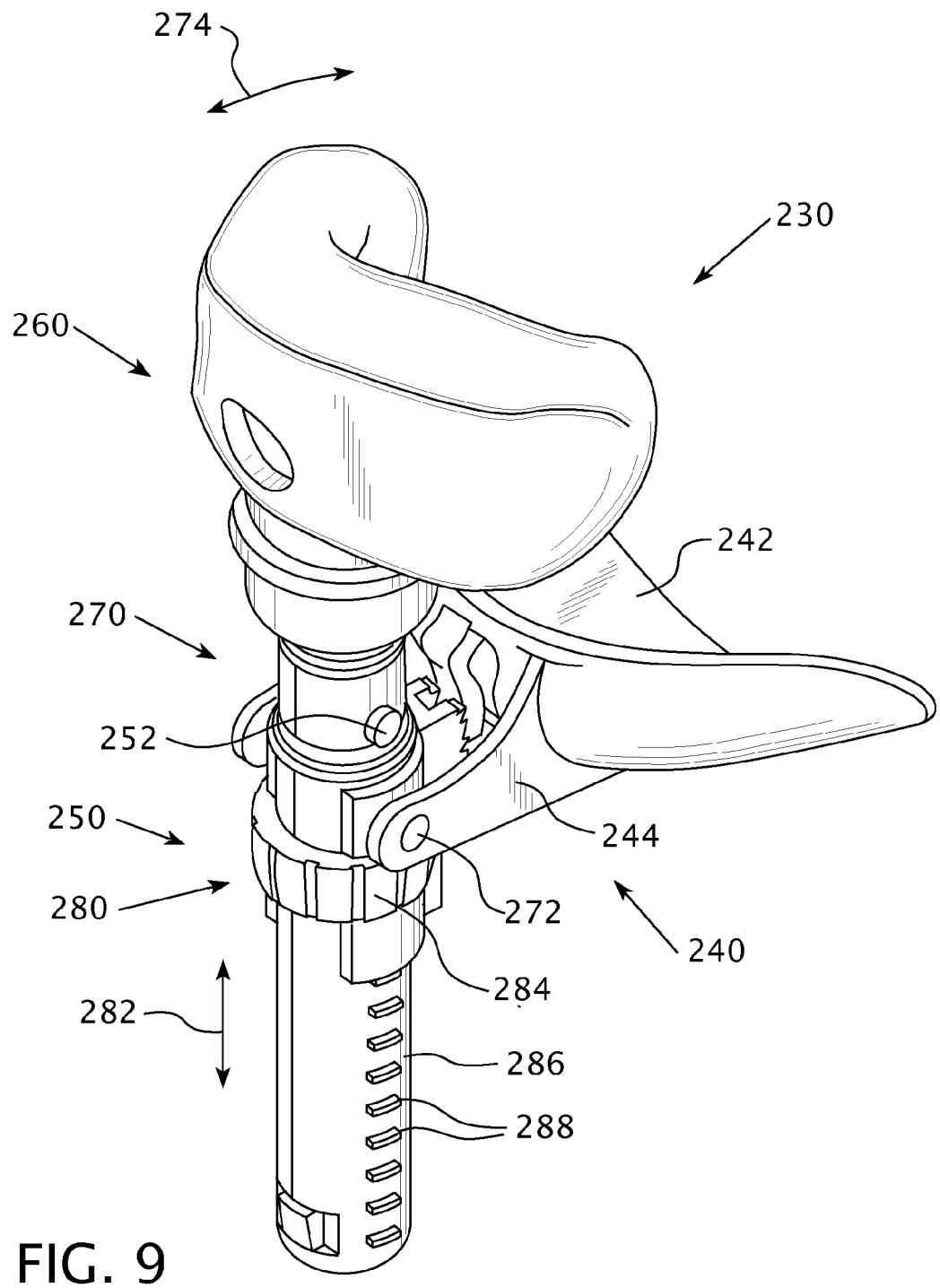
FIG. 9 is a front perspective view of a third embodiment of a patient interface device according to the principles of the present invention.
Figure 10:
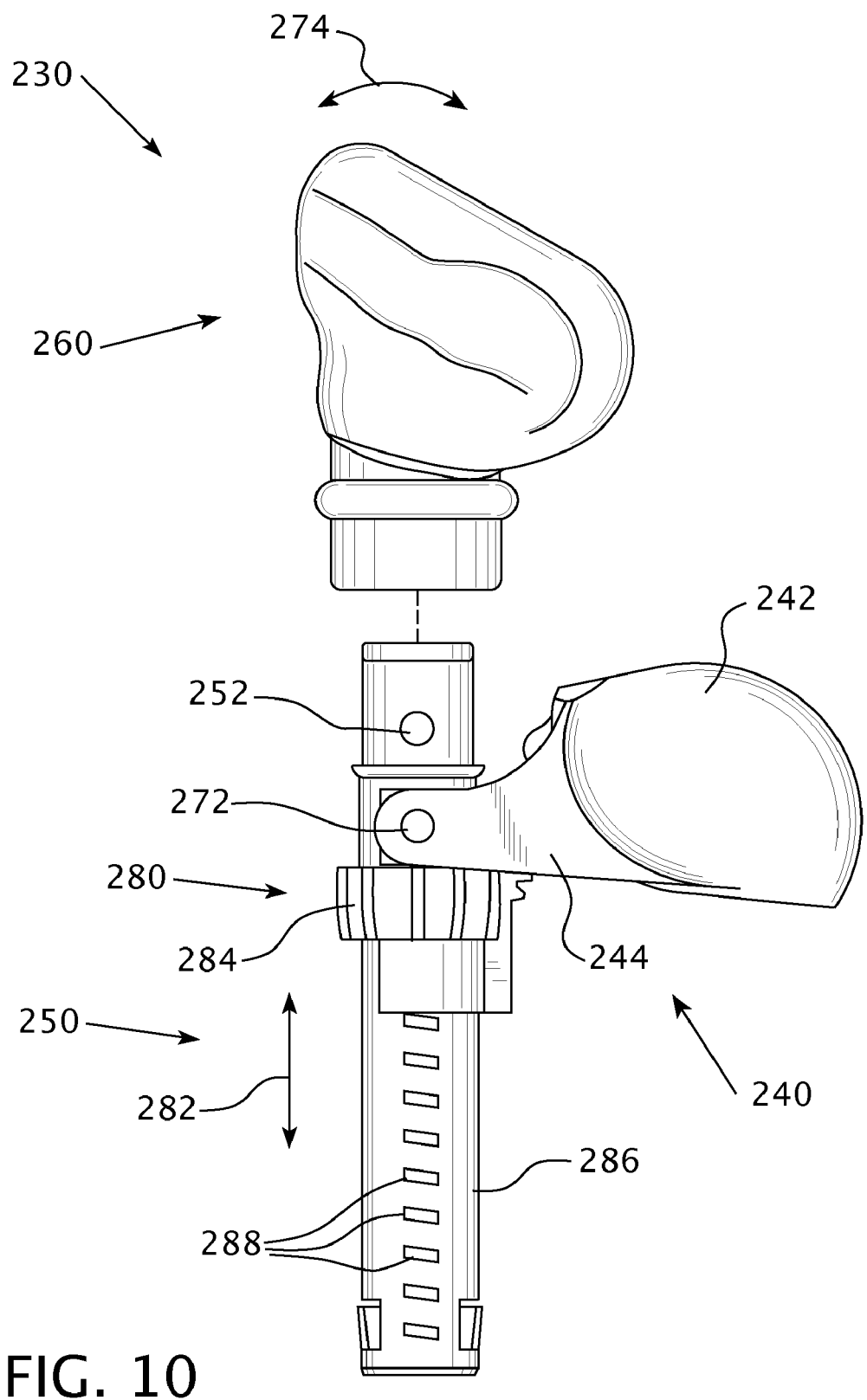
FIGS. 10-12 are a side, front, and exploded views, respectively, of the patient interface device of FIG. 9.
Figure 11:
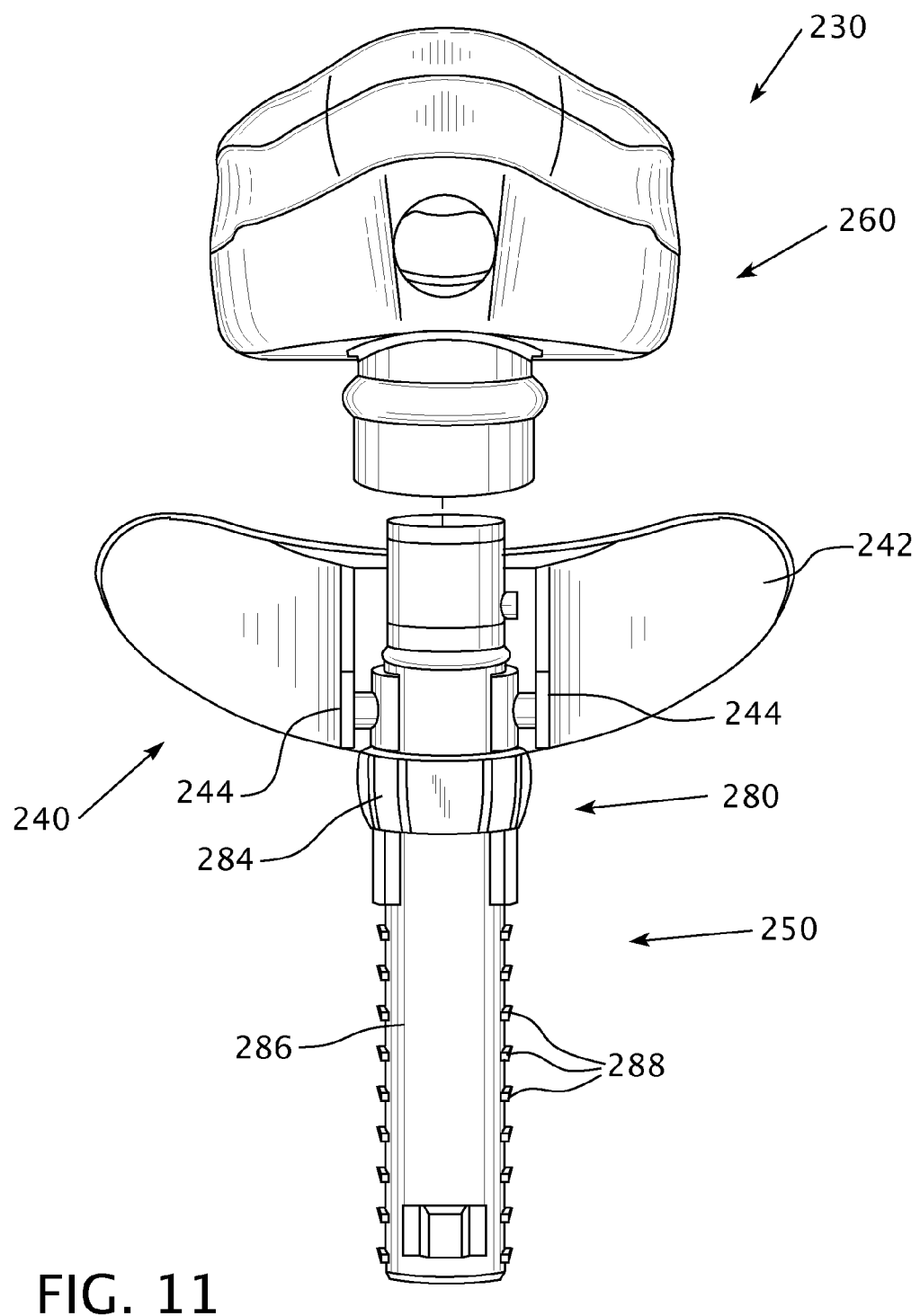
Figure 12:
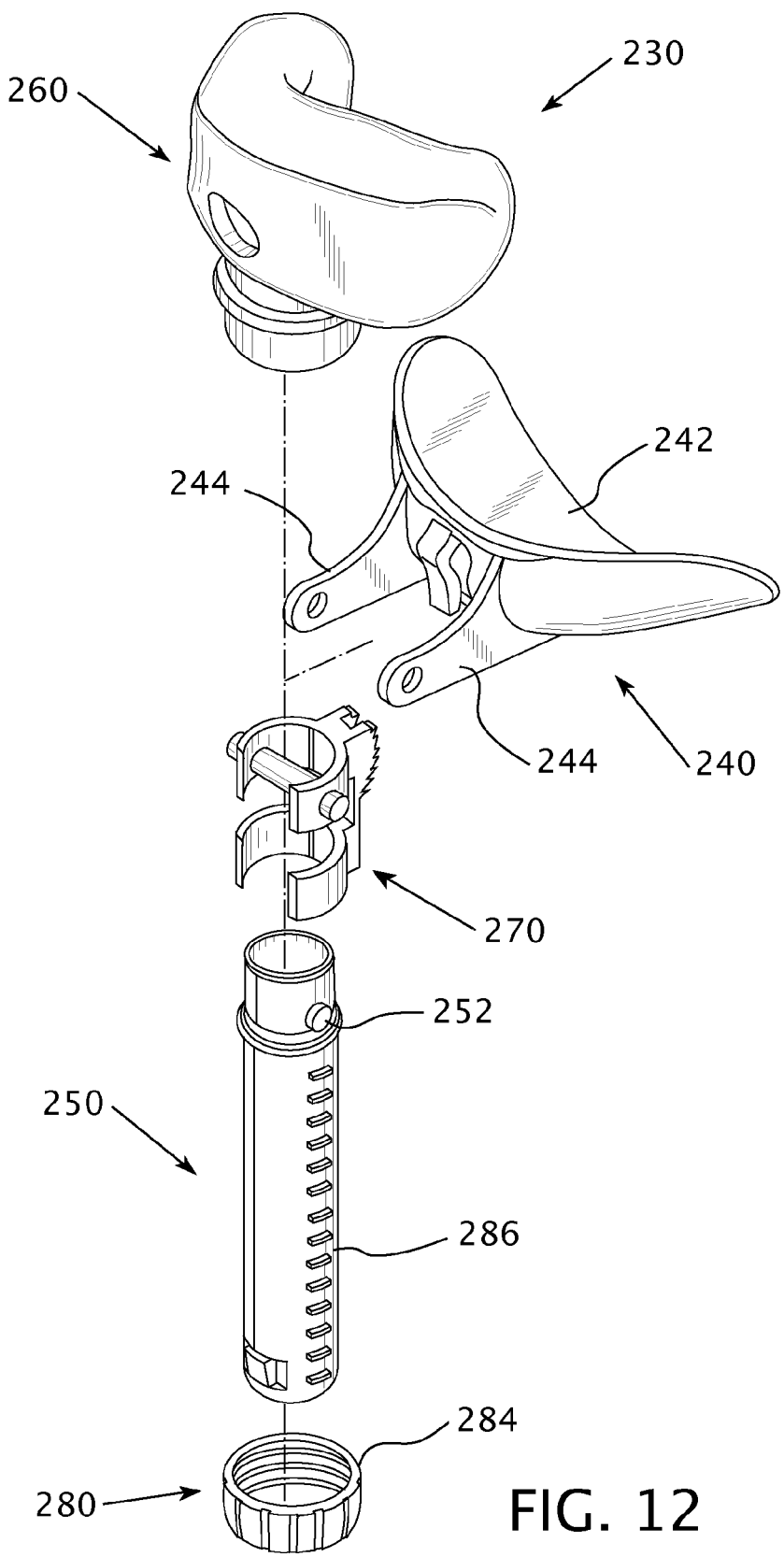
Figure 13:
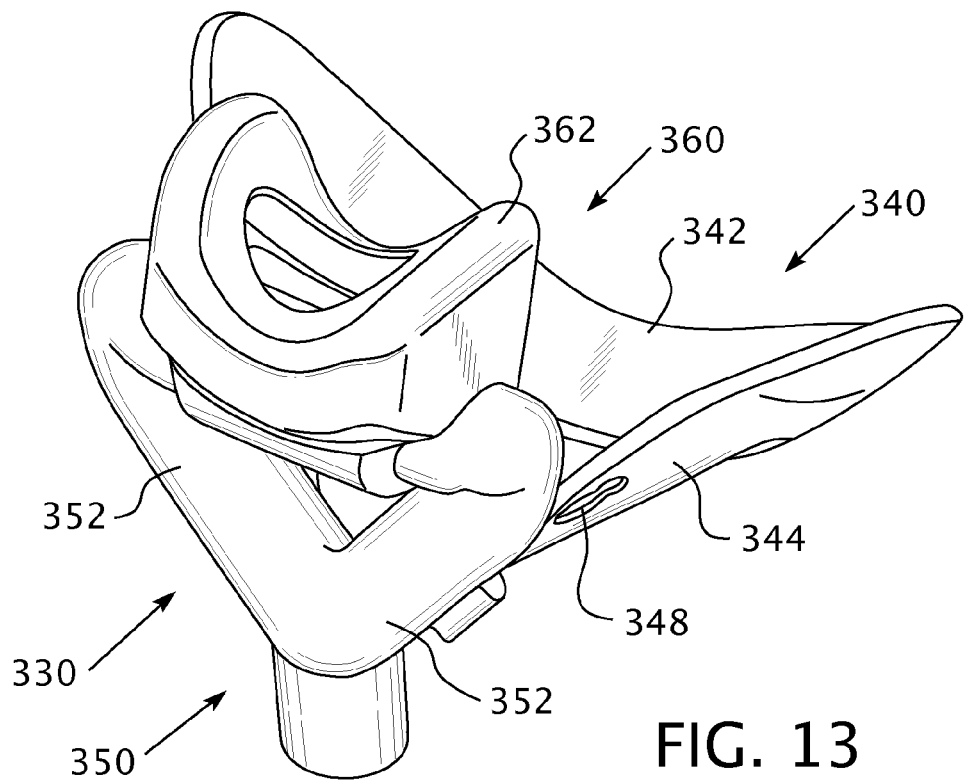
FIG. 13 is a front perspective view of a fourth embodiment of a patient interface device according to the principles of the present invention.
Figure 14:
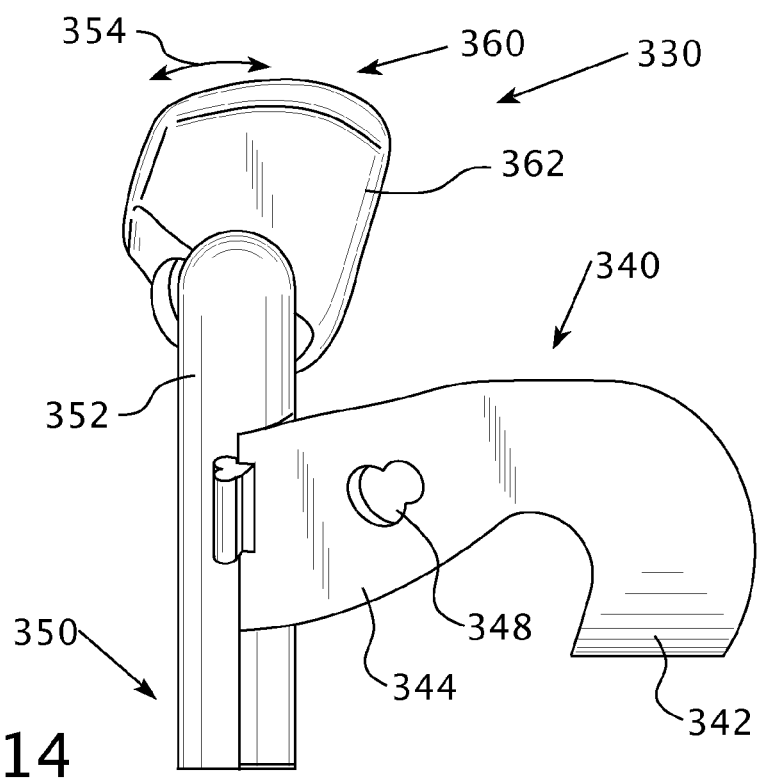
FIGS. 14-16 are a side, front, and exploded views, respectively, of the patient interface device of FIG. 13.
Figure 15:
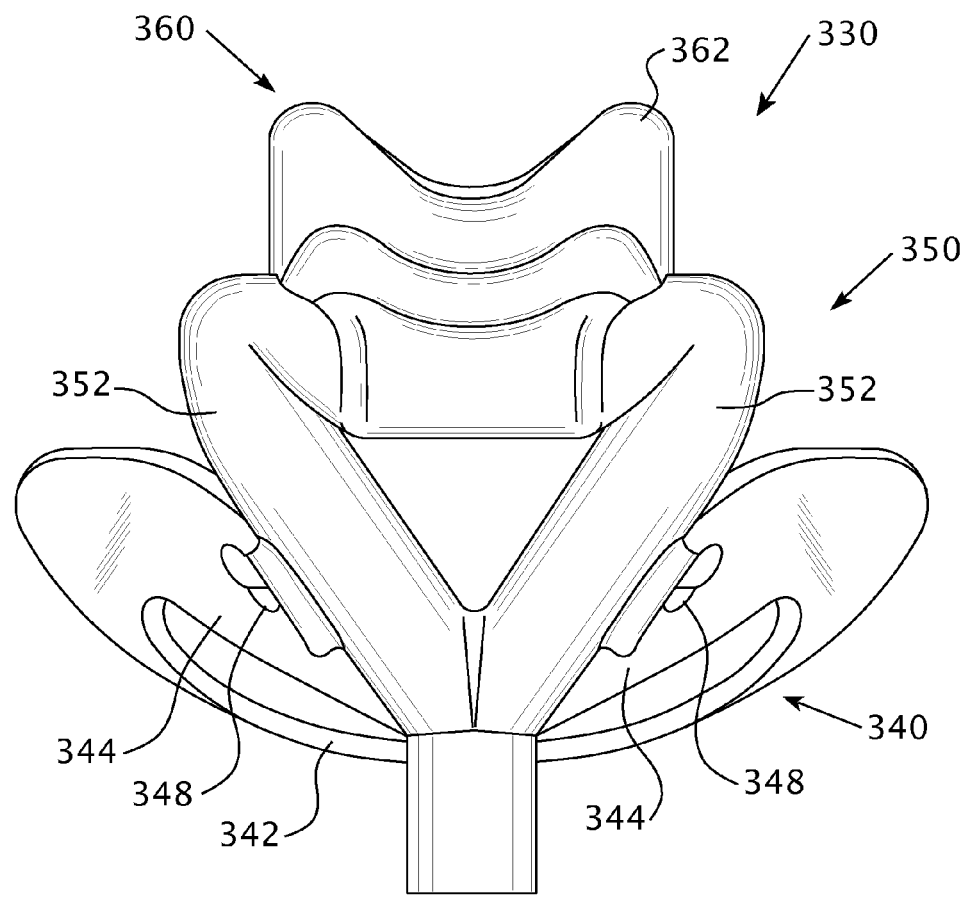
Figure 16:
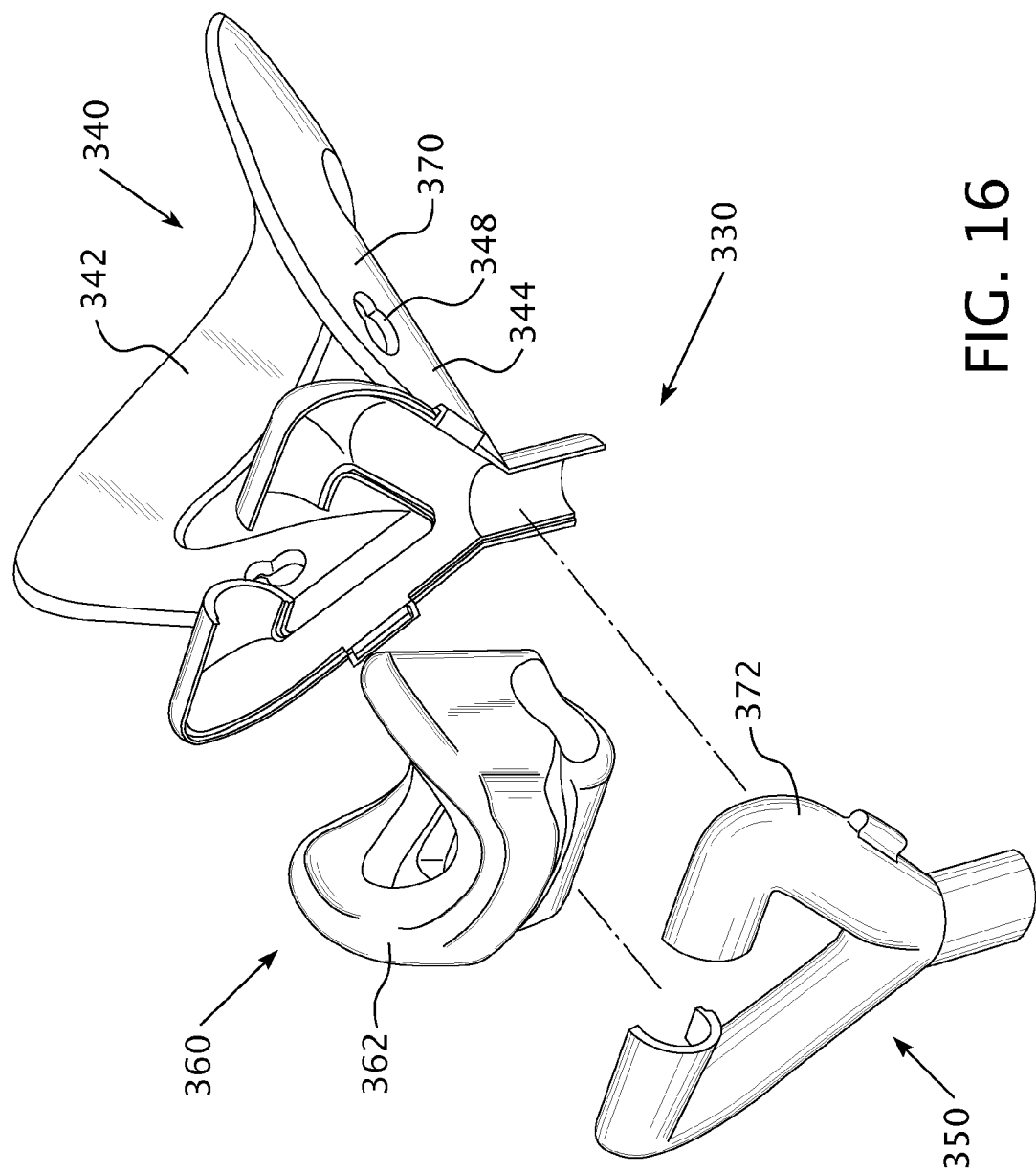
Figure 17:
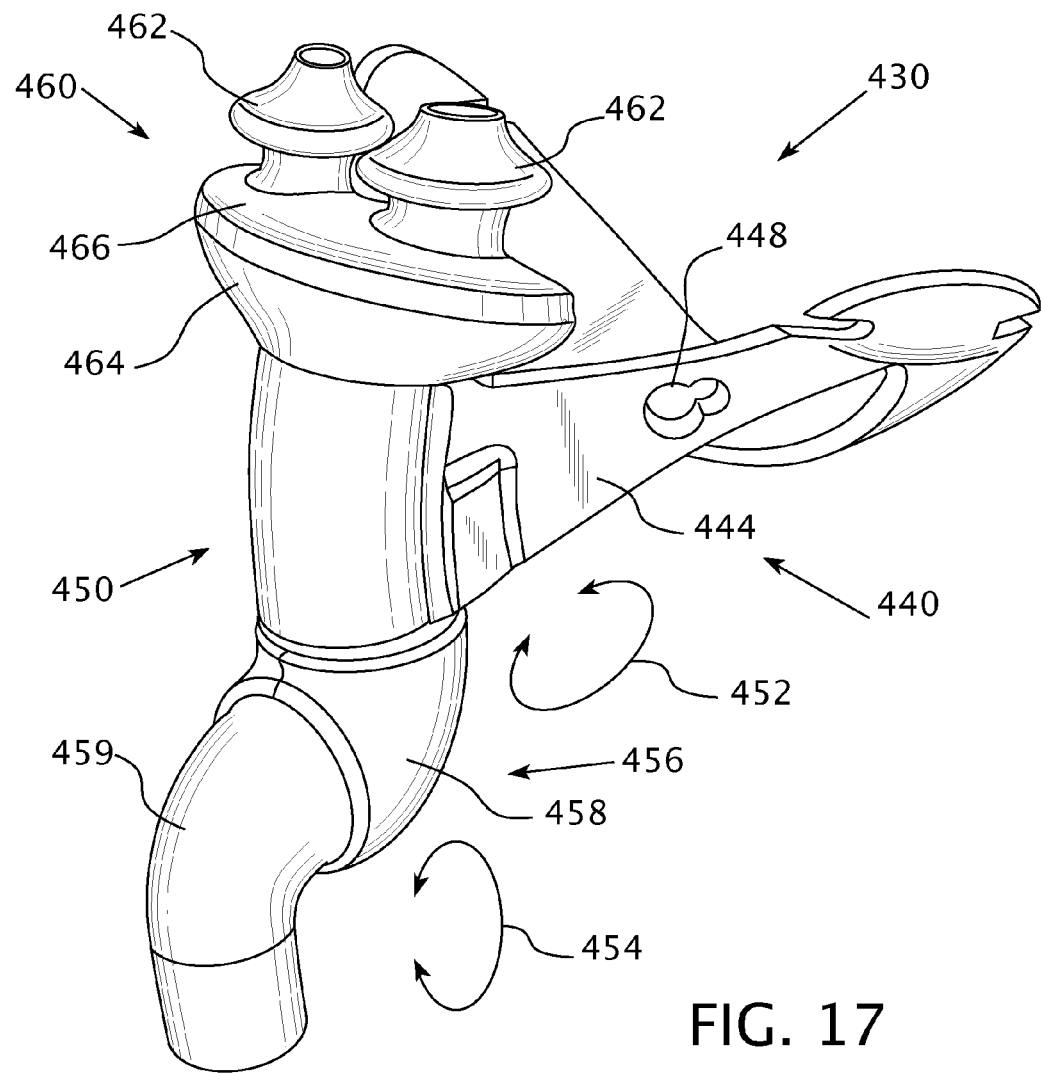
FIG. 17 is a front perspective view of a fifth embodiment of a patient interface device according to the principles of the present invention.
Figure 18:
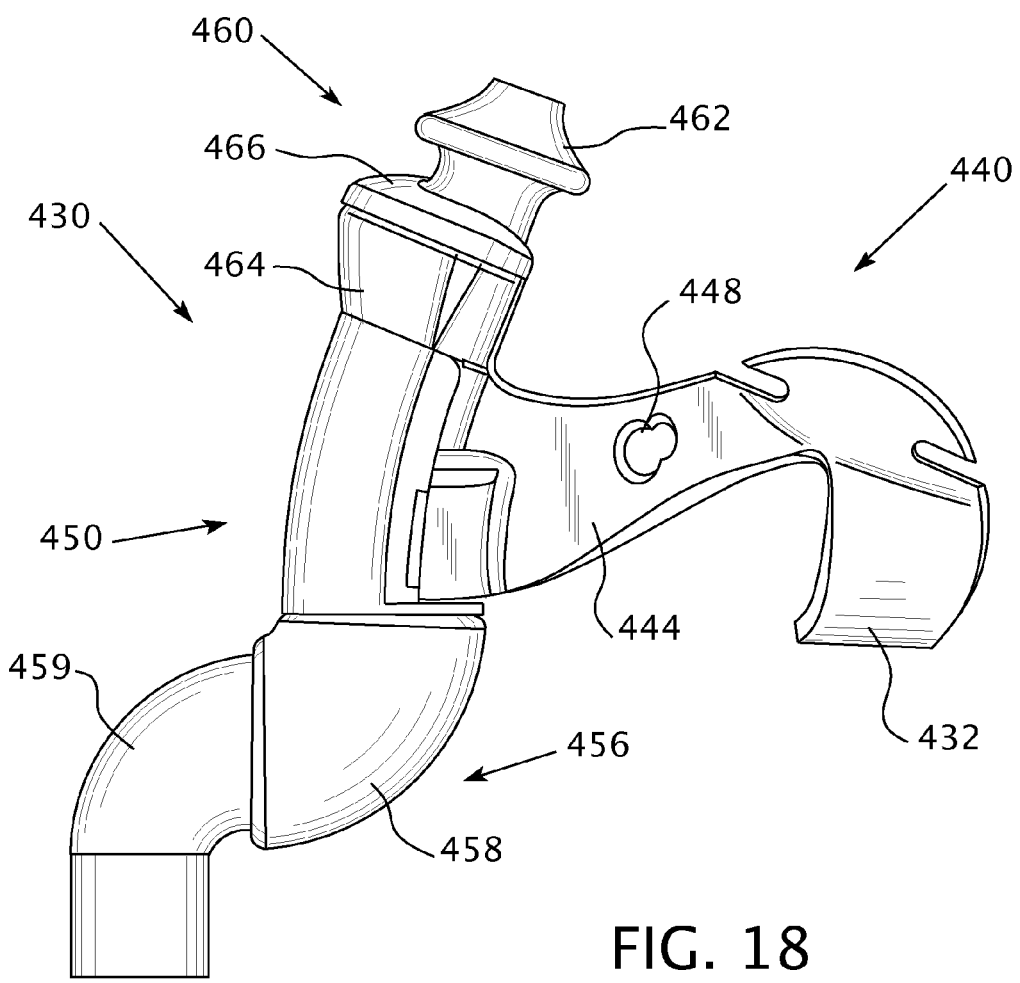
FIGS. 18-20 are a side, front, and exploded views, respectively, of the patient interface device of FIG. 17.
Figure 19:
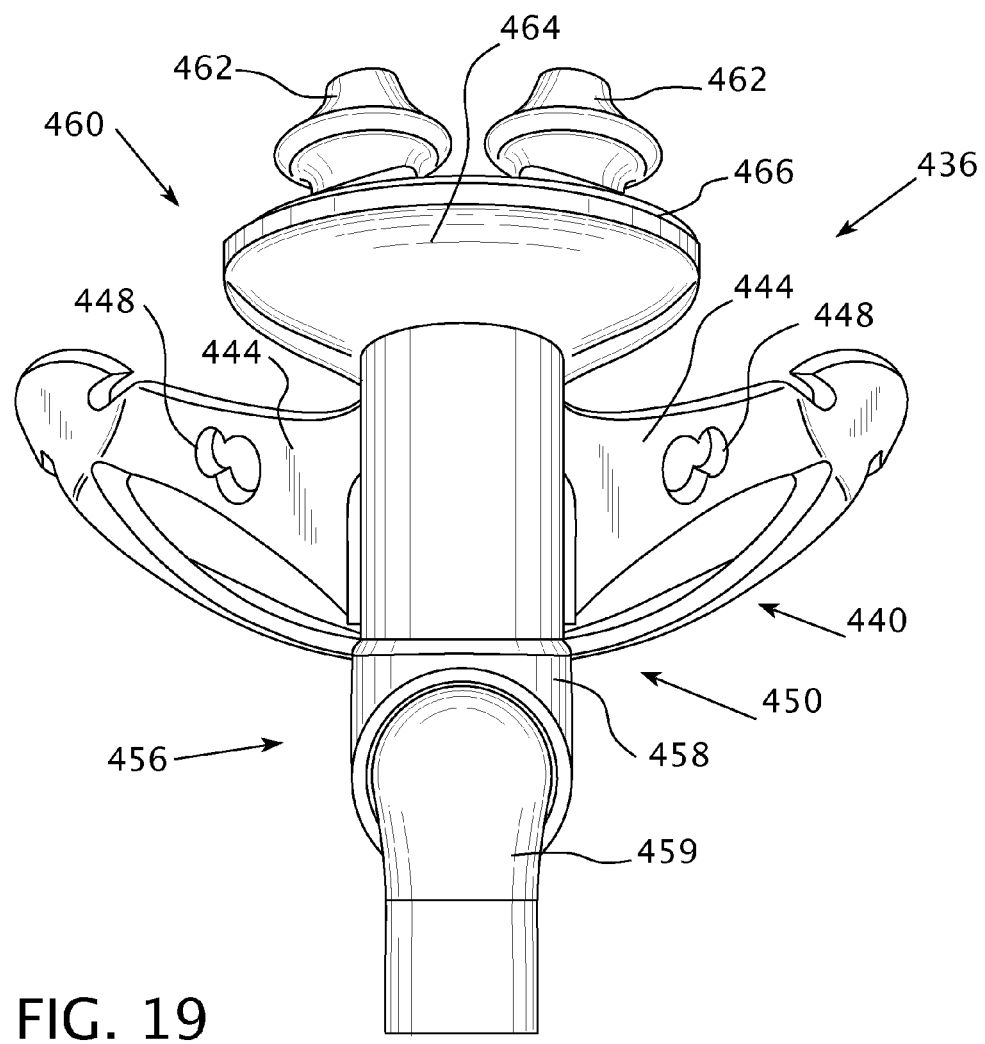
Figure 20:
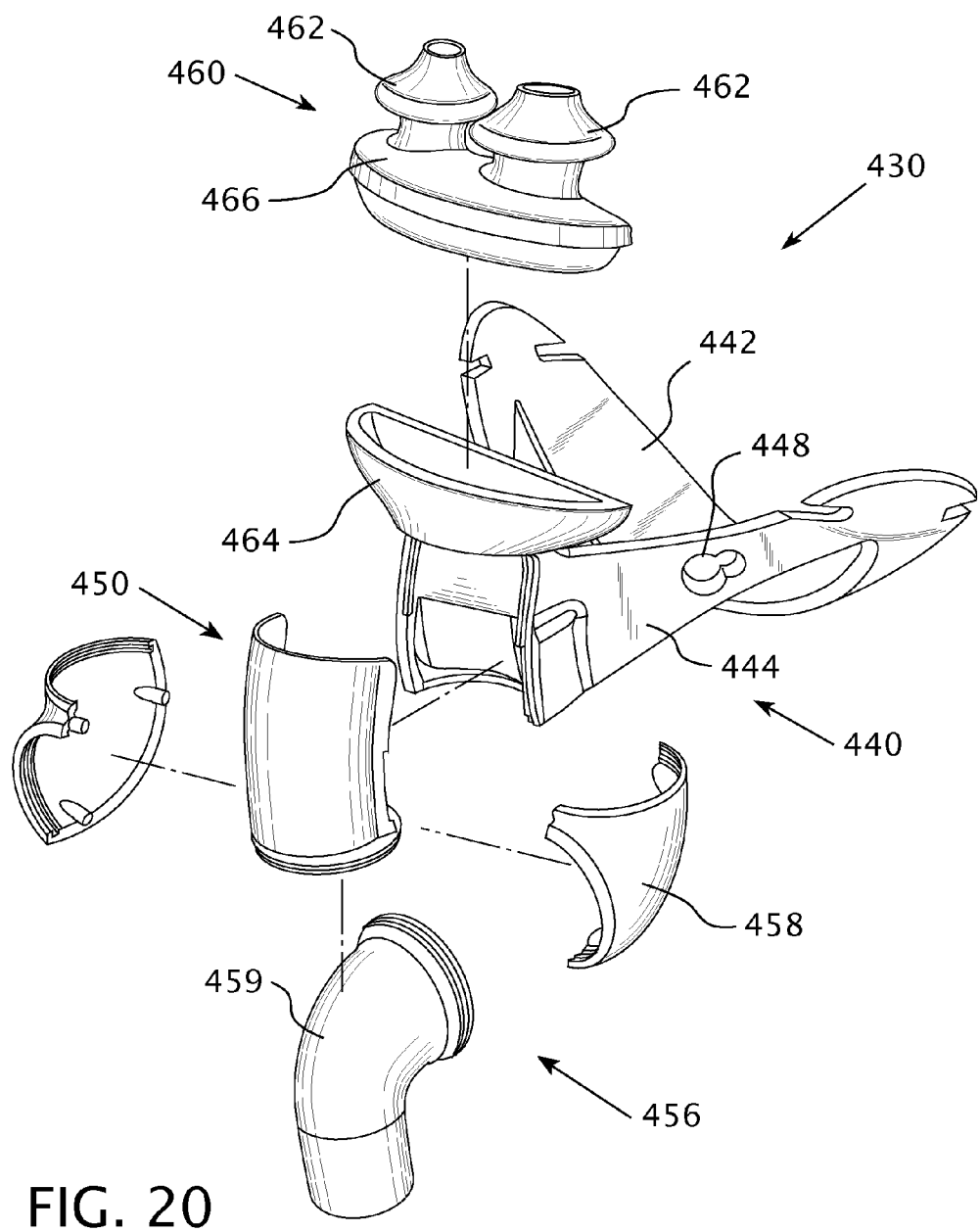
Figure 21:
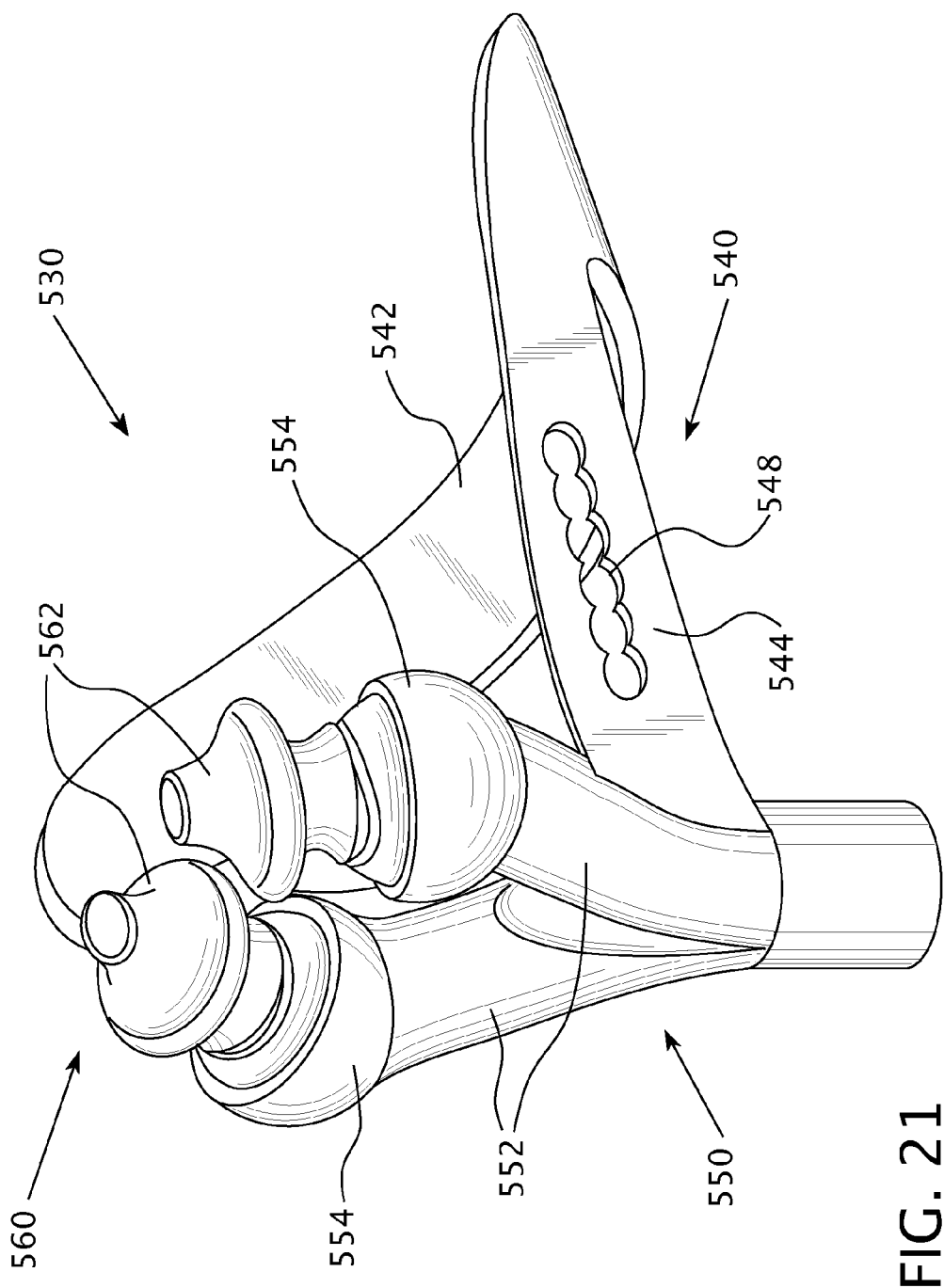
FIG. 21 is a front perspective view of a sixth embodiment of a patient interface device according to the principles of the present invention.
Figure 22:
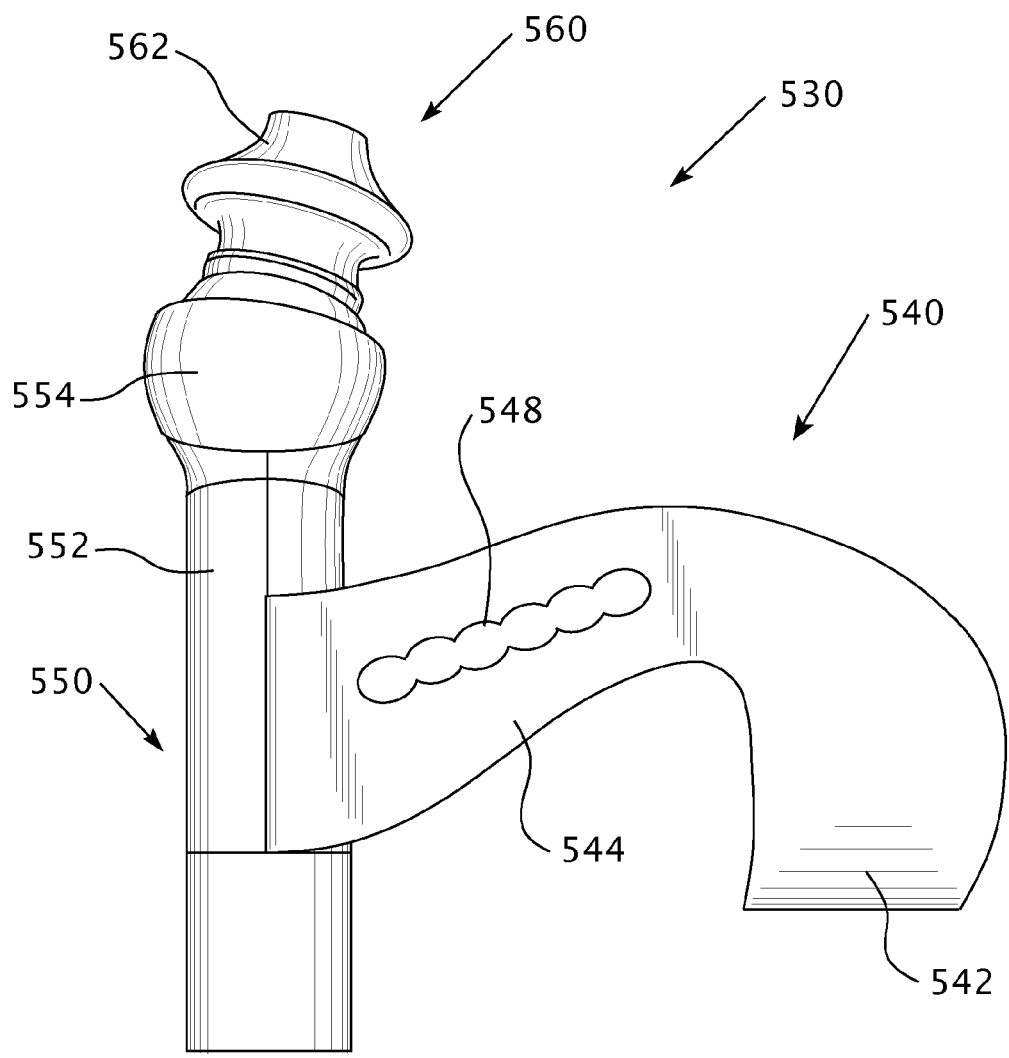
FIGS. 22-24 are a side, front, and exploded views, respectively, of the patient interface device of FIG. 21.
Figure 23:
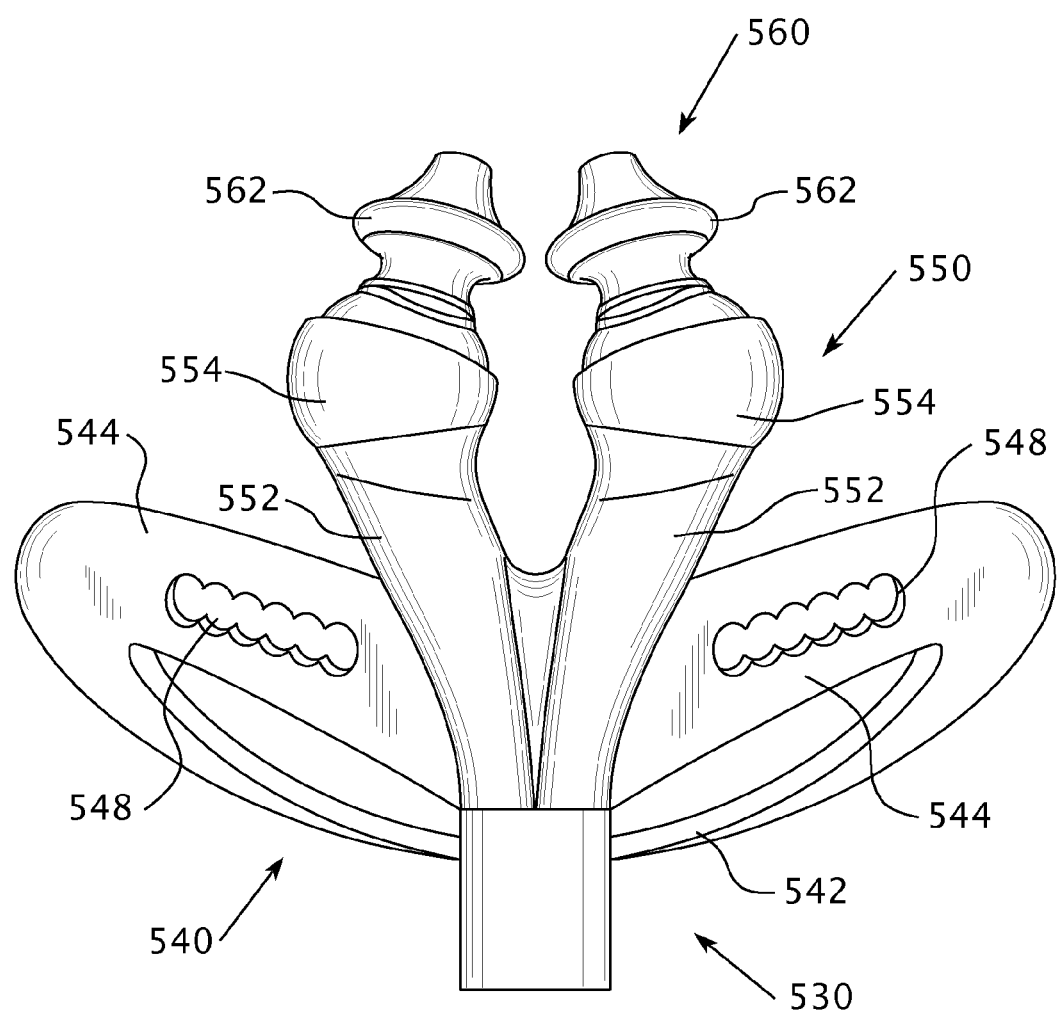
Figure 24:
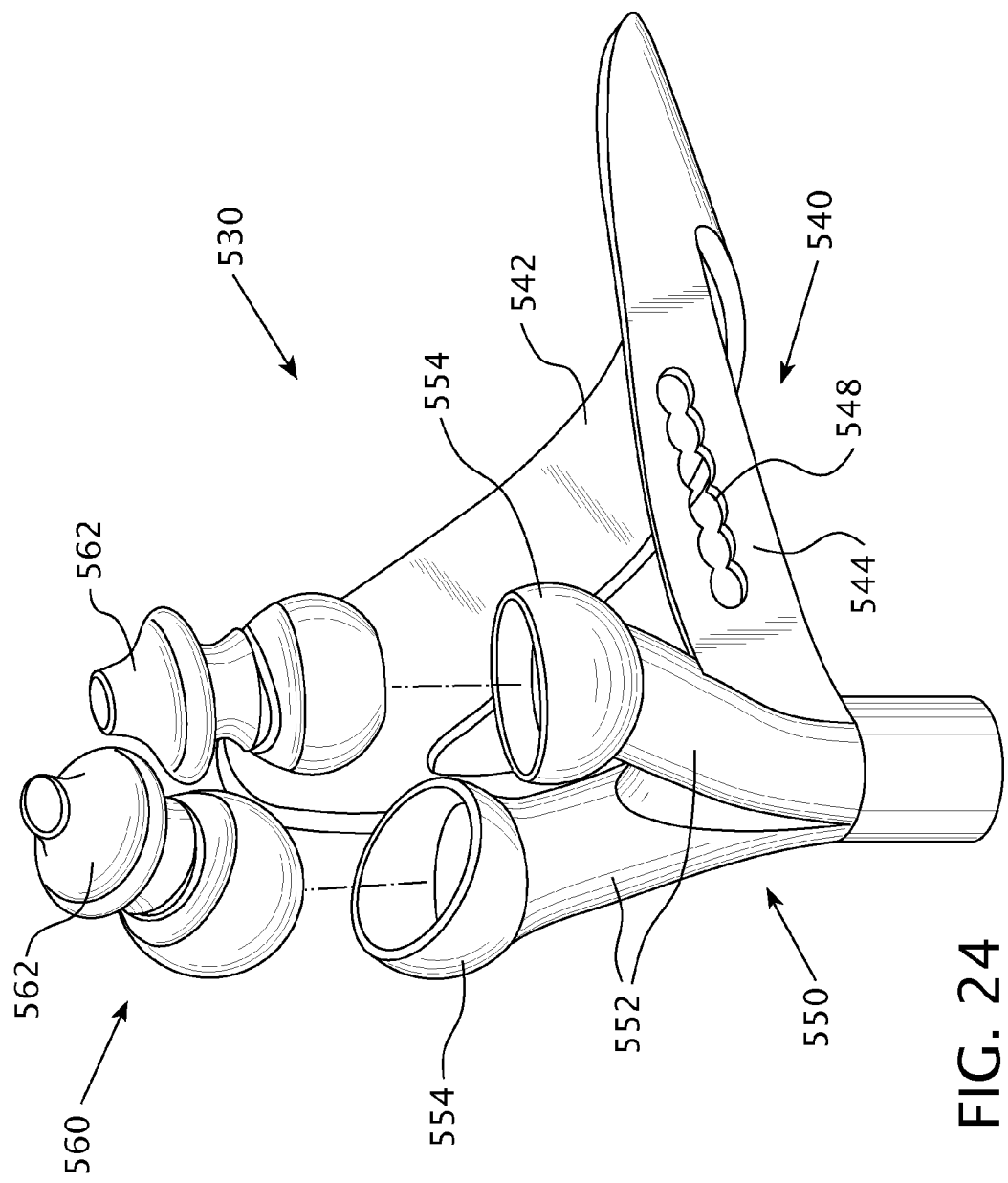
Figure 25:
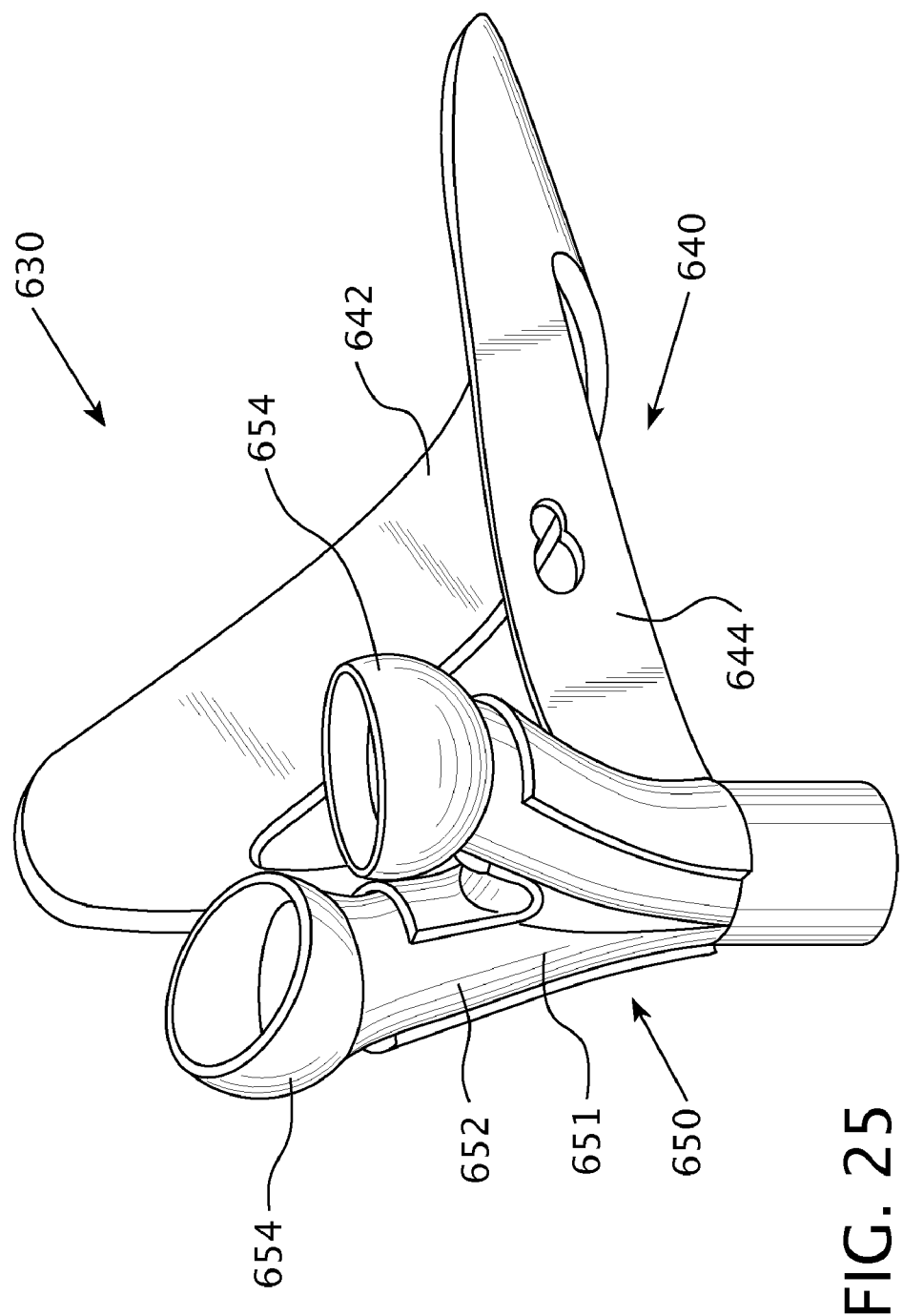
FIG. 25 is a front perspective view of a seventh embodiment of a patient interface device according to the principles of the present invention.
Figure 26:
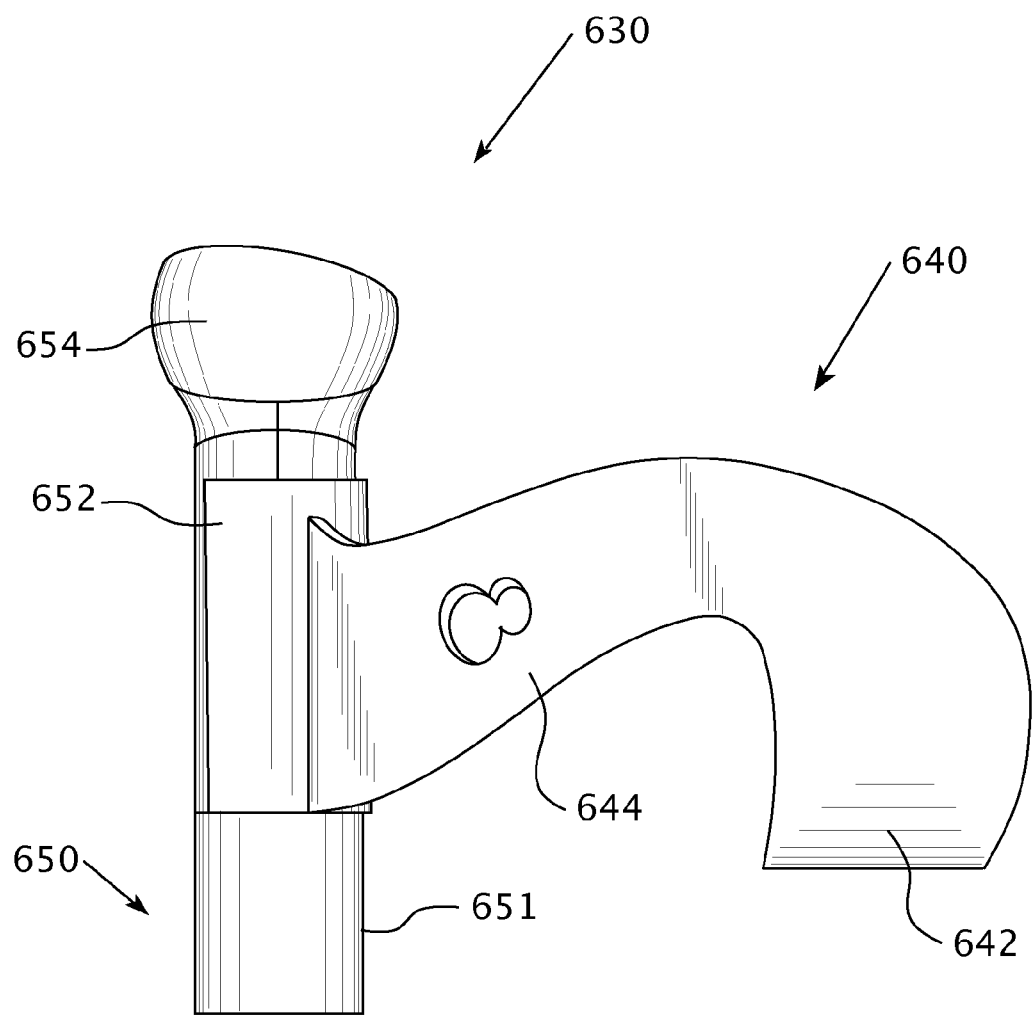
FIGS. 26-28 are a side, front, and exploded views, respectively, of the patient interface device of FIG. 25.
Figure 27:
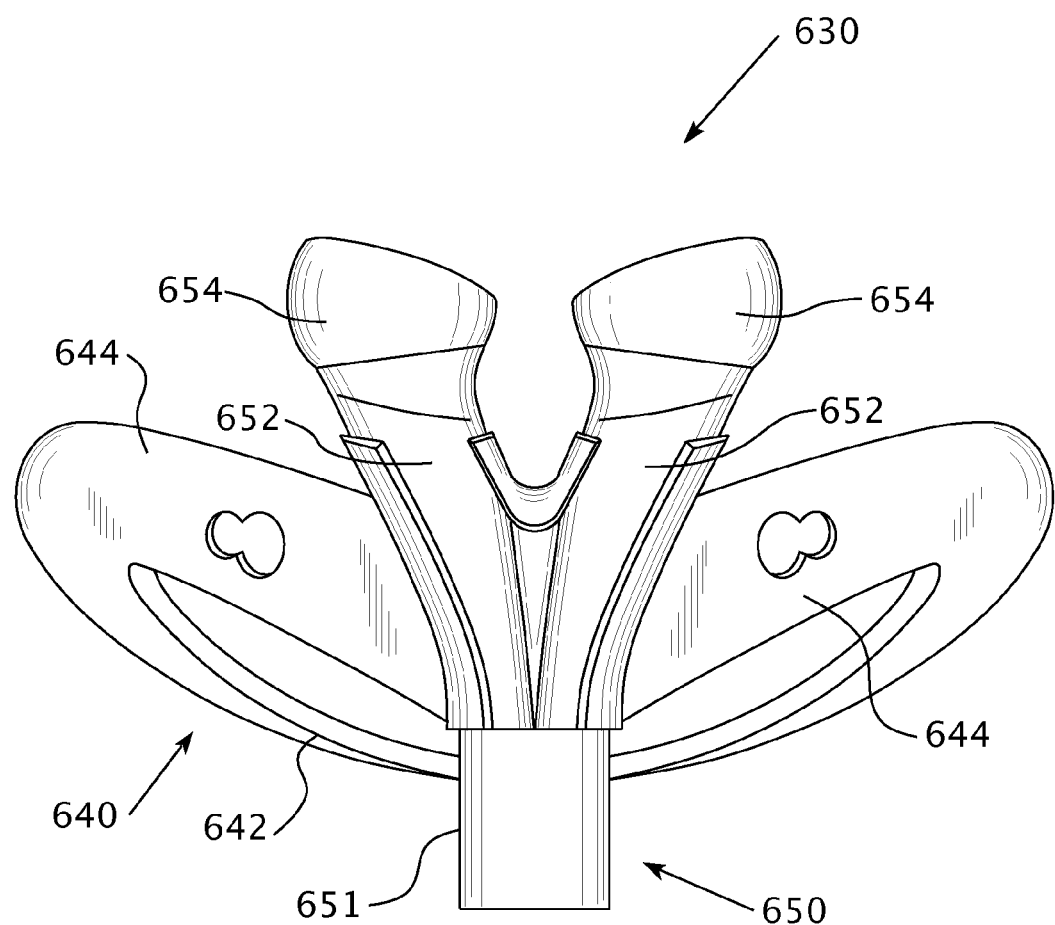
Figure 28:
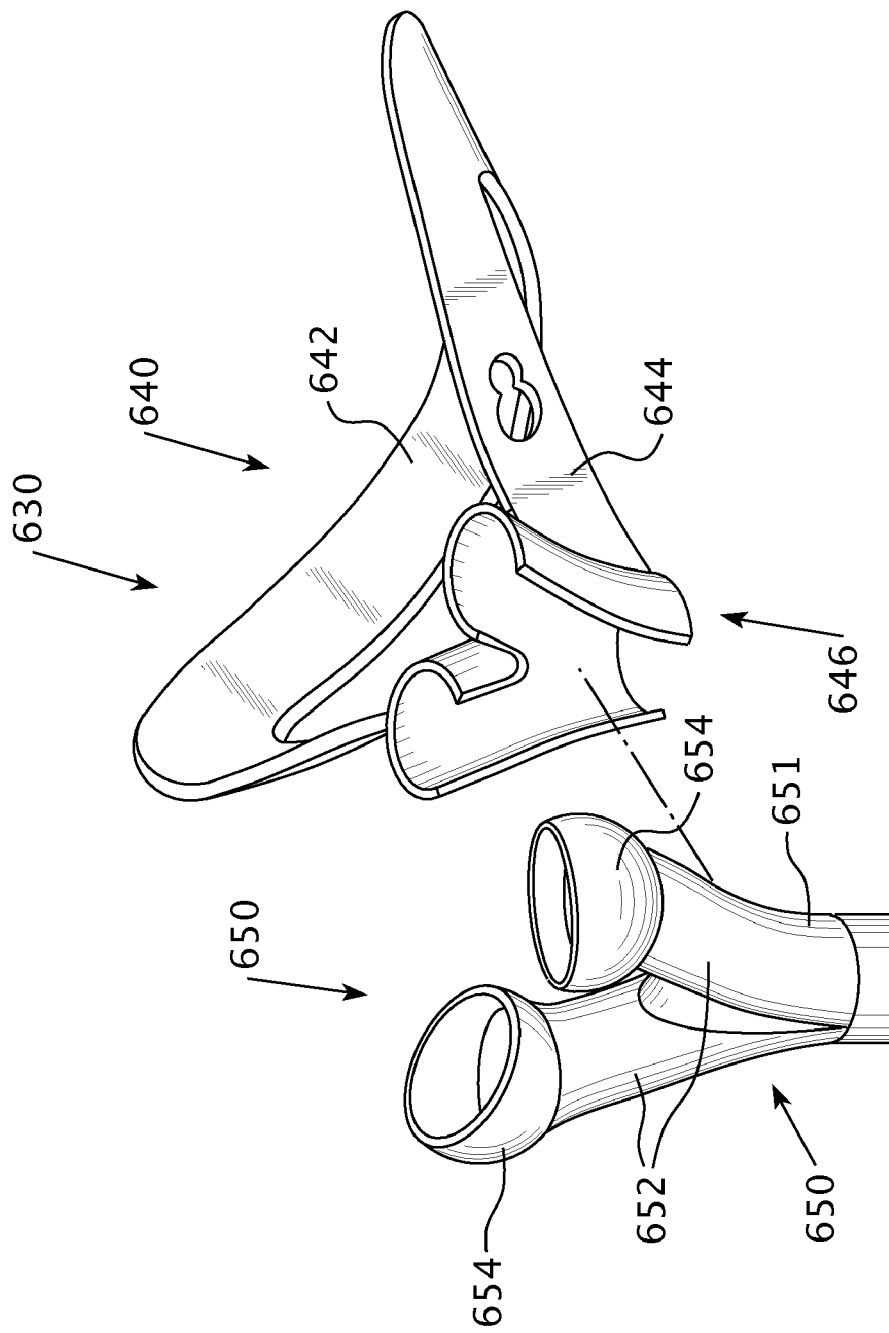

FIGS. 1-4 illustrate a first embodiment of a patient interface device 30 according to the principles of the present invention. Patient interface device 30 is shown schematically connected to a pressure support system 32 via a patient circuit 34, which communicates gas from the pressure support system to the patient interface device. Patient circuit 34 is any device, such as a flexible tubing, that carries the flow of gas from the pressure/flow generator in the pressure support system to the patient interface device.

Pressure support system 32 is any conventional ventilation or pressure support system. Examples of such pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device.

Patient interface device 30 includes a body portion 40, a circuit portion 50, and a patient interface portion 60. Body portion 40 includes a chin support 42, a pair of arms 44, and a circuit coupling portion 46. In the illustrated exemplary embodiment, body portion 40 is formed as a single piece from a relatively rigid material. When the patient interface device is donned by the user, chin support 42 passes under the mandible from one side of the face to the other. Each one of arms 44 extend from circuit coupling portion 46 to opposite ends of chin support 42. Circuit coupling portion 46 attaches circuit portion 50 to the body portion.

The present invention contemplates providing a pad or multiple pads on chin support 42, arms 44, or both. Such pads can be made from any suitable material or combination of materials, such as gel, foam, silicon. Example of gel materials suitable for use as these pads are described in U.S. Pat. Nos. 5,647,357; 5,884,624; 6,397,847; and 6,895,965 and pending U.S. patent application Ser. No. 11/715,760, filed Mar. 8, 2007, publication no. 2007/0221227 ("the '760 application") (collectively referred to as "the gel references"), the contents of each of which are incorporated herein by reference.

A plurality of headgear attachment elements 48 are provided on arms 44. In the illustrated exemplary embodiment, a headgear mount 52 attaches to one of the headgear attachment elements to attach a headgear strap 54 to patient interface device 30. Although three headgear attachment elements 48 are shown as being provided on each arm, the present invention contemplates providing only or more than three such elements on the arms. The headgear attachment elements are any structure that is capable of attaching headgear mount 52 to the arm. In the illustrated embodiment, the headgear attachment elements are simply an opening defined in the arm into which a male portion of the headgear inserts and is retained.

Of course, any fastening technique for joining the headgear strap, and hence, the headgear clip, to the support frame are contemplated by the present invention, including snaps, hooks, loops, clamps, or other connectors. Examples of fastening techniques suitable for use with the present invention are described in U.S. Pat. No. 7,066,179, the contents of which are incorporated herein by reference.

Figure 36:
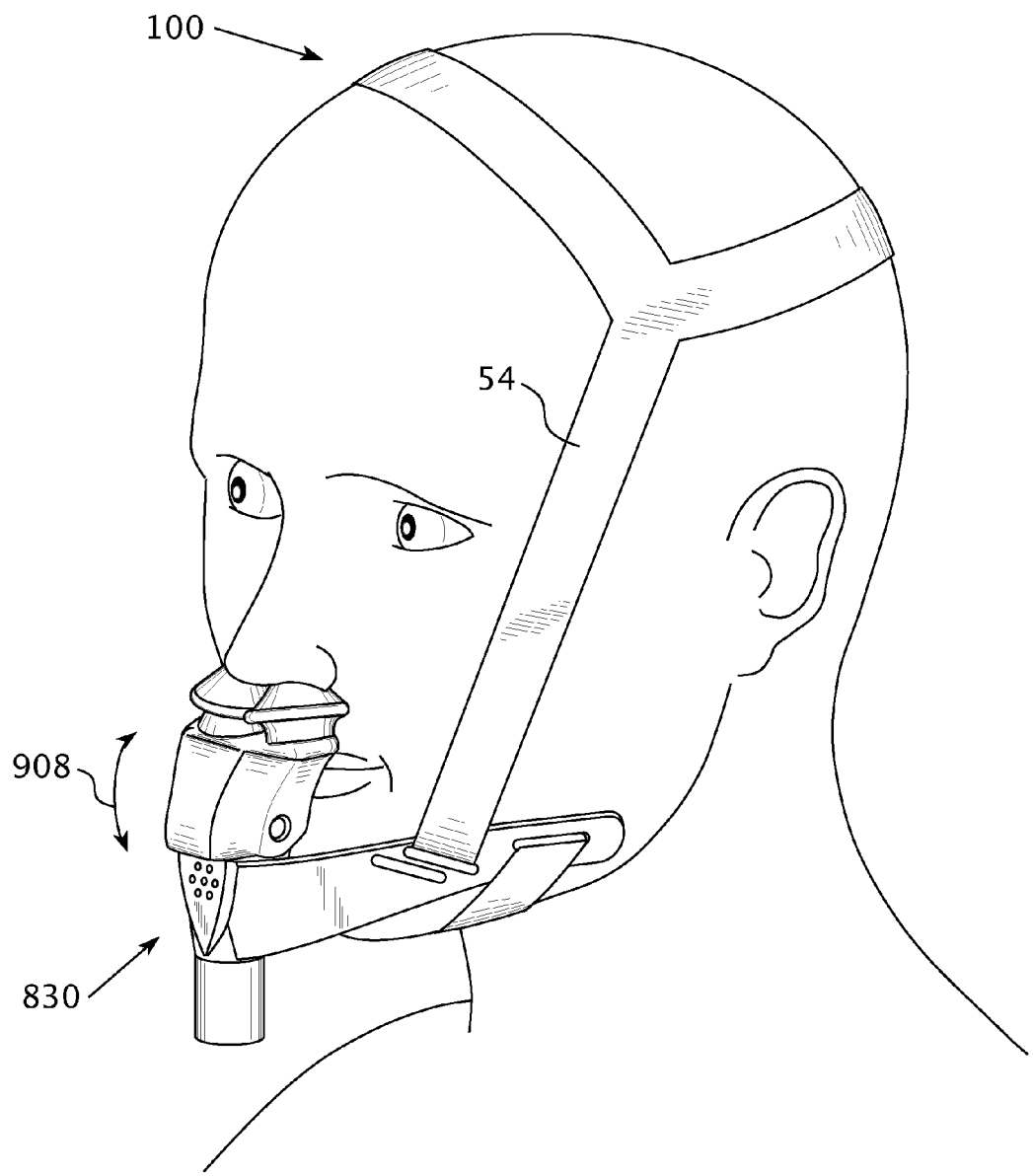
FIGS. 36 and 37 are front perspective and side views, respectively, illustrating the positioning of the patient interface device of FIG. 30 on a user.
Figure 37:
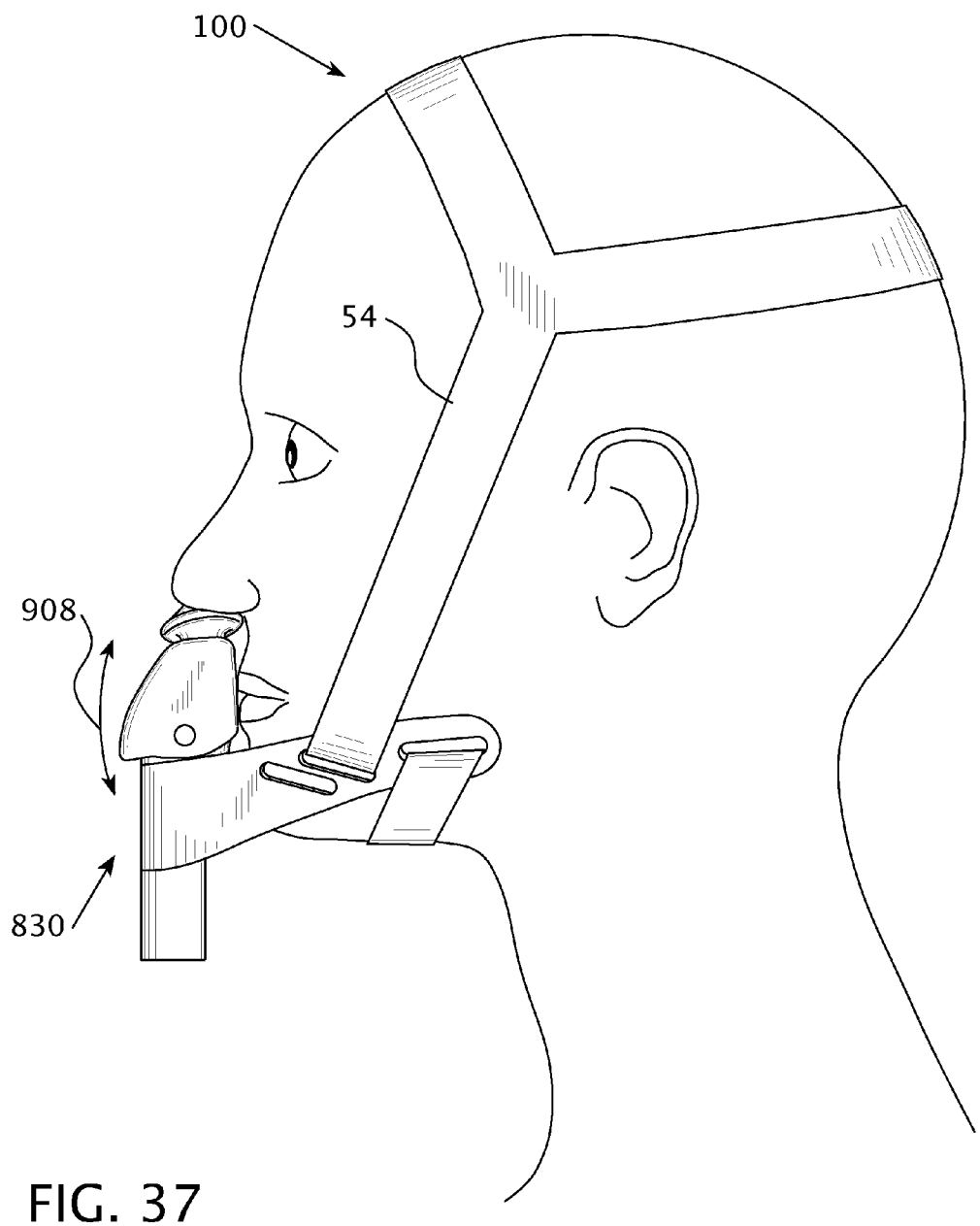
Figure 38:
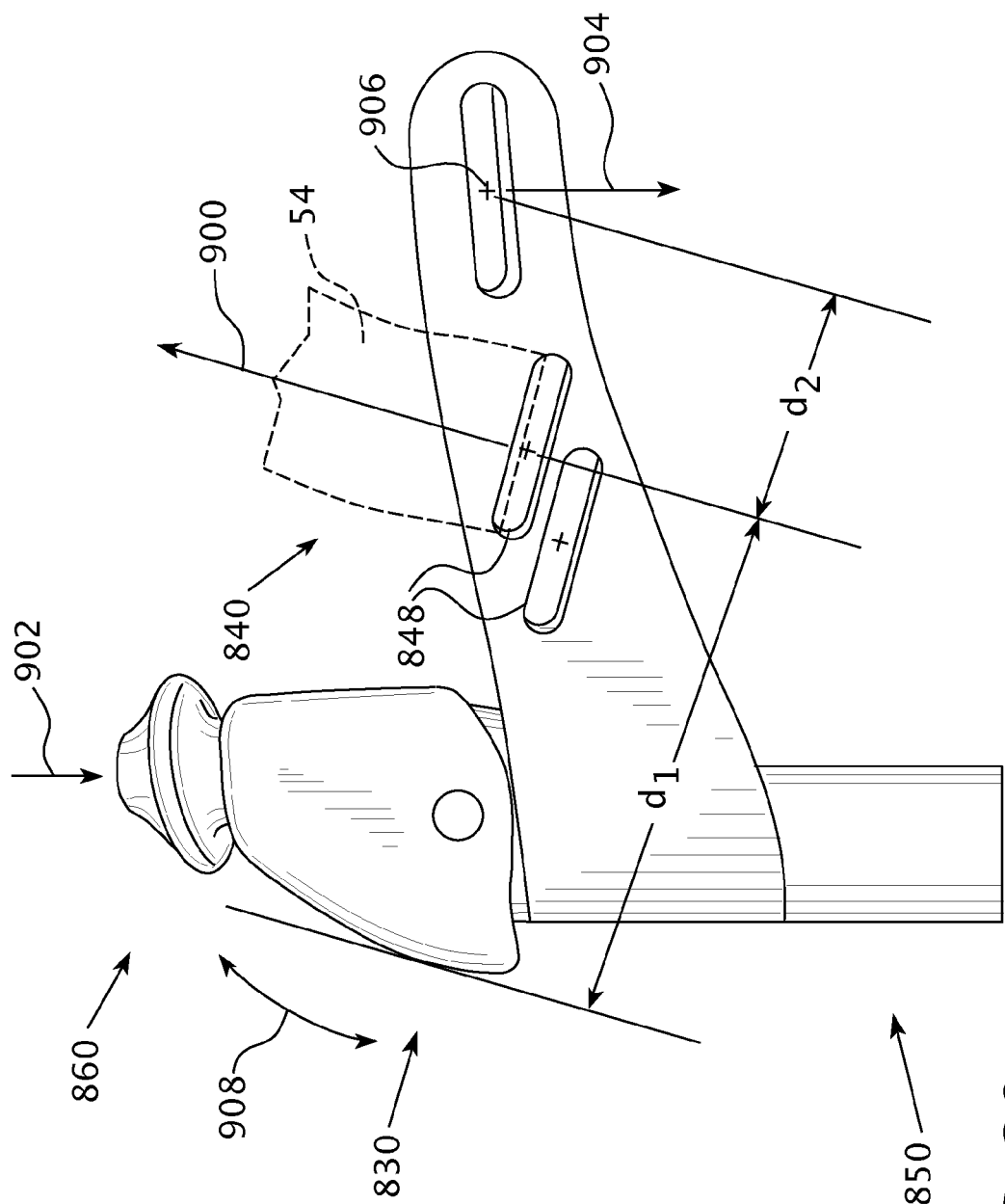
FIG. 38 is a side view of the patient interface device of FIG. 30.
Figure 39A:
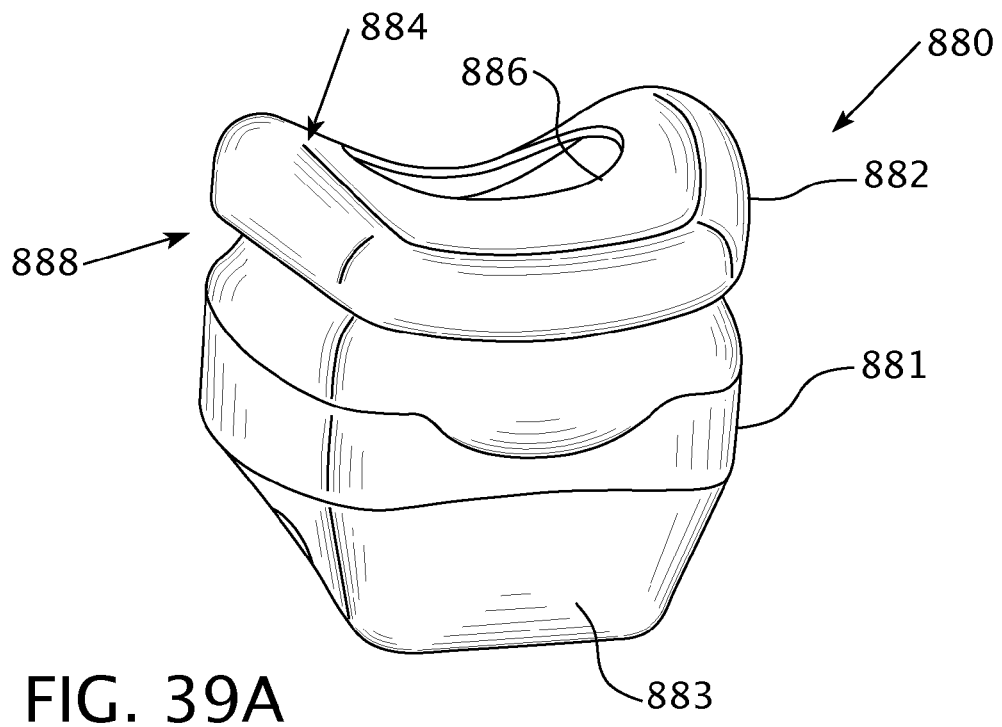
FIGS. 39A-39D are front perspective, front, side, and top views, respectively, of an alternative embodiment for the patient interface portion of the patient interface device of FIG. 30.
Figure 39B:
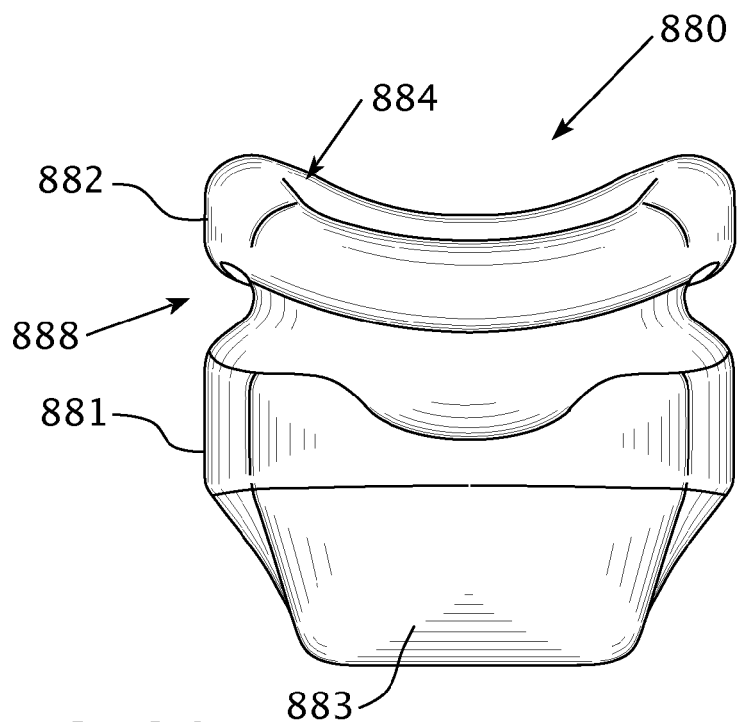
Figure 39C:
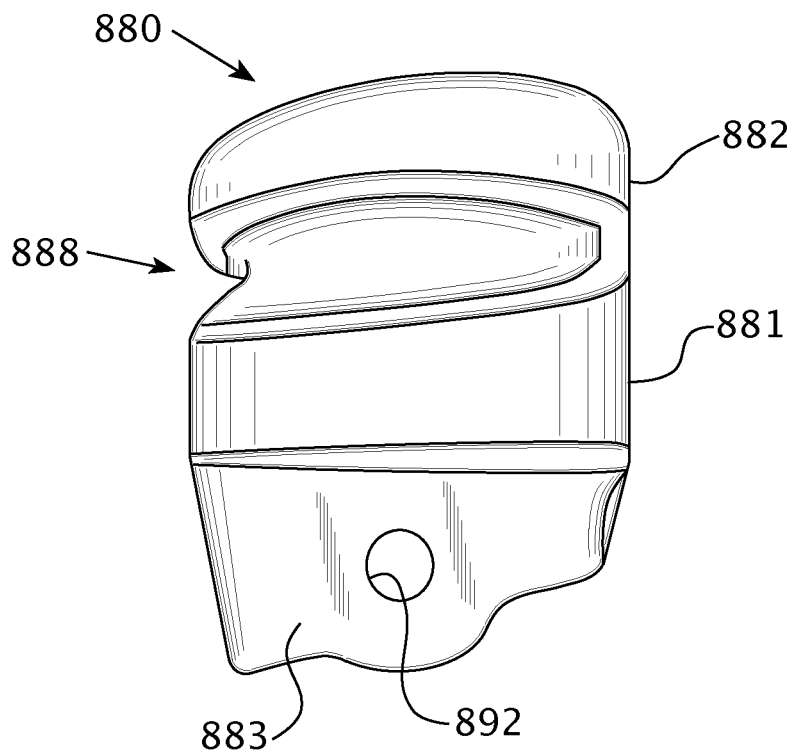
Figure 39D:
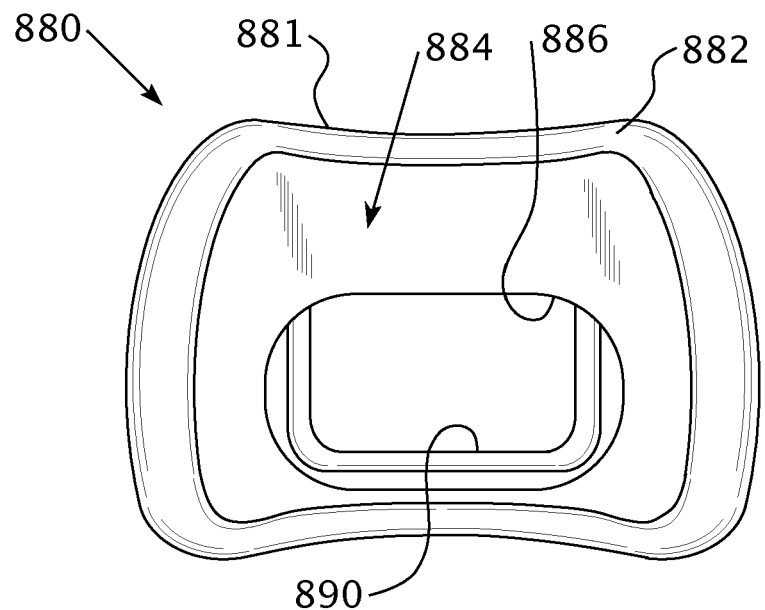

The patient interface device of the present invention is located on the user so that it is mounted on the chin. This is perhaps best shown with reference to FIGS. 36-38, which illustrate an embodiment of a patient interface device 830 (described in greater detail below) mounted on the face of the user. A headgear assembly 100 including straps 54 maintain the patient interface device on the user. The two regions of the patient's face that primarily support the patient interface device on the user are the chin (via the chin support) and the patient's nasal region and/or nasal openings (via the patient interface portion).

The holding force that retains the patient interface device on the user is the headgear force provided by the headgear. This headgear force is depicted as a vector force 900 in FIG. 38. The forces opposing the headgear force include a nasal force 902, i.e., the force at the nasal contact region, and a chin support force 904, i.e., the force at the chin or mandible contact region. A balance of force between the nose and chin is accomplished via a pivoting action about the chin support. An example of a pivot point is indicated by reference number 904. That is, as the strapping force is changed, the patient interface device pivots at point 904 and the nasal interface portion moves about this pivot point as indicated by arrow 908. In other words, the arms of the body portion serve as a moment arm or level arm so that a relatively small headgear strapping force translates into a larger nasal force 902 being needed to counteract the headgear strapping force. The end result is that a tight or effective seal can be created at the nasal region via the nasal interface with a relatively small headgear strapping force.

By providing adjustability in the location where the headgear strapping force is applied to the arm, for example by providing multiple headgear attachment elements 48 (848 in FIG. 38) along the length of the arm, the ratio of nasal force to chin strap for any given headgear force can be controlled. In other words, the headgear attachment locations on the arms define the dimensions d1 and d2. Changing these dimensions, permits adjustment of the ratio of nasal force to chin strap force for any given headgear force. This is primarily accomplished as a result of the pivoting operability and the placement of the headgear attachment locations between the circuit portion and the chin support, i.e., anywhere along the arms 44. Thus, a patient may selectively determine which configuration is most comfortable, providing an opportunity for greater patient compliance for the therapy.

In the illustrated embodiment, patient interface portion 60 includes a nasal cushion 62 having a single opening that seals around the nares of the user. Cushion 62 is attached to circuit portion 50 via a ball-and-socket configuration. In the illustrated exemplary embodiment, the ball portion is provided on an end of circuit portion 50 and a socket is provided in patient interface portion 60.

Cushion 62 can be made from any suitable material, such as gel (see the gel references), silicone, foam, rubber, or combination of materials. Cushion 62 can also be formed from a highly elastic material, such as that disclosed in U.S. patent application Ser. No. 11/266,808, filed Nov. 3, 2005, publication no. 2006/0096598, the contents of which are incorporated herein by reference. The present invention further contemplates that cushion 62 includes one or more flaps provided at a patient contacting portion of the cushion. An example of a cushion having multiple flaps is disclosed in U.S. Pat. No. 4,971,051, the contents of which are incorporated herein by reference. Furthermore, cushion 62 can include other structures, such as ribs, support members, varying wall thickness, and pleats to control the sealing characteristic of the cushion. An example of a cushion having pleats suitable for use in the present invention is disclosed in U.S. Pat. No. 7,237,551 ("the '551 patent), the contents of which are incorporated herein by reference.

An exhaust assembly 64 is defined in patient interface portion 60. In the illustrated embodiment, exhaust assembly 64 is defined by a plurality of vent holes provided in the wall of cushion 62. The number, size, hole pattern, and shape of the holes can have any configuration. One example of a multiple-hole type of exhaust assembly suitable for use in the present invention is disclosed in U.S. Pat. No. 6,851,425 ("the '425 patent"), the contents of which are incorporated herein by reference. It should also be noted that only one exhaust assembly need be provided on the cushion 62, so long as the exhaust flow rate is sufficient to provide an adequate exhaust gas venting function. The exhaust assembly can also be omitted if exhausting gas from the system is not needed or if the exhaust assembly is provided elsewhere, such as in the patient circuit.

FIGS. 5-8 illustrate a second embodiment of a patient interface device 130 according to the principles of the present invention. Patient interface device 130 includes a body portion 140, a circuit portion 150, and a patient interface portion 160. Body portion 140 includes a chin support 142 and a pair of arms 144. In this embodiment, circuit portion 150 is part of, i.e., integral with, the body portion 140. That is, the body portion is a one-piece structure with a passage formed in the body portion that defines a portion of the conduit that carries gas to and from the user. In an exemplary embodiment, the body member is a molded piece. A ball connection 164 is provided at one end of circuit portion 150 to which patient interface portion 160 is selectively coupled. A flexible conduit 152 defining a circuit portion is coupled to the other end of the circuit portion. Any style or variety patient interface portion can be coupled to the body member. Likewise, any style or variety of conduit can be coupled to the body member.

In the illustrated embodiment, patient interface portion 160 includes a nasal cushion 162 that seals around both nares. Cushion 162 has a slightly different configuration from that of cushion 62 shown in FIGS. 1-4. In addition, the exhaust assembly is not provided on the patient interface portion. However, the exhaust assembly can be provided at any location or an different locations, including incorporating it into a coupling between portions of the gas flow path. Finally, a single headgear attachment element 148 is provided on each arm 144 of body portion 140.

FIGS. 9-12 illustrate a third embodiment of a patient interface device 230 according to the principles of the present invention. Patient interface device 230 includes a body portion 240, a circuit portion 250, and a patient interface portion 260. Body portion 240 includes a chin support 242 and a pair of arms 244. In this embodiment, chin support 240 has cup-like configuration rather than a bar or strap that passes under the chin.

A first adjustment assembly 270 is provided to control the angular position of circuit portion 250 and a patient interface portion 260 relative to body portion 240. First adjustment assembly 270 allows the patient interface portion to rotate about a pivot point 272 so that the patient interface portion can be moved toward and away from the user, as indicated by arrow 274. In the illustrated embodiment, this adjustment assembly includes a ratchet-like mechanism that provided discrete positioning of circuit portion 250 relative to body portion 240. The present invention also contemplates a continuous (non-discrete) adjustment mechanism for more freedom in selecting the position of the circuit portion relative to the body portion.

A second adjustment assembly 280, in addition to or in place of the first adjustment assembly, can also provided to control the linear position of circuit portion 250 and a patient interface portion 260 relative to body portion 240. Second adjustment assembly 280 allows the patient interface portion to move up and down in a direction generally parallel to the centerline of the user, as indicated by arrow 282. In this illustrated embodiment, this is accomplished by providing a rotating adjustment member 284 that is fixed in place, and a tube 286 with treading 288 or partial threading on an exposed surface. Tube 286 is disposed in adjustment member 284 so that the threading on the tube engages corresponding threading on the interior surface of the adjustment member. Rotating the adjustment member causes the tube to move up or down relative to the adjustment member to control.

Although not shown, one or more headgear attachment elements can be provided on arms 244, a portion of chin support 242 spaced apart from the pivot point, on circuit portion 250, for example, at location 252, or any combination thereof.

FIGS. 13-16 illustrate a fourth embodiment of a patient interface device 330 according to the principles of the present invention. Patient interface device 330 includes a body portion 340, a circuit portion 350, and a patient interface portion 360. Body portion 340 includes a chin support 342 and a pair of arms 344. A headgear attachment element 348 is provided in each arm.

In this embodiment, circuit portion 350 and body portion 340 are formed as a unitary structure. More specifically, in this embodiment, chin support 342 and a portion of circuit portion 350 is defined by a first piece 370 and the remaining portion of circuit portion 350 is defined by a second piece 372. First and second pieces 370 and 372 mate to form circuit portion 350. Any conventional technique, such as a bonding, welding, mechanical connections, or any combination thereof, can be used to join these two pieces. Of course, the present invention contemplates defining these portions of the patient interface device from more than one piece. For example, first piece 370 or second piece 372, can be formed from multiple pieces that are assembled together.

Circuit portion 350 includes a pair of conduits 352 that are connected or joined together at one end to form a Y-connector configuration. The other ends of conduits 352 are coupled to each side of patient interface portion 360, which in this embodiment, is a nasal cushion 362. In an exemplary embodiment, patient interface portion 360 is rotatably coupled to the ends of conduit 352 so that the nasal cushion can rotate relative to the conduits, as indicated by arrow 354 in FIG. 14. An exhaust assembly (not shown) can be provided in circuit portion 350, a patient interface portion 360, or both.

FIGS. 17-20 illustrate a fifth embodiment of a patient interface device 430 according to the principles of the present invention. Patient interface device 430 includes a body portion 440, a circuit portion 450, and a patient interface portion 460. Body portion 440 includes a chin support 442 and a pair of arms 444. A headgear attachment element 448 is provided in each arm. In this embodiment, patient interface portion 460 is defined by a pair of nasal cushions 462 rather than a single cushion, and circuit portion 450 includes a double swivel that allows rotation in two planes, ninety degrees from one another, as indicated by arrows 452 and 454.

Patient interface portion 460 is also defined by a support member 464 that couples to an end of circuit portion 450 and a cushion assembly 466, which includes nasal cushions 462, that couples to the support member. Support member 464 is more rigid than cushion assembly 466. In an exemplary embodiment, the support member is defined from a plastic, and the cushion assembly is defined by a unitary piece of flexible material, such as silicon. The support member and cushion assembly 466 are coupled together in any suitable fashion using any conventional technique. In one embodiment, these two components are selectively attached so that the cushion assembly can be easily removed and replaced.

In the illustrated embodiment, nasal cushions 462 have a general "mushroom" configuration with a stem portion and a head portion, both of which are formed from a flexible material, such as silicon. Of course, the portions of the prongs can be formed from different materials. For example, the head can be formed of foam or gel and the stem formed from silicon. In addition, the nasal cushions can have a variety of configurations, such as dome-shaped, and can have other features, such as bellows, pleats, and grooves that enable the position, orientation, or angle of the prongs to move or be adjusted to match the anatomical features of the user. Examples of other nasal prongs suitable for use in the sealing assembly of the present invention are described in U.S. Pat. No. 7,856,982, the contents of which are incorporated herein by reference, and in U.S. Pat. No. 7,178,525, the contents of which are incorporated herein by reference.

A swivel connector 456 is coupled to body portion 440 so that the patient circuit that couples the pressure support system can move freely relative to the body portion. This prevents or minimizes torque in the patient circuit from being translated to the body member, which may tend to compromise the seal created by patient interface portion 460. In the illustrated embodiment, swivel connector 456 is defined by a first coupling member 458 that is rotatably coupled to circuit portion 450 and a second coupling member 459 that is rotatably coupled to first coupling member 458. First and second coupling members 458 and 459 are shown as 90° elbows. However, the present invention contemplates that one or both of these coupling members can have other configurations, such as other angles or no angle/bend.

FIGS. 21-24 illustrate a sixth embodiment of a patient interface device 530 according to the principles of the present invention. Patient interface device 530 includes a body portion 540, a circuit portion 550, and a patient interface portion 560. Body portion 540 includes a chin support 542 and a pair of arms 544. In this embodiment, circuit portion 550 is integral with body portion 540 so that both are defined from a unitary structure, such a molded piece. Circuit portion 550 is configured to provide separate supports 552 with a cushion coupling member 554 provided at the end of each support. Nasal cushions 562 are coupled to cushion coupling members 554 in a ball-and-socket configuration, so that the nasal cushion can rotate and move relative to the cushion coupling members. This allows the nasal cushions to move independently to fit a wide variety of users.

Headgear attachment elements 548 are provided on arms 544. In this embodiment, the headgear attachment elements are a track or slot that has multiple, discrete position points along the length of the track. The headgear clip (not shown) connects to the track anywhere along its length and can be moved along the track so that the user can select the optimal location to provide the desired sealing force for the patient interface portion 560 against the nasal region.

FIGS. 25-28 illustrate a seventh embodiment of a patient interface device 630 according to the principles of the present invention. Patient interface device 630 includes a body portion 640, a circuit portion 650, and a patient interface portion 660. Body portion 640 includes a chin support 642, a pair of arms 644, and a circuit coupling portion 646. In this embodiment, circuit portion 650 is defined by a conduit member 651 that selectively attaches to body portion 640 via circuit coupling portion 646.

The present invention contemplates that any technique and configuration can be provided for conduit member 651 and circuit coupling portion 646. In the illustrated exemplary embodiment, conduit member 651 includes separate supports 652 with a cushion coupling member 654 provided at the end of each support. Nasal cushions (not shown) couple to cushion coupling members 654 in a ball-and-socket configuration. Conduit member 651 is a relatively rigid and structure and circuit coupling portion 646 is also a relatively rigid structure that has a configuration that generally matches that of the conduit member. This allows the conduit member to snap together with circuit coupling portion 646 for easy of assembly and replacement. The "Y" shape for conduit member 651 provides a snug fit and controlled positioning for the conduit member relative to the circuit coupling portion.

Figure 29:
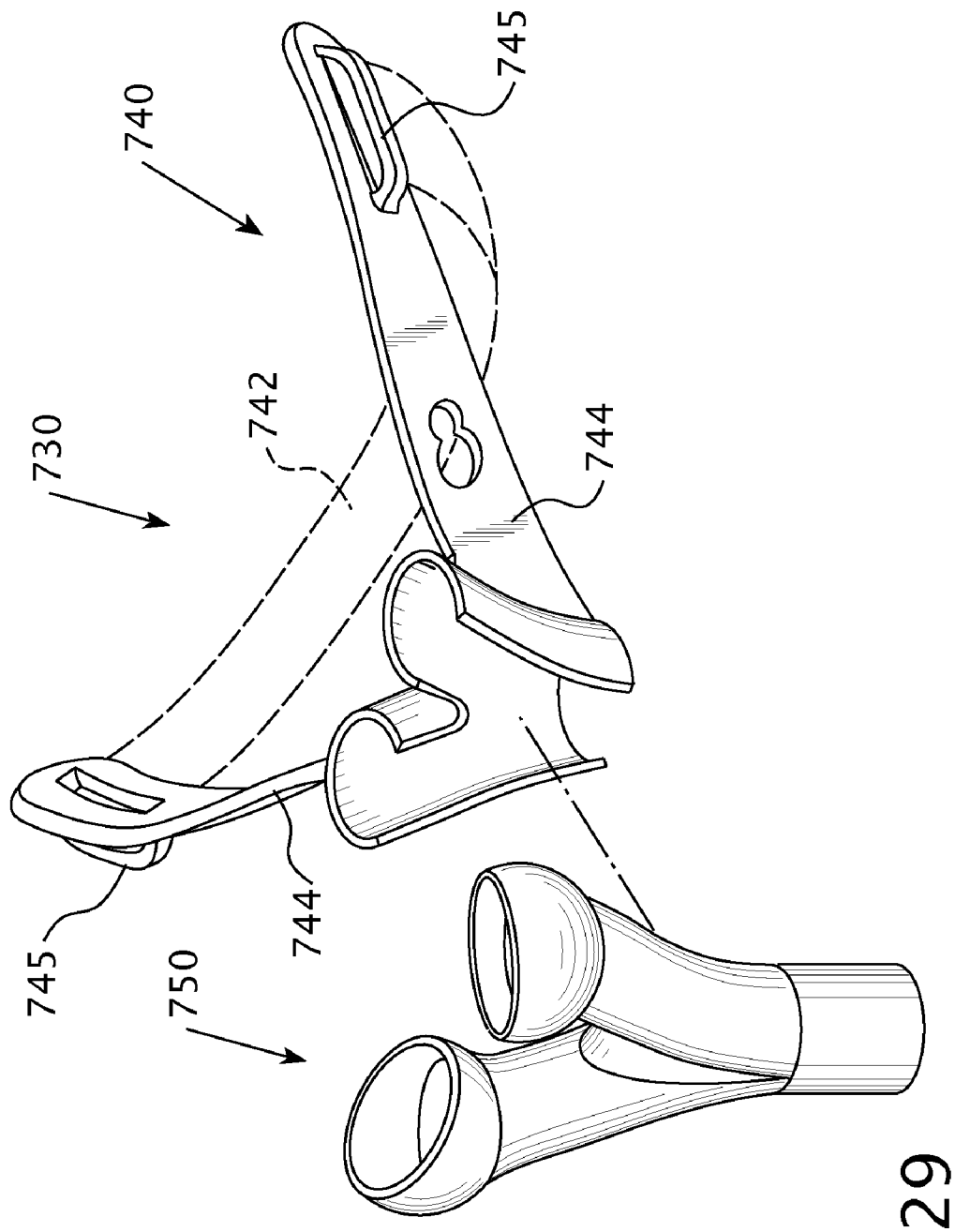
FIG. 29 is an exploded view of a frame and circuit portion according to an eighth embodiment of the present invention.

FIG. 29 illustrates a body portion 740 and a circuit portion 750 of a patient interface device 730 according to an eighth embodiment of the present invention. This patient interface device is generally similar to that of FIGS. 25-28, except for chin support 742. In the previously described embodiments, the chin support portion of the body member is a relatively rigid or semi-rigid structure that spans between the arms of the body member. In this embodiment, however, chin support 742 is a flexible structure, such as a strap or a padded strap, that spans between arms 744. It is believed that making the chin support flexible enhances or facilitates the pivoting action of the patient interface device.

Attachment structures 745 are provided on arms 744 to attach the flexible chin support to the arms. In this embodiment, attachment structures form slots into which the chin strap inserts. It is to be understood that a myriad of other structures, such as snaps, hooks, clips, tabs, pins, and multiple slots, or any combination thereof, can be used to couple chin support 742 to the arms. The present invention also contemplates making the length of chin support 742 adjustable so that the patient interface device can be altered to fit a variety of users. It should also be expressly understood that this flexible chin support configuration can be used in any of the other embodiments of the present invention.

FIGS. 30-38 illustrate a ninth embodiment of a patient interface device 830 according to the principles of the present invention. Patient interface device 830 includes a body portion 840, a circuit portion 850, and a patient interface portion 860. Body portion 840 includes a chin support 842 and a pair of arms 844. In this embodiment, circuit portion 850 and body portion 840 are integral with one another so that a gas flow path is defined through the patient interface device. Arms 844 include multiple headgear attachment elements 848 in the form of slots that are angled to match the angle of attach for the headgear strap 54 when the patient interface device is worn by the user. Attachment structures 845, also in the form of slots, are provided at the ends of arms 844. Chin support 842, which is a flexible strap, inserts through these slots. The present invention contemplates that this chin strap is a padded strap that passes through the attachment structures and loops back on itself. A hook and loop fastener is provided on the strap so that the length of the strap can be adjusted.

Patient interface portion 860 includes a cushion 861 that attaches to circuit portion 850. In the illustrated exemplary embodiment, cushion 861 includes a base 863 and a pair of nasal cushions 862 attached to the base. In this exemplary embodiment, the nasal cushions and the base are formed as a unitary structure. However, the present invention also completes that the nasal cushions be selectively attachable to the base so that different types, sizes, shapes, etc. of nasal cushions can be used. A gas flow passage is defined in the base from the bottom of the base to and through the nasal cushions.

Figure 34:
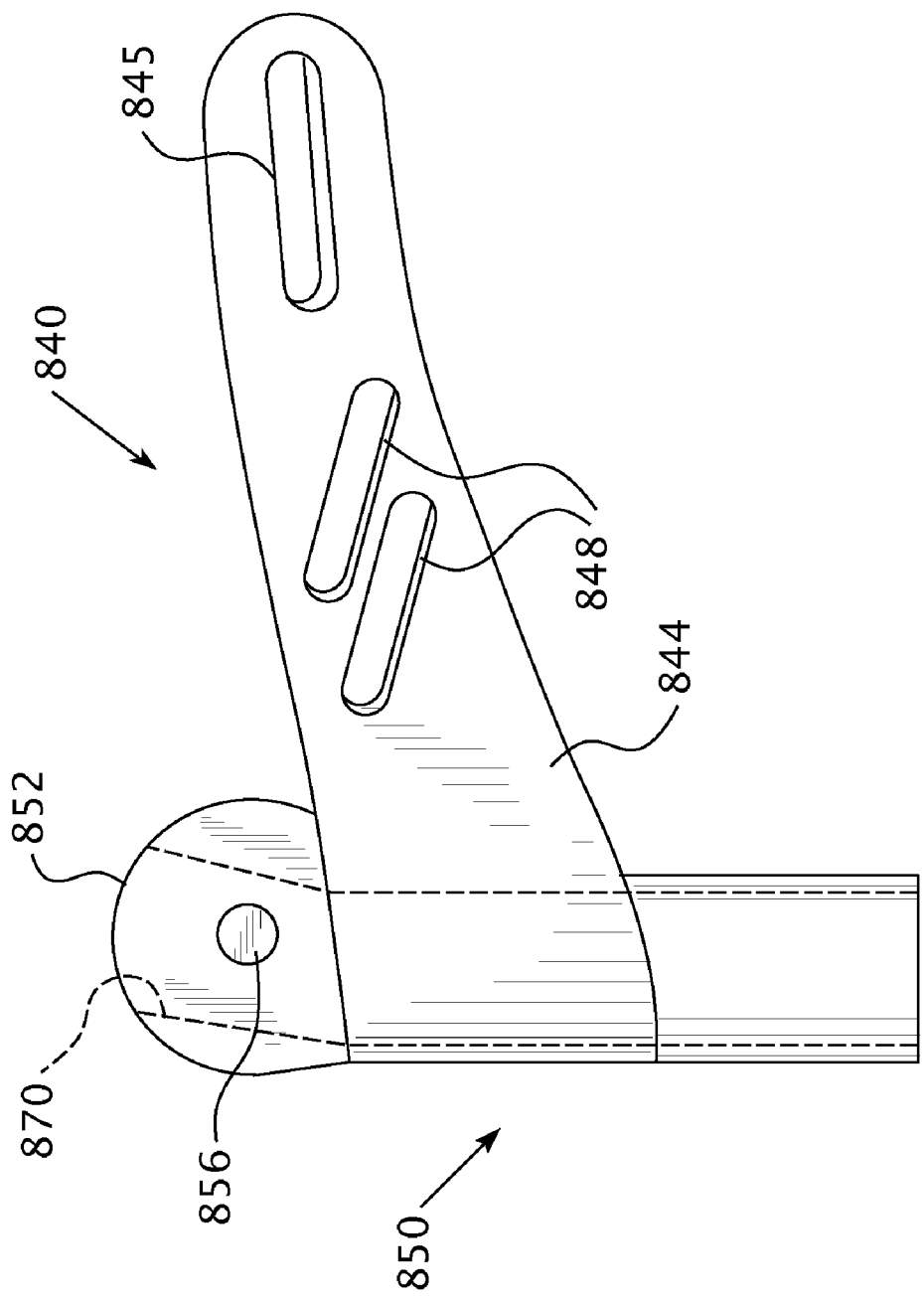
FIGS. 34 and 35 are side and rear perspective views, respectively, of a body portion of the patient interface device of FIG. 30.
Figure 35:
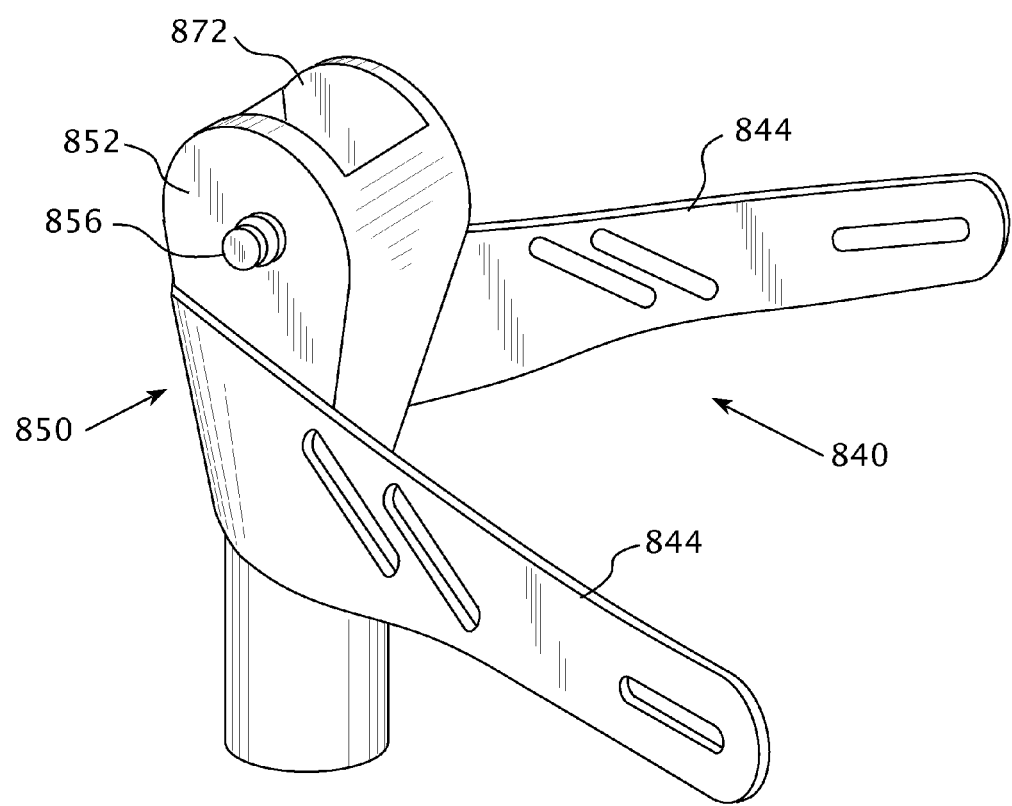

A best shown in FIGS. 34 and 35, circuit portion 850 includes a cushion attachment member 852 to which cushion 861 attaches in a male-female configuration. A cavity is defined in base 863 of cushion 831 having a shape that generally matches the shape of cushion attachment member 852. The cushion attaches to the circuit portion by sliding the base over cushion attachment member 852. The flexibility of the base allows it to flex around the cushion attachment member and the resiliency of the base maintains the attachment.

Figure 33:
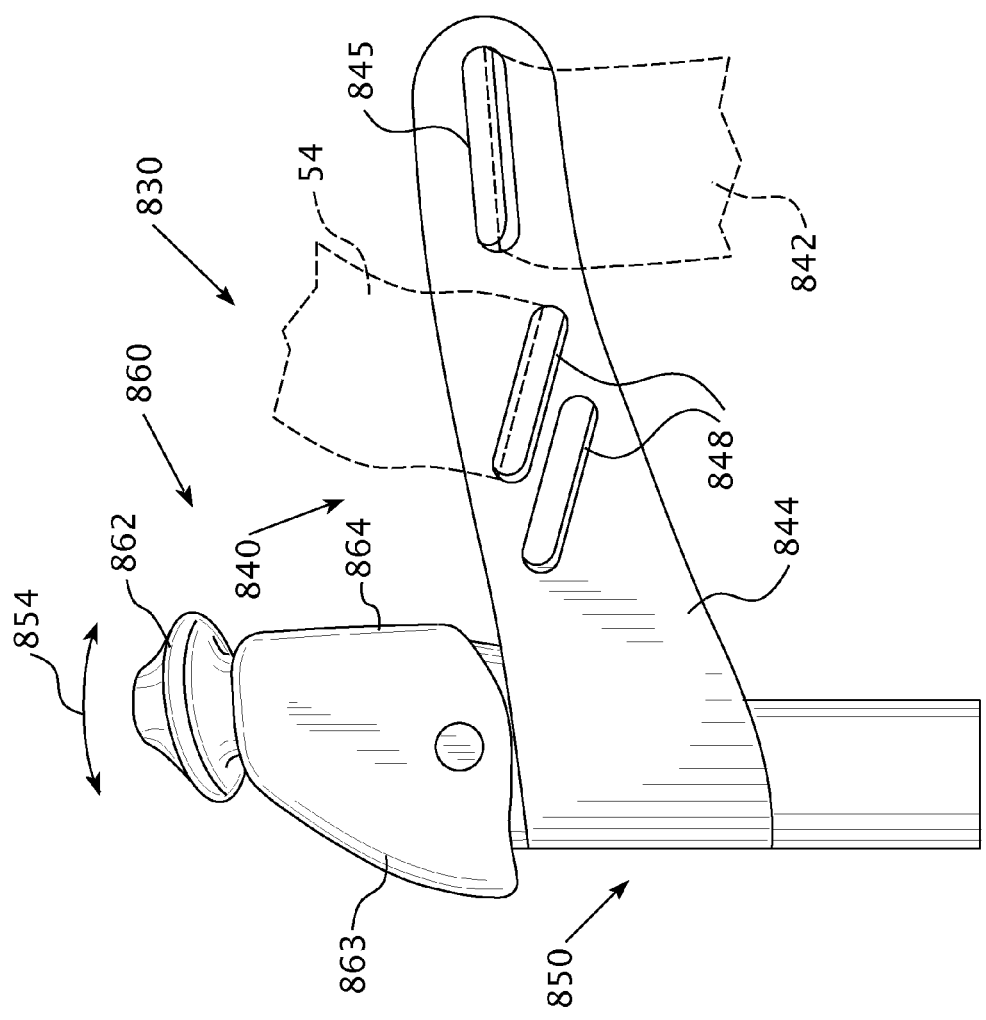

In the illustrated exemplary embodiment, cushion attachment member 852 has a barrel shape (and the cavity in the cushion has a similar barrel shape) so that the cushion can be moved or rotated relative to body member 830 as indicated by arrow 854 in FIG. 33. The barrel shape, unlike a ball-and-socket, allows movement (rotation) in only one plane. Optional pins 856 can be provided on the sides (ends) of the barrel to help maintain the attachment between the cushion and the cushion attachment member 852 and allow the user to rotate the cushion about a fixed point and without dislodging it from the cushion attachment member. A passage 870 is defined through circuit portion 850, including through cushion attachment member 852. An opening 872 is defined in the side of the cushion attachment member so that gas flows between circuit portion 850 and cushion 861.

FIGS. 39A-39D are front perspective, front, side, and top views, respectively, of an alternative embodiment of a patient interface portion 880 suitable for use in the patient interface device of FIGS. 30-38. In other words, patient interface portion 880 can be used in place of patient interface portion 860 in the patient interface device of FIGS. 30-38. Patient interface portion 880 is a nasal cushion type of interface, somewhat similar to nasal cushions 62, 162, 362 of the previous embodiments. Patient interface portion 880 includes a unitary or single-piece cushion 881 that attaches to circuit portion 850. In the illustrated exemplary embodiment, cushion 881 includes a base 883 and a nasal interface portion 882 attached to the base. The present invention contemplates that cushion 881 is formed from a material that provides a sufficient amount of support for base 883 and while providing relative flexibility for nasal interface portion 882. In an exemplary embodiment, the cushion is formed from silicone, with the base portion being thicker than the nasal interface portion to provide the different degrees of support/flexibility for each portion.

In this exemplary embodiment, nasal interface portion 882 includes a patient contacting surface 884 that is contoured to generally correspond to the underside of the human nose. An opening 886 is provided in surface 884 and sized such that both of the user's nares are covered by the opening so that a flow of gas is communicated to both the nares via the opening. A pleat or groove 888 is also defined in the cushion between nasal interface portion 882 and base portion 883. Groove 888 allows nasal interface portion 882 to move so that its can adjust to fit/seal a variety of different types of faces and noses.

In the illustrated embodiment, groove 888 is defined around the front and sides of the nasal cushion, but is not provided in the back, i.e., the side of the cushion that faces the user when the patient interface device is being worn. The present invention, contemplates, however, providing the groove around the entire perimeter of the cushion. The present invention also contemplates providing multiple grooves in the cushion, and providing one or more grooves in other locations on the cushion. In addition the groove or grooves can have different sizes, shapes, and configurations. The '026 application teaches a mask having grooves and/or various groove configurations suitable for use in this embodiment of the present invention.

An opening 890 is provided in base portion 883 to communicate the interior of the nasal cushion with the patient circuit portion of the patient interface device. In addition, openings or receptacles 892 are provided in the sides of the nasal cushion to receive pins 856 of the cushion attachment member of the circuit portion.

Figure 40:
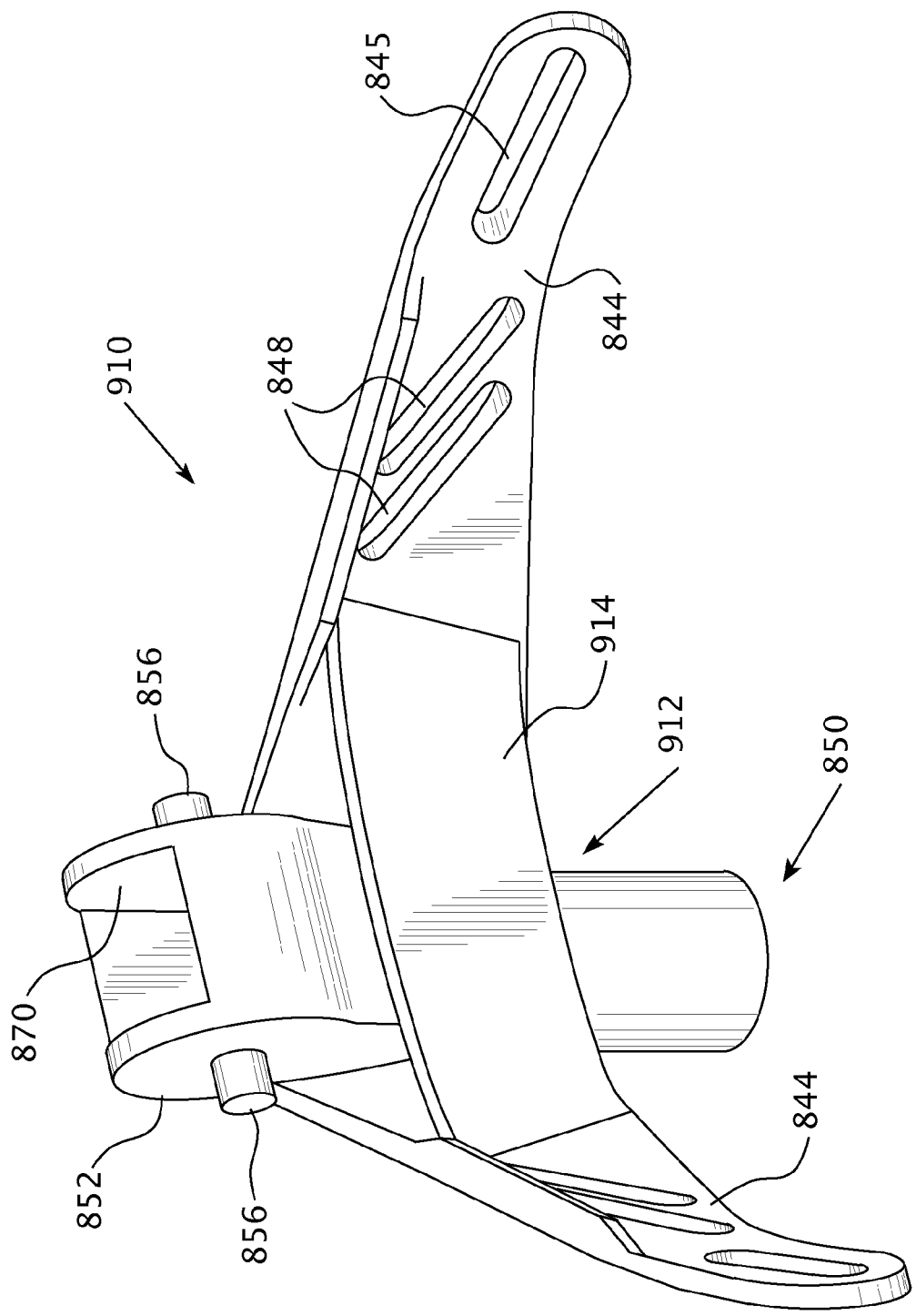
FIG. 40 is a rear perspective view of an alternative embodiment for the body portion of the patient interface device of FIG. 30.

FIG. 40 is a rear perspective view of an alternative embodiment for a body portion 910 the patient interface device of FIG. 30-38. As in the previous embodiment, the body portion includes a pair or arms 844 that attach to a circuit portion 850. In this embodiment, however, the body portion includes an oral member 912 adapted to cover the mouth. One purpose for covering the mouth is to seal the lips closed so that mouthing breathing or leakage of gas through the mouth during the pressure support therapy is minimized.

In the exemplary embodiment illustrated in FIG. 40, oral member 912 is a flexible or semi-rigid strap 914 that extends between the pair of arms 844. Strap 914 is positioned sized and configured such that it overlies and presses against the lips of the user when the patient interface device is donned by the user. The present invention contemplates that strap 914 can have a variety of other sizes, shapes, and configurations so long as the purpose of sealing the mouth and/or lips of the user is achieved. Strap 914 is connected to arms 844 in any suitable manner. In an exemplar embodiment, strap 914 is adjustable so that the length of the strap, and, hence, the force against the mouth/lips of the user can be controlled. In addition, the present invention contemplates providing multiple attachments points along the length of arms 844 so that the relative position of the strap on the arms can be adjusted. This, in effect, allows the position of the strap relative to the user to be controlled.

Figure 30:
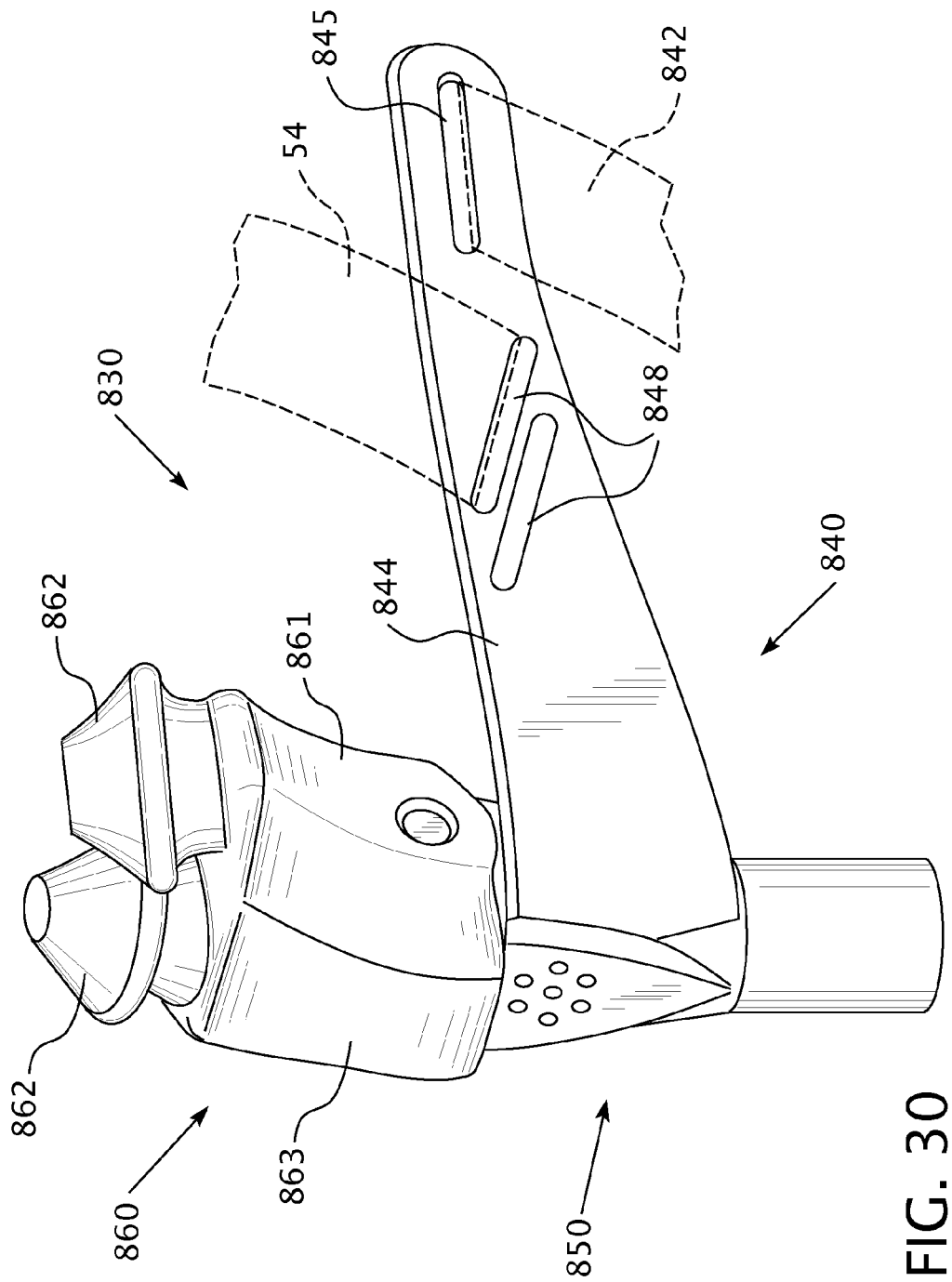
FIG. 30 is a front perspective view of a ninth embodiment of a patient interface device according to the principles of the present invention.
Figure 31:
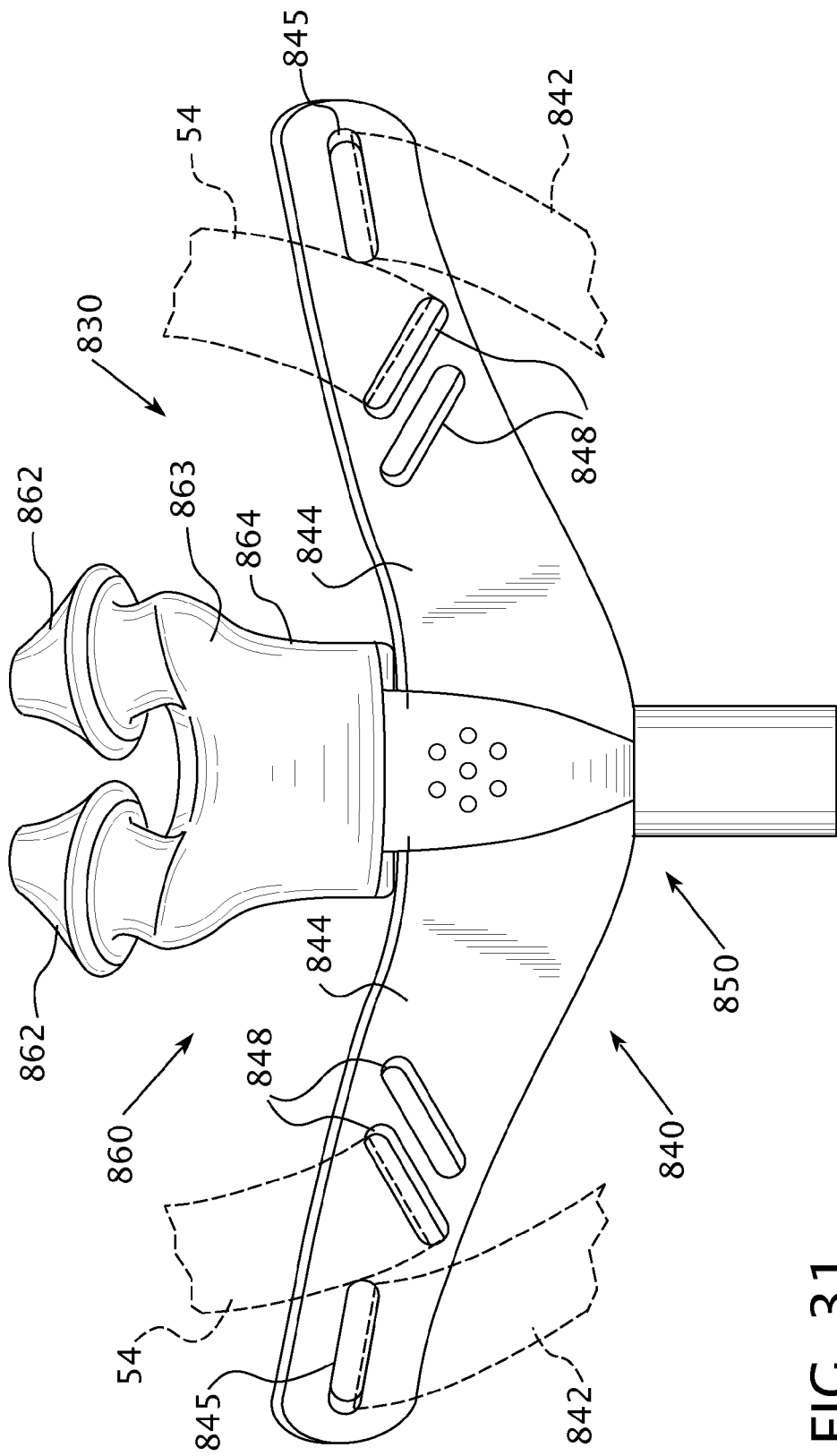
FIGS. 31-33 are front, rear, and side views, respectively, of the patient interface device of FIG. 30.
Figure 32:
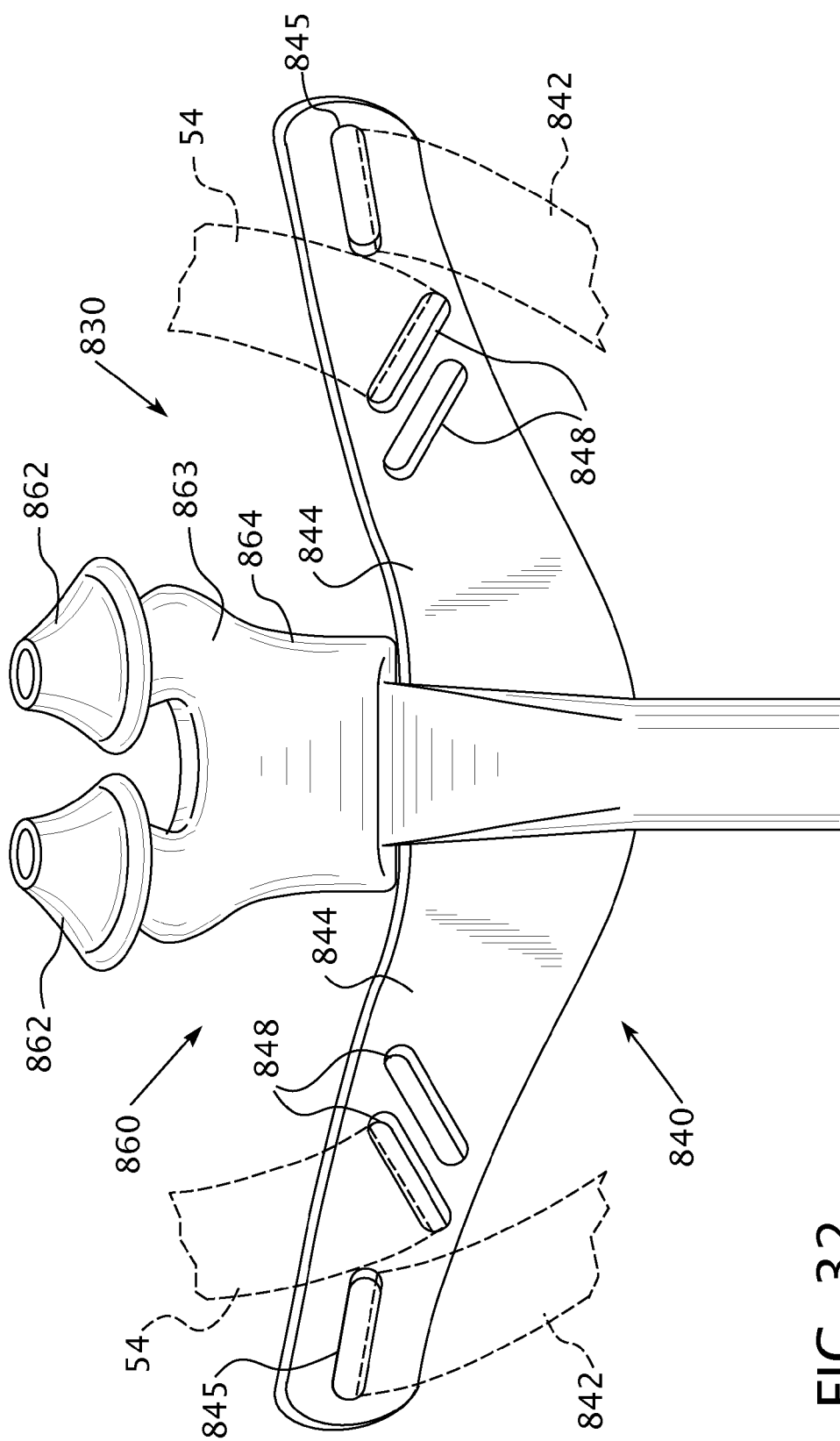
Figure 41A:
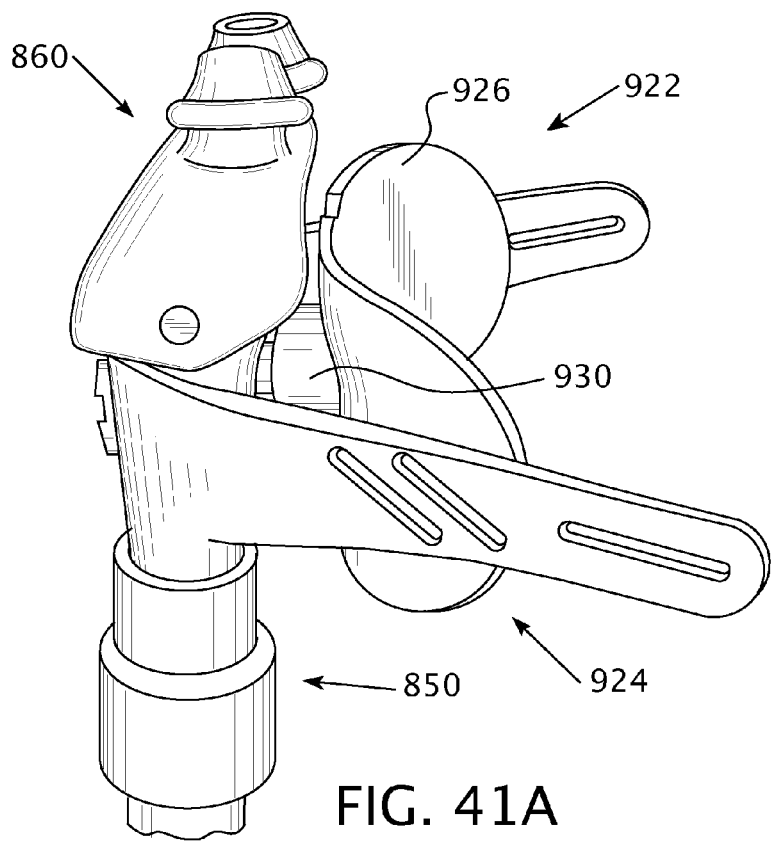
FIGS. 41A and 41B are side perspective and rear views, respectively, of yet another alternative embodiment for the body portion of the patient interface device of FIG. 30.
Figure 41B:
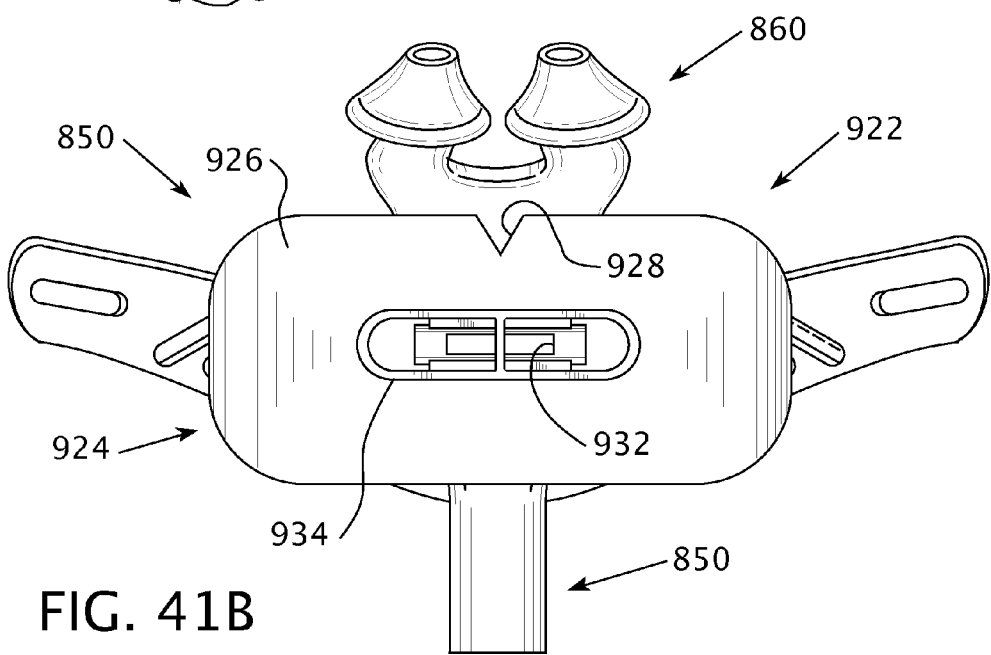
Figure 42:
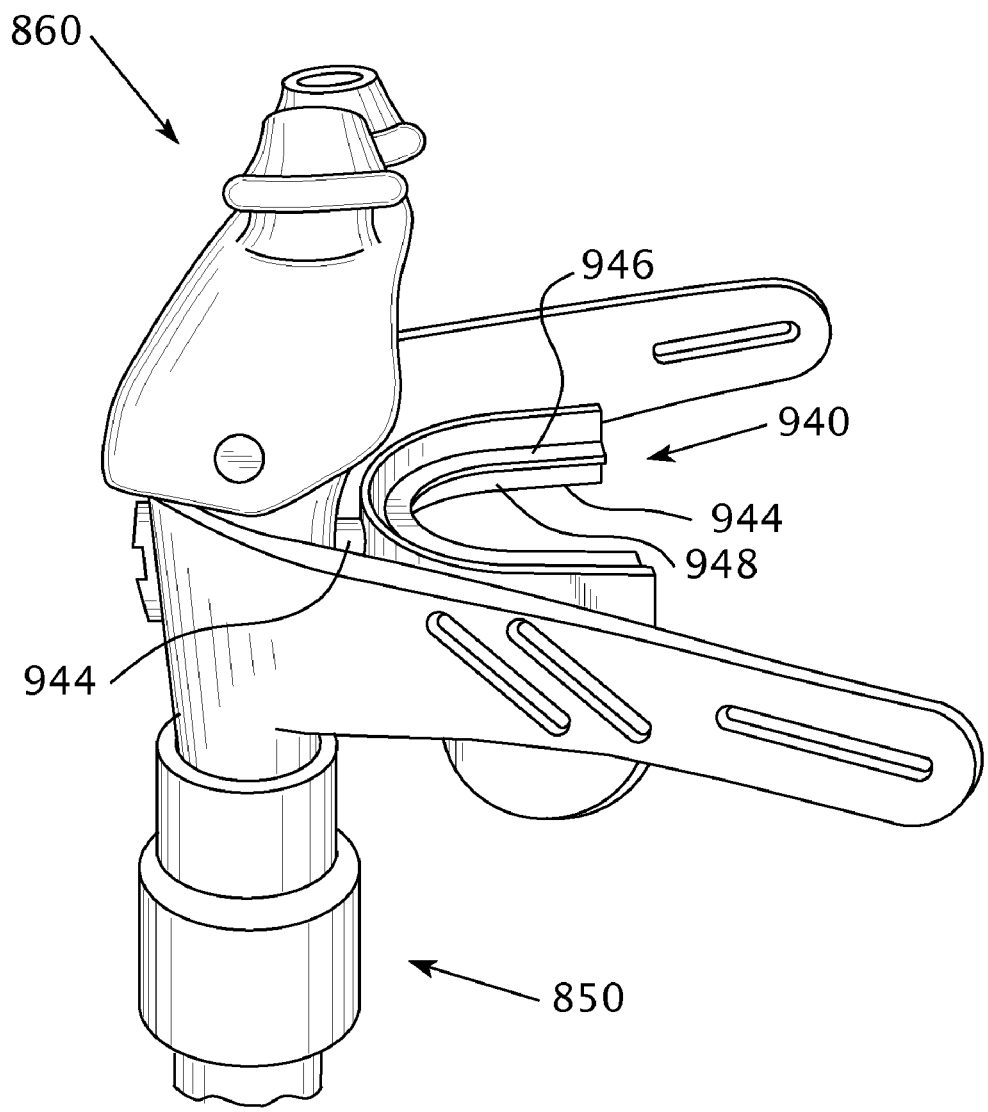
FIG. 42 is a side perspective view of a still further alternative embodiment for the body portion of the patient interface device of FIG. 30.

FIGS. 41A-42 illustrate other alternative embodiments for the body portion of patient interface device of FIG. 30. More specifically, FIGS. 41A and 41B show a first alternative configuration for the oral member. In this embodiment, oral member 922 includes a lip sealing assembly 924 that is operatively coupled to circuit portion 850 of the patient interface device. Lip sealing assembly 924 can also be coupled to one or both of the pair of arms 844.

In the illustrated exemplary embodiment, lip sealing assembly 924 includes a seal 926 that inserts into the mouth behind the lips and in front of the teeth. Seal 926 is formed from a flexible material so that it can bend to fit the user's mouth. It can also be formed from a stiff material that is capable of being molded to fit the user's mouth. The seal can also be trimmed, bent, or otherwise reconfigured to fit the user. Notches 928 or other shape controlling mechanisms can be provided on the perimeter of or at other locations on the seal to facilitate bending or altering of the shape of the seal.

Seal 926 is coupled to circuit portion 850 via a connecting member 930. In this embodiment connecting member 930 includes a passage 932 that communicates with the passage defined in the circuit portion 850 so that a flow of gas is provided to the user's mouth in addition to the flow of gas provided to the user's nose via patient interface portion 860. Connecting member 930 can be rigid or flexible and can be permanently or selectively attachable to the circuit portion or the seal. Making the connecting member and the seal selectively attachable to one another and making the connecting member selectively attachable to the circuit portion allows a high degree of flexibility for the user in selecting the right size connecting member and seal for their mouth and face. The present invention also contemplates that the length of connecting member 930 can be adjustable, for example, by providing a threaded connection to the circuit portion or by making the connecting member telescoping, so that the user can move the connecting member to fit them.

As best shown in FIG. 41B, the present invention contemplates providing a tooth contacting member 934 that fits between the user's teeth. Tooth contacting member 934 serves as a bite block to prevent the user from completely closing his or her mouth. This allows gas to flow between, rather than through, the teeth. Tooth contacting member 934 can have a variety of different configurations. In the illustrated embodiment, it is merely an oval shaped tube that inserts between the teeth and extends a short distance beyond the teeth into the oral cavity.

FIG. 42 shows alternative configuration for an oral member 940 that helps appreciate the variety of different configurations that are possible for the oral member. In this embodiment, oral member 940 includes a bite block 942 that is attached to circuit portion 850 via a connecting member 944. Connecting member 944 is a rigid or flexible attachment to the circuit portion, and does not include a gas flow passage. Thus, bite block 942 helps secure the patient interface device to the user, and does not provide a gas flow to the user's mouth.

Bite block 942 has an upper portion or upper tray 946 and a lower portion or lower tray 948. Upper tray 946 engages the upper teeth and lower tray 948 engages the lower teeth. Upper and lower trays 946, 948 can be formed from an suitable material. In a further embodiment, these trays are configured to hold a tooth engaging material so that the bite block can be customized to the user's dentition.

In this embodiment, the upper and lower trays are formed as a unitary structure. The present invention also contemplates forming each separately. In which case, the upper and lower trays can be moveable relatively to one another to control the position of the mandible. The trays can be also be adjustable relatively to one another so that the user or caregiver can select the position that accomplishes whatever function is desired. For example, the trays can be set to a position that achieve maximum comfort for that particular user. The trays can also be set to move the mandible from its normal position, which is done, for example, to treat snoring and/or OSA.

In the illustrated embodiment, the upper and lower trays are also generally aligned with one another so that the user's upper and lower teeth mesh in a normal, mouth closed fashion. The present invention also contemplates offsetting the upper and lower trays from one another. For example, the lower tray can be set forward of the upper tray so that the user's mandible is advanced from its normal resting position. This is done, as noted above, to keep the airway open to treat OSA.

Figure 43:
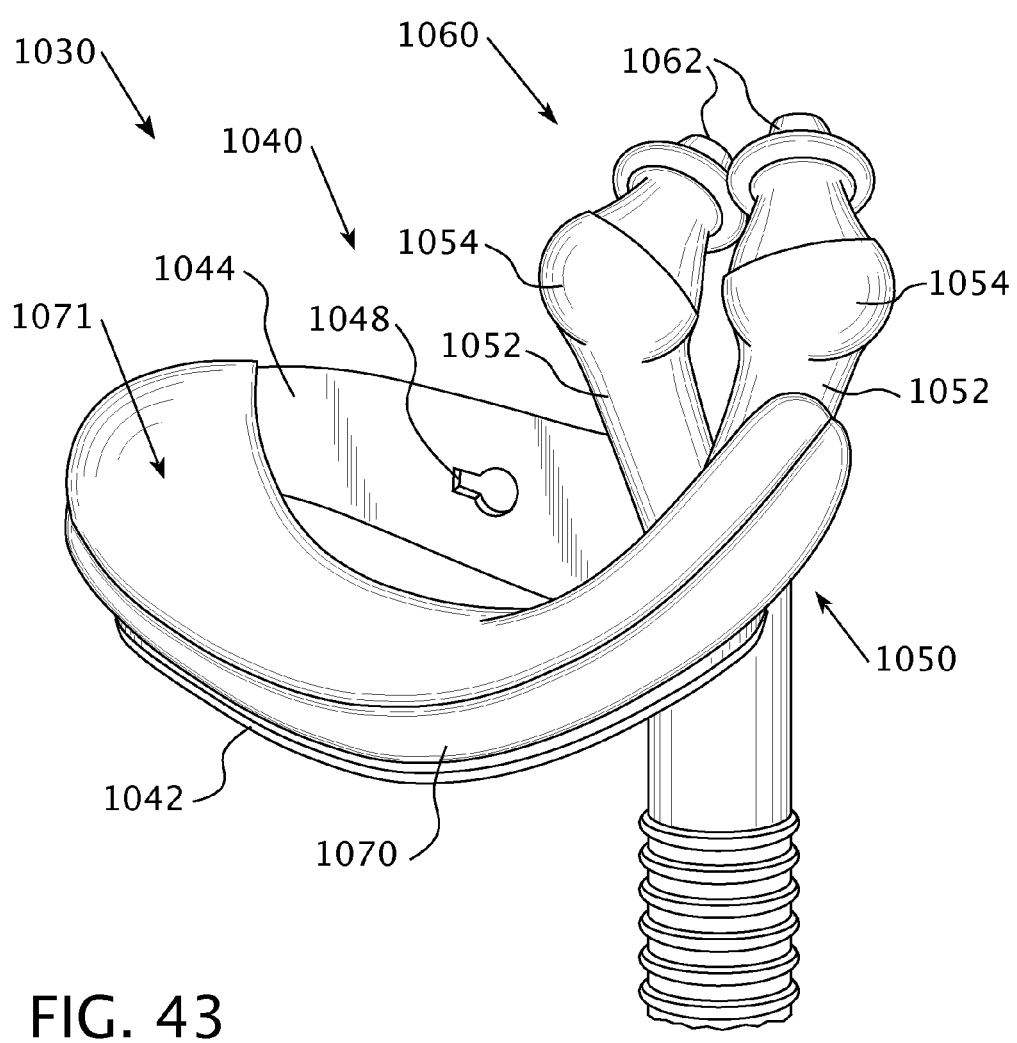
FIG. 43 is a rear perspective view of a tenth embodiment of a patient interface device according to the principles of the present invention.
Figure 44:
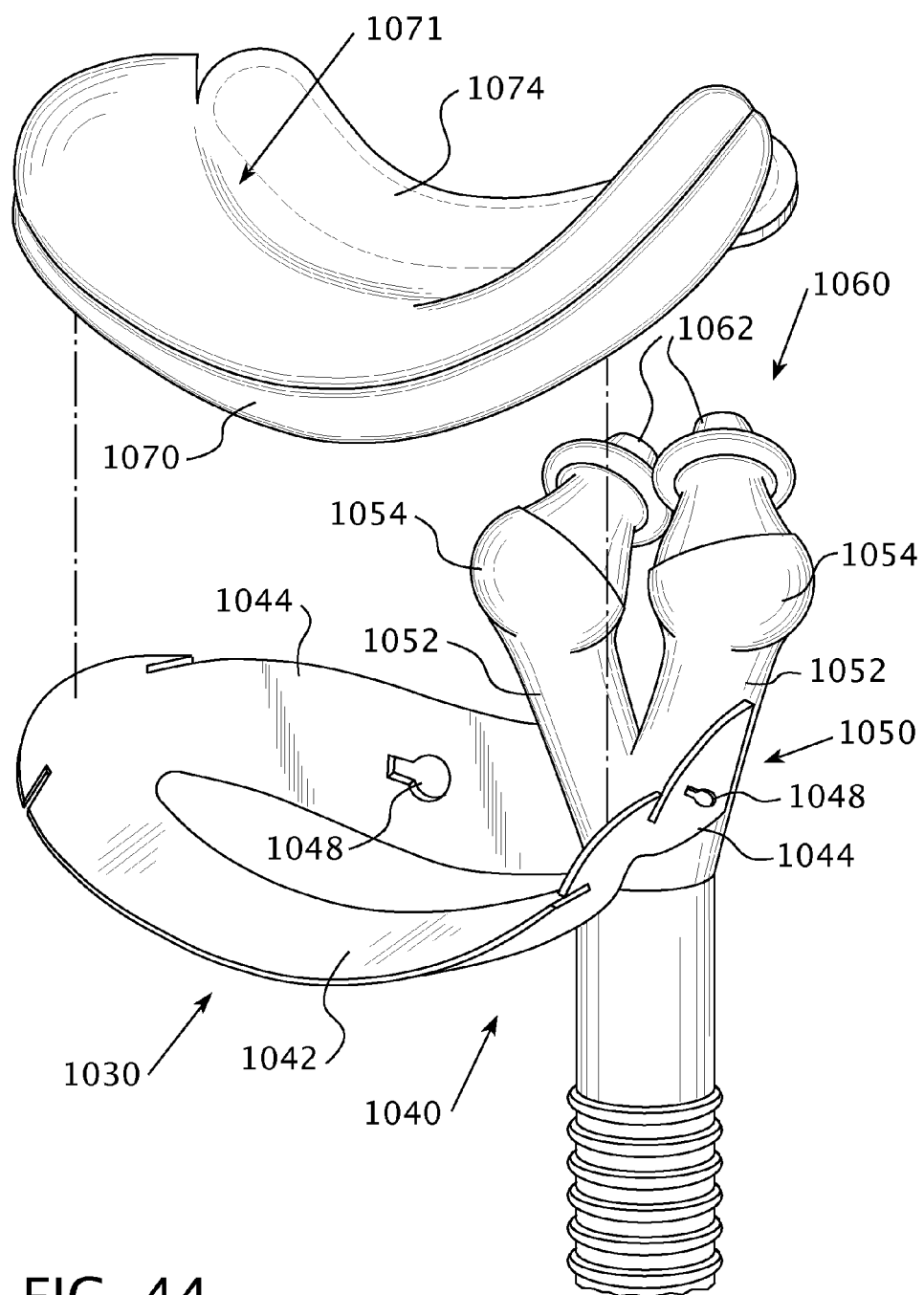
FIG. 44 is partially exploded view of the patient interface device of FIG. 41.
Figure 45:
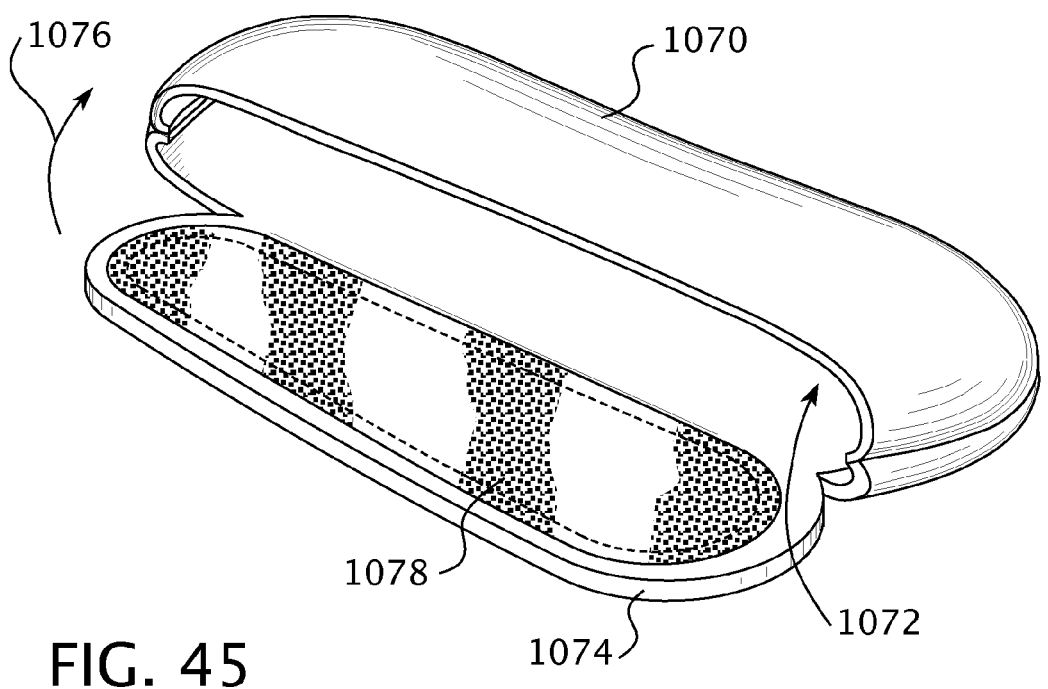
FIG. 45 is a perspective view of a pad suitable for use with the patient interface device of FIG. 43.

FIGS. 43-45 illustrate a tenth embodiment of a patient interface device 1030 according to the principles of the present invention. Patient interface device 1030 includes a body portion 1040, a circuit portion 1050, and a patient interface portion 1060. Body portion 1040 includes a chin support 1042 and a pair of arms 1044. Patient interface device 1030 is generally similar to patient interface device 530 of FIGS. 21-24 in that circuit portion 1050 is integral with body portion 1040 so that both are define a unitary structure, i.e., a single molded part. Circuit portion 1050 is configured to provide separate supports 1052 with a cushion coupling member 1054 provided at the end of each support. Nasal cushions or prongs 1062 are coupled to cushion coupling members 1054 in a ball-and-socket configuration, so that the nasal cushion can rotate and move relative to the cushion coupling members and independent of one another.

Headgear attachment elements 1048 are provided on arms 1044. In this embodiment, the headgear attachment elements are keyed slots that enable a headgear clip (not shown) to connect to the arms. In this embodiment, chin support 1042 is a relative rigid or semi-rigid structure supporting a chin pad 1070. In this embodiment, chin pad 1070 is selectively attachable to chin support 1042 and covers a majority of the chin support when so attached. A surface 1071 of the pad serves as the patient contact portion. The preset invention contemplates that surface 1071 can be made from the same material as the rest of the chin support or it can be made from other materials suitable for use in contacting a patient, especially for an extended period of time, such as a gel, foam, or other soft material.

To enable chin pad 1070 to selectively attach to chin support 1042, the illustrated embodiment of the present invention includes providing a pocket 1072 in the chin pad into which the chin support, or a portion thereof, inserts. A flap 1074 is coupled to the main portion of the chin pad and folds over, as indicated by arrow 1076 to close the pocket trapping the chin support in the pocket, thus securing the chin pad to the chin support. The flap is secured to the chin pad via an attachment mechanism 1078, which can be any conventional type of fastener. For example, attachment mechanism 1078 is as a hook and loop faster, such as VELCRO®, where the hooks are provided on flap 1074 and the softer loops are provided on the pad. Slots 1080 can be provided on the arms 1044 and/or chin support 1042 to secure or help secure the chin pad to the chin support. This embodiment is advantageous because, for example, it allows the chin pad to be easily removed and replaced or cleaned.

Figure 46:
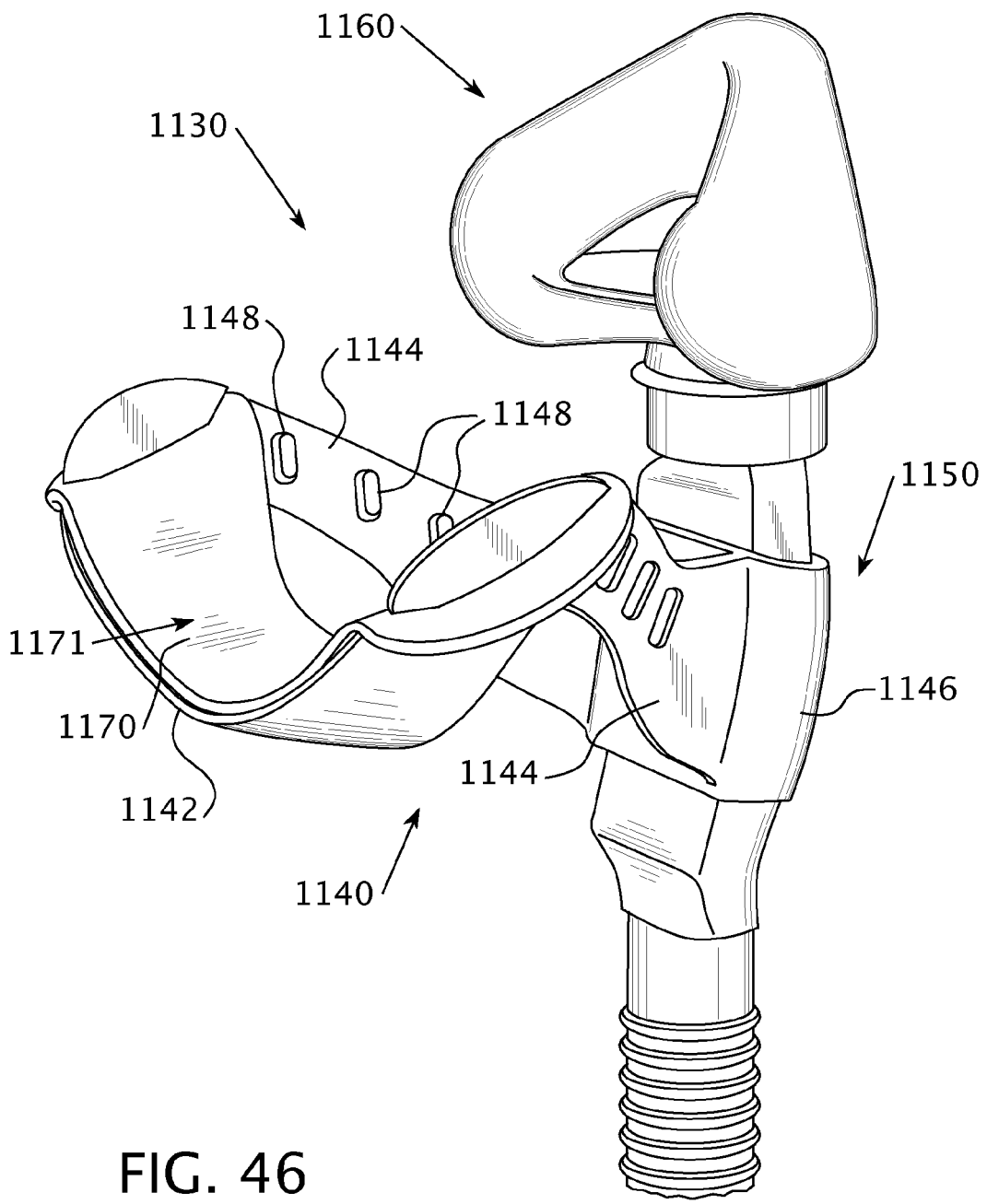
FIG. 46 is a rear perspective view of an eleventh embodiment of a patient interface device according to the principles of the present invention.
Figure 47:
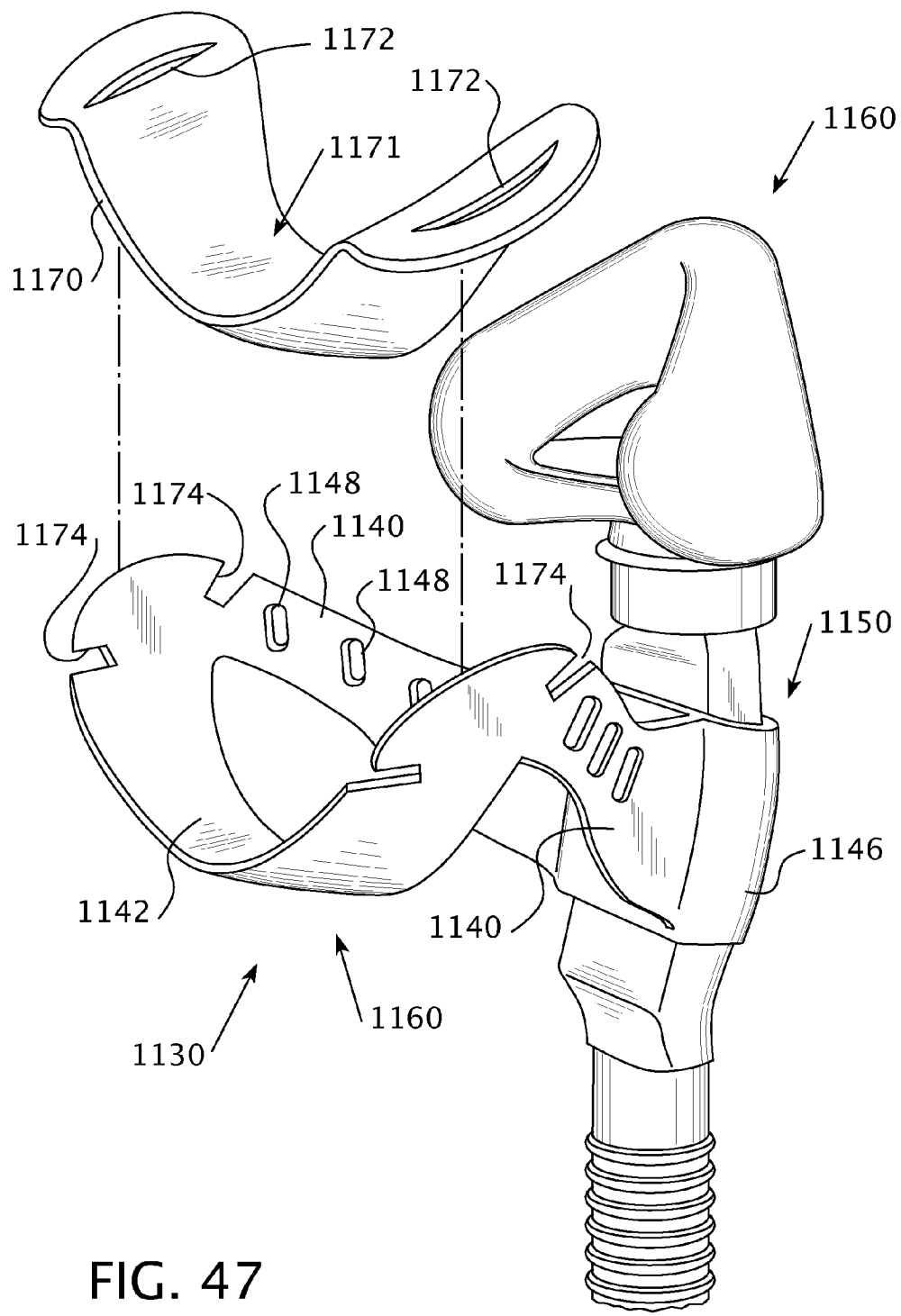
FIG. 47 is a partially exploded view of the patient interface device of FIG. 43.

FIGS. 46 and 47 illustrate an eleventh embodiment of a patient interface device 1130 according to the principles of the present invention. Patient interface device 1130 includes a body portion 1140, a circuit portion 1150, and a patient interface portion 1160. Body portion 1140 includes a chin support 1142, a pair of arms 1144, and a circuit coupling portion 1146 that is couple to the arms. Patient interface device 1130 is generally similar to patient interface device 30 of FIGS. 1-4 in that circuit portion circuit coupling portion 1146 is coupled to the arms and couples a circuit portion 1150 to the body portion. In this embodiment, circuit coupling portion 1146 is integral with arms 1144 so that they define a unitary structure, i.e., as a single molded piece or part. In addition, patient interface portion 1160, as illustrated, is generally similar to patient interface portion 60. Of course, the present invention contemplates that any suitable patient interface portion can be used in patient interface device 1130, including for example, a pair of nasal prongs.

Headgear attachment elements 1148 are provided on arms 1144. In this embodiment, the headgear attachment elements are slots provided in arms 1144. The headgear straps can be connected direction to these slots or they can be connected to the slots via a headgear clip (not shown). In this embodiment, chin support 1142 is a relative rigid or semi-rigid structure supporting a chin pad 1170. Chin pad 1170 is selectively attachable to chin support 1142 and covers a majority of the chin support when so attached. A surface 1171 of the pad serves as the patient contact portion. The preset invention contemplates that surface 1171 can be made from the same material as the rest of the chin support or it can be made from other materials suitable for use in contacting a patient, especially for an extended period of time, such as a gel, foam, or other soft material.

To enable chin pad 1170 to selectively attach to chin support 1142, the illustrated embodiment of the present invention includes slots 1172 in the chin pad. These slots receive the end portions of the chin support, the end portions of the arms, or both. Slots 1174 are provided on arms 1144 and/or chin support 1142 to secure or help secure the chin pad to the chin support. This embodiment is advantageous because, for example, it allows the chin pad to be easily removed and replaced or cleaned. It should be understood that the chin pad can have a variety of different configurations, sizes, shapes, and be made from a variety of materials or combinations of materials.

Figure 48:
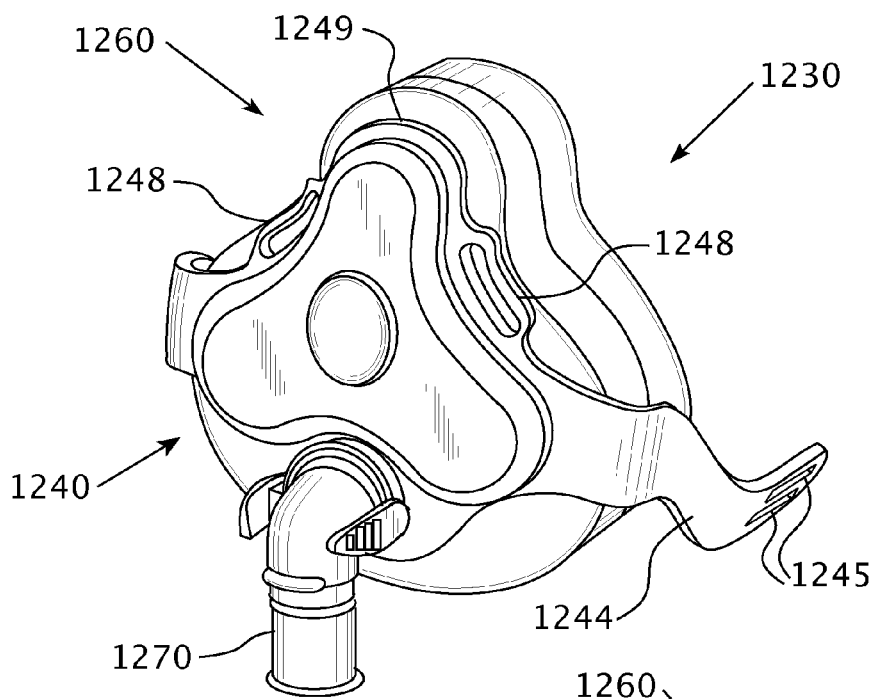
FIG. 48 is a front perspective view of a twelfth embodiment of a patient interface device according to the principles of the present invention.
Figure 49:
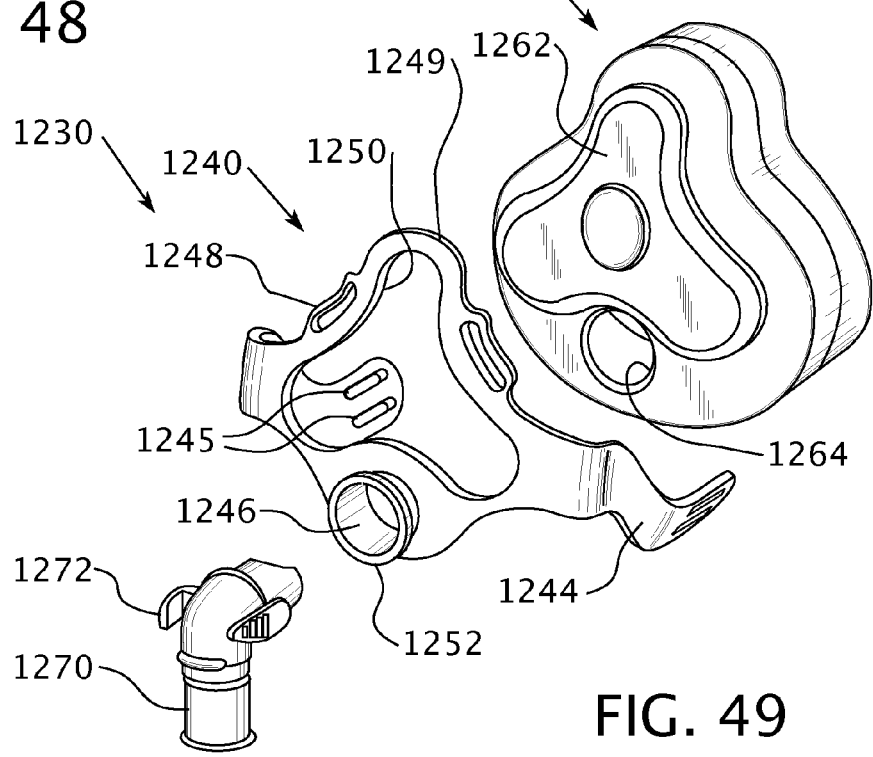
FIG. 49 is an exploded view of the patient interface device of FIG. 46.
Figure 50:
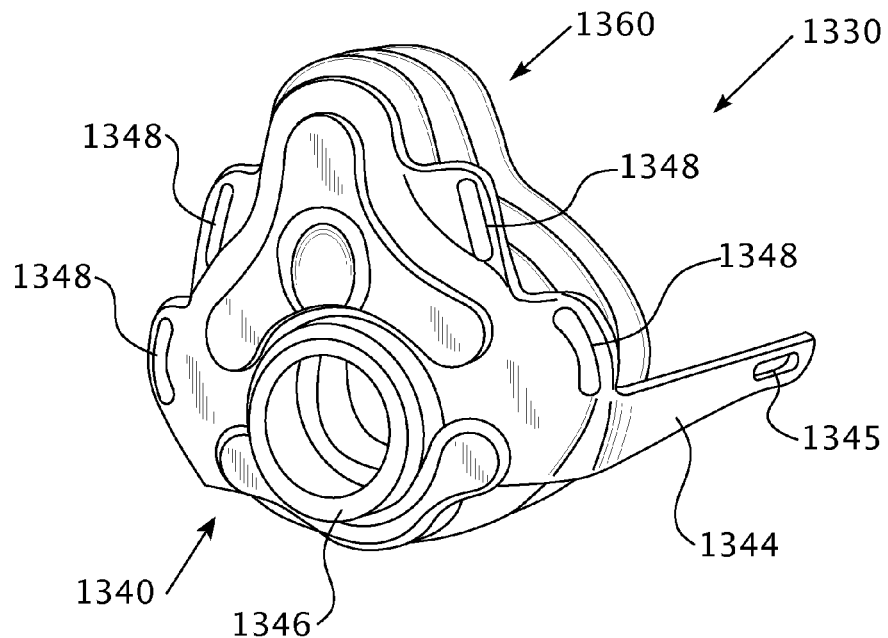
FIG. 50 is a front perspective view of a thirteenth embodiment of a patient interface device according to the principles of the present invention.
Figure 51:
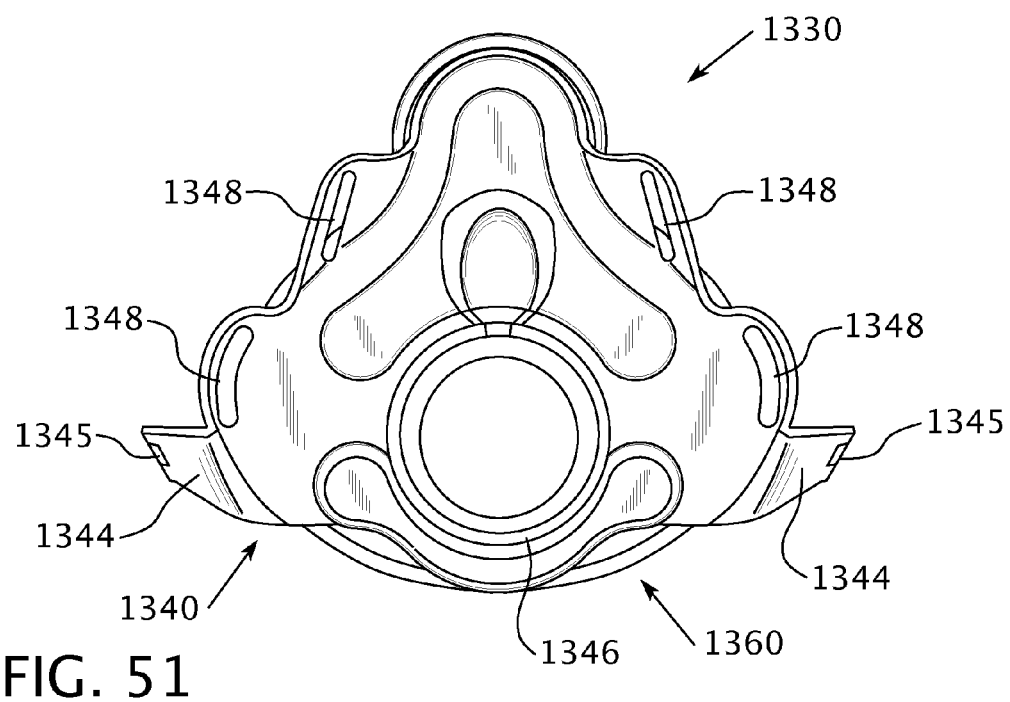
FIGS. 51 and 52 are front and bottom views, respectively, of the patient interface device of FIG. 50.
Figure 52:
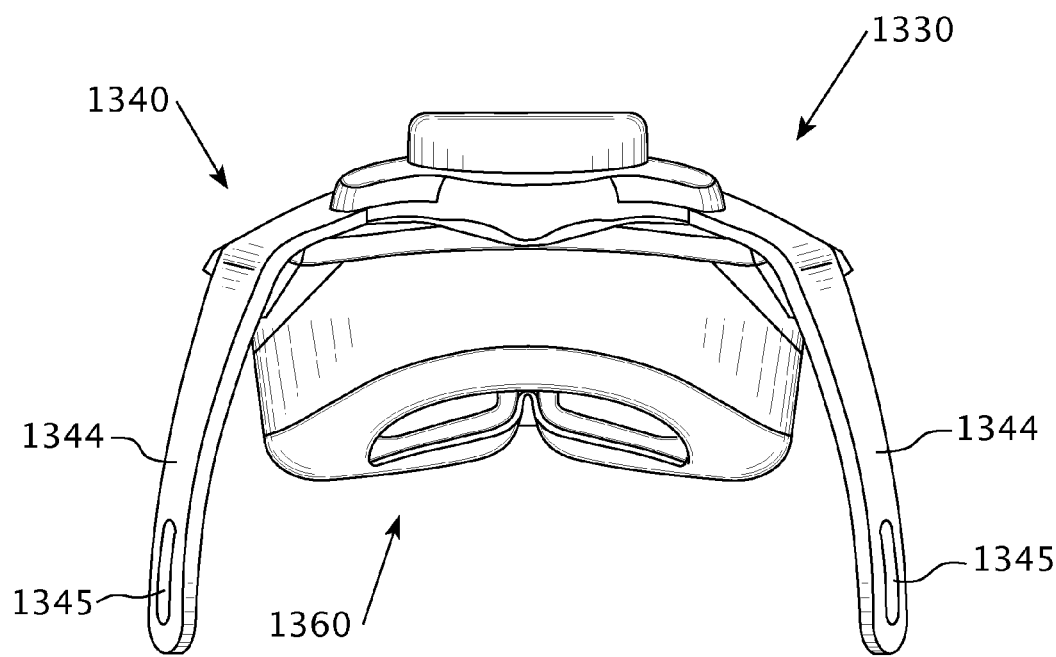
Figure 53:
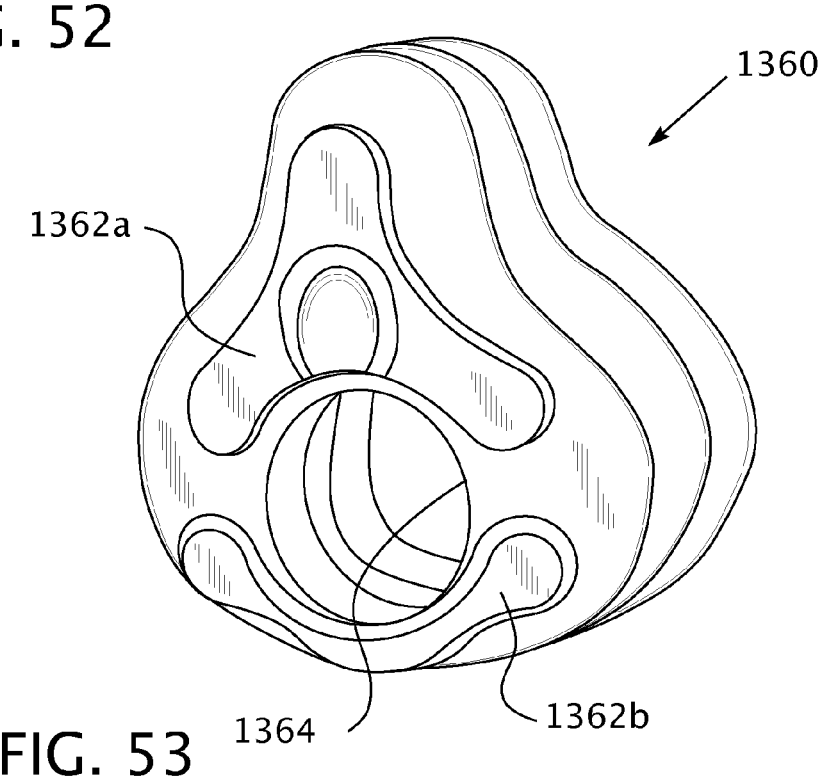
FIG. 53 is a front perspective view a patient interface portion of the patient interface device of FIG. 48.
Figure 54:
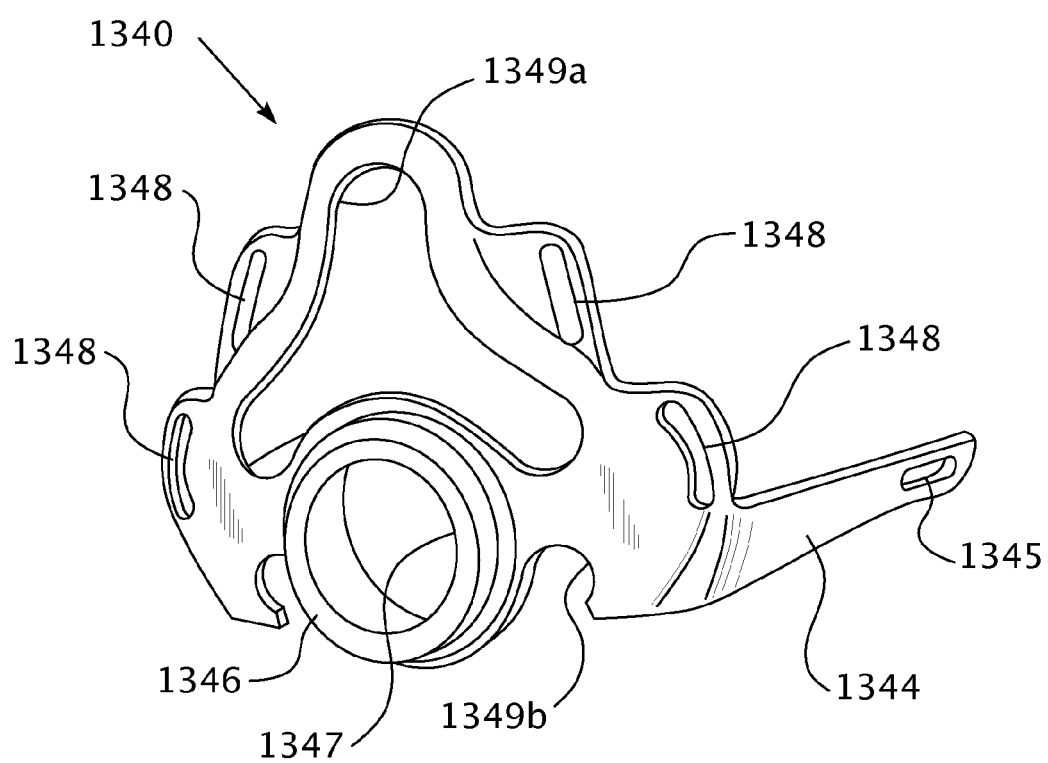
FIG. 54 is a front perspective view a body portion of the patient interface device of FIG. 50.

FIGS. 48 and 49 illustrate a twelfth embodiment of a patient interface device 1230 according to the principles of the present invention. Patient interface device 1230 includes a body portion 1240 and a patient interface portion 1260. Body portion 1240 includes a chin support (not shown), a pair of arms 1244, and a circuit coupling portion 1246 that is coupled to the arms. In this embodiment, circuit coupling portion 1246 defines or serves as the circuit portion of the patient interface device. Patient interface device 1230 in this embodiment provides a full face type of patient interface that covers both the user's nasal passages and mouth.

Attachment structures 1245 are provided on arms 1244 to couple the chin support to the body portion. In the illustrated embodiment, attachment structures 1245 include a pair of slots provided in each arm. The chin support can be coupled to one or both to these slots. Providing multiple slots gives the user greater flexibility in configuring the patient interface device to suit his or her particular facial features.

Headgear attachment elements 1248 are also provided on body portion 1240 so that headgear straps (not shown) can be coupled to the body portion. In this embodiment, attachment elements 1248 are provided in the form of slots provided, not on arms 1244, but an a central portion 1249 of the body member. It should be noted that the location of attachment elements 1248 still enables the arms of the body portion to serve as a moment arm or level arm, so that a relatively small headgear strapping force applied to attachment elements 1248 translates into a larger nasal force being needed to counteract the headgear strapping force, thereby providing a tight or effective seal of patient interface portion 1260 against the surface of the user with a relatively small headgear strapping force.

Patient interface portion 1260 is coupled to central portion 1249 of body portion 1240 such that arms 1244 extend beyond the sides of the patient interface portion toward the user. To facilitate the attachment of the patient interface portion to the body portion, the body portion includes an opening 1250 and the patient interface portion includes a protrusion 1262. Protrusion 1262 is sized and configured to fit snugly into opening 1250, and both are configured such that the patient interface portion is assembled with the body portion, there is little or no movement, such as rotation of the these components relative to one another.

Circuit coupling portion 1246 provides a connection to a patient circuit coupling 1270 so that a flow of gas can be communicated between a patient circuit (not shown) and the interior of patient interface portion 1260. An opening 1264 is provided in patient interface portion 1260 and an opening is provided in circuit coupling portion 1246 to define a gas flow path through the patient interface device. In the illustrated exemplary embodiment, patient circuit coupling 1270 is an elbow coupling that rotatably and releasably attaches to circuit coupling portion 1246. To provide the releasably attachment of the patient circuit coupling to the circuit coupling portion of the body member, patient circuit coupling 1270 includes a pair of clamps 1272 that engage a rim 1252 on circuit coupling portion 1246. Squeezing the claims together releases a free end of the arms defining the clamps from the rim so that the patient circuit coupling can be detached from the circuit coupling portion.

Although not shown, the present invention contemplates providing an entrainment valve and/or exhaust assembly on patient circuit coupling 1270. Example of suitable entrainment valves and exhaust assemblies are disclosed in the '425 patent. Of course the exhaust assemble can be provided at other locations, such as in the patient interface portion, the body member, or in any combination of locations. The patient interface portion can also include one or more pleats or grooves, and can include one or more flaps at the patient contacting side.

FIGS. 50-54 illustrate a thirteenth embodiment of a patient interface device 1330 according to the principles of the present invention. Patient interface device 1330 includes a body portion 1340 and a patient interface portion 1360. Body portion 1340 includes a chin support (not shown), a pair of arms 1344, and a circuit coupling portion 1346 that is coupled to the pair of arms. As in the previous embodiment, circuit coupling portion 1346 defines or serves as the circuit portion of the body portion of the patient interface device. Attachment structures 1345 are provided on arms 1344 to couple the chin support to the body portion. Patient interface device 1330 is generally similar to patient interface device 1230 of FIGS. 48 and 49 in that it is also a full-face type of nasal interface, covering both the nares and mouth. This embodiment is provided mainly to illustrate further possible variations that can be provided in the features that make up the patient interface device.

In this embodiment, for example, body portion 1340 includes a pair of attachment elements 1348 to attach to headgear straps (not shown). The present invention contemplates that only one pair of these attachment structures will be used to couple the headgear to the patient interface device. Providing multiple pairs gives the user freedom and flexibility in selecting the par of attachment structures for attaching the headgear to the mask that is best suited, e.g., most comfortable, stable, and/or minimizes unintentional leakages, for that user.

Body portion 1340 includes a pair of opening or cavities 1349a and 1349b adapted to receive corresponding protrusions 1362a and 1362b of patient interface portion 1340. As in the previous embodiment, these features are provided to facilitate the attachment of the patient interface portion to the body portion. When assembled, there is little or no movement, such as rotation or sliding, of the body portion relative to the patient interface portion.

Circuit coupling portion 1346 provides a connection to a patient circuit coupling, such as that shown in the other figures, so that a flow of gas can be communicated between a patient circuit and the interior of patient interface portion 1360. An opening 1364 is provided in patient interface portion 1360 and a corresponding opening 1347 is provided in circuit coupling portion 1346 to define a gas flow path through the patient interface device. In this embodiment, a portion of circuit coupling portion 1346 extends from the body member and provides a mounting surface for the patient interface portion. More specifically, opening 1364 fits over circuit coupling portion 1346 to connect the portions of the patient interface device together to provide a gas flow path into and out of the patient interface portion.

Figure 55:
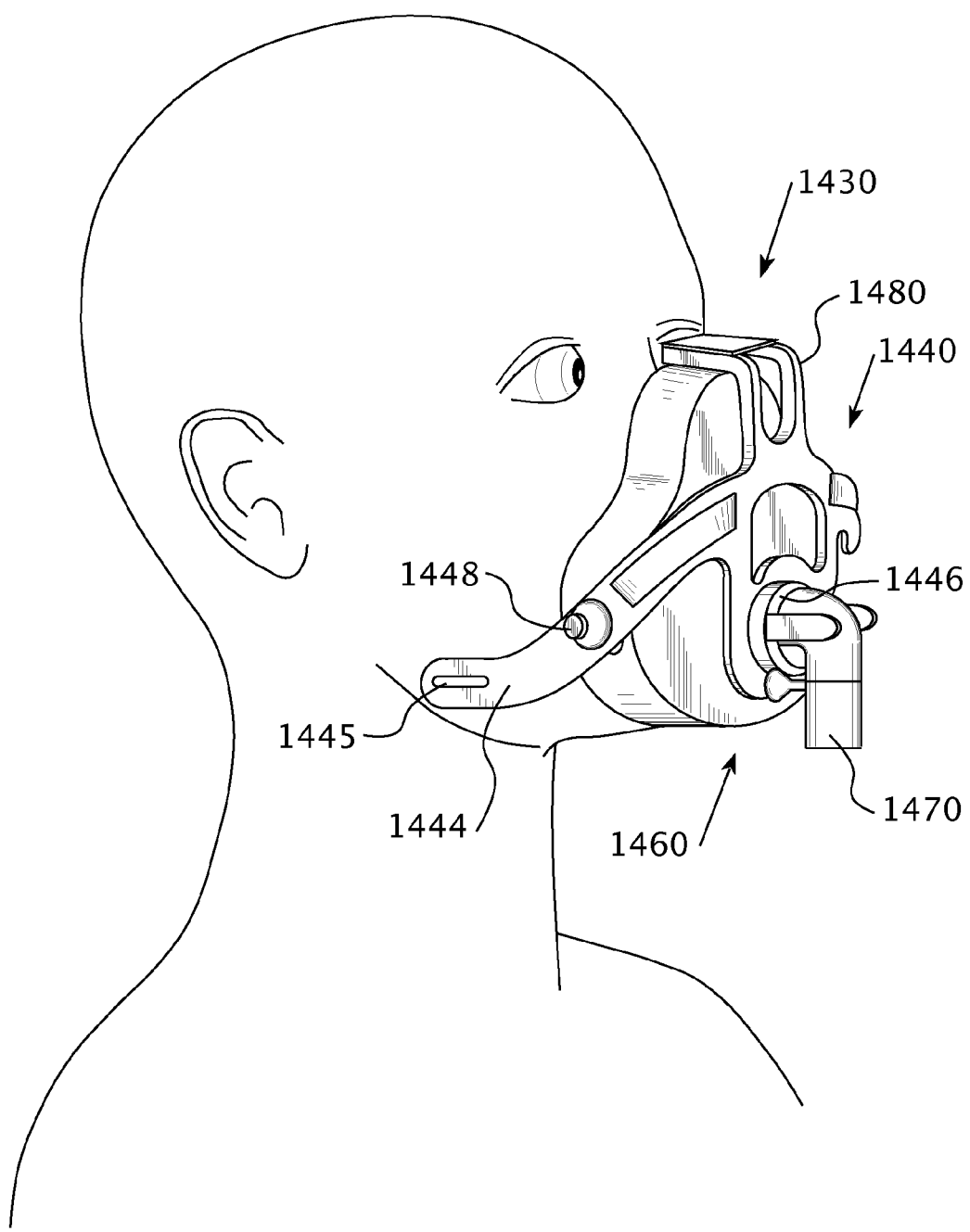
FIGS. 55-57 are side perspective, bottom perspective, and front views, respectively of a fourteenth embodiment of a patient interface device according to the principles of the present invention.
Figure 56:
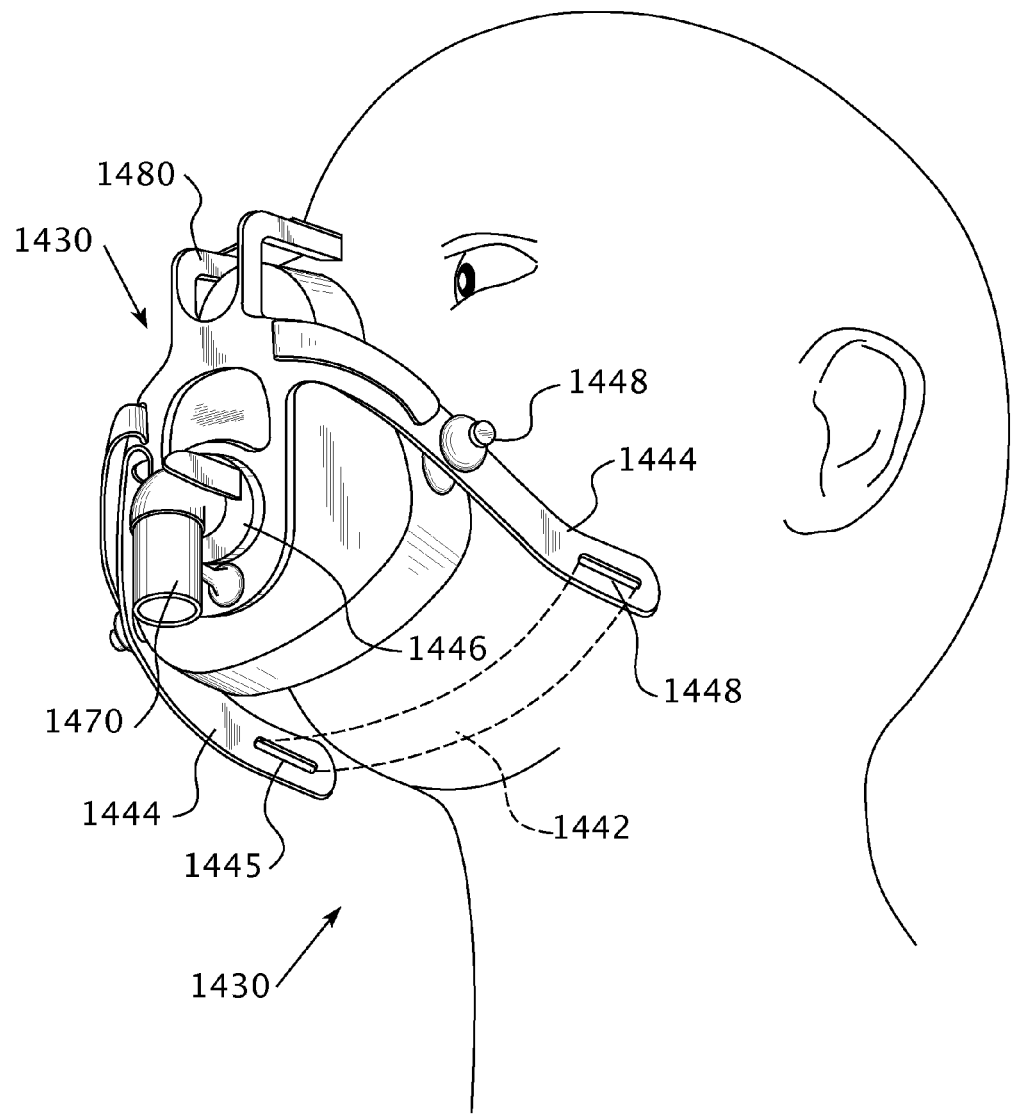
Figure 57:
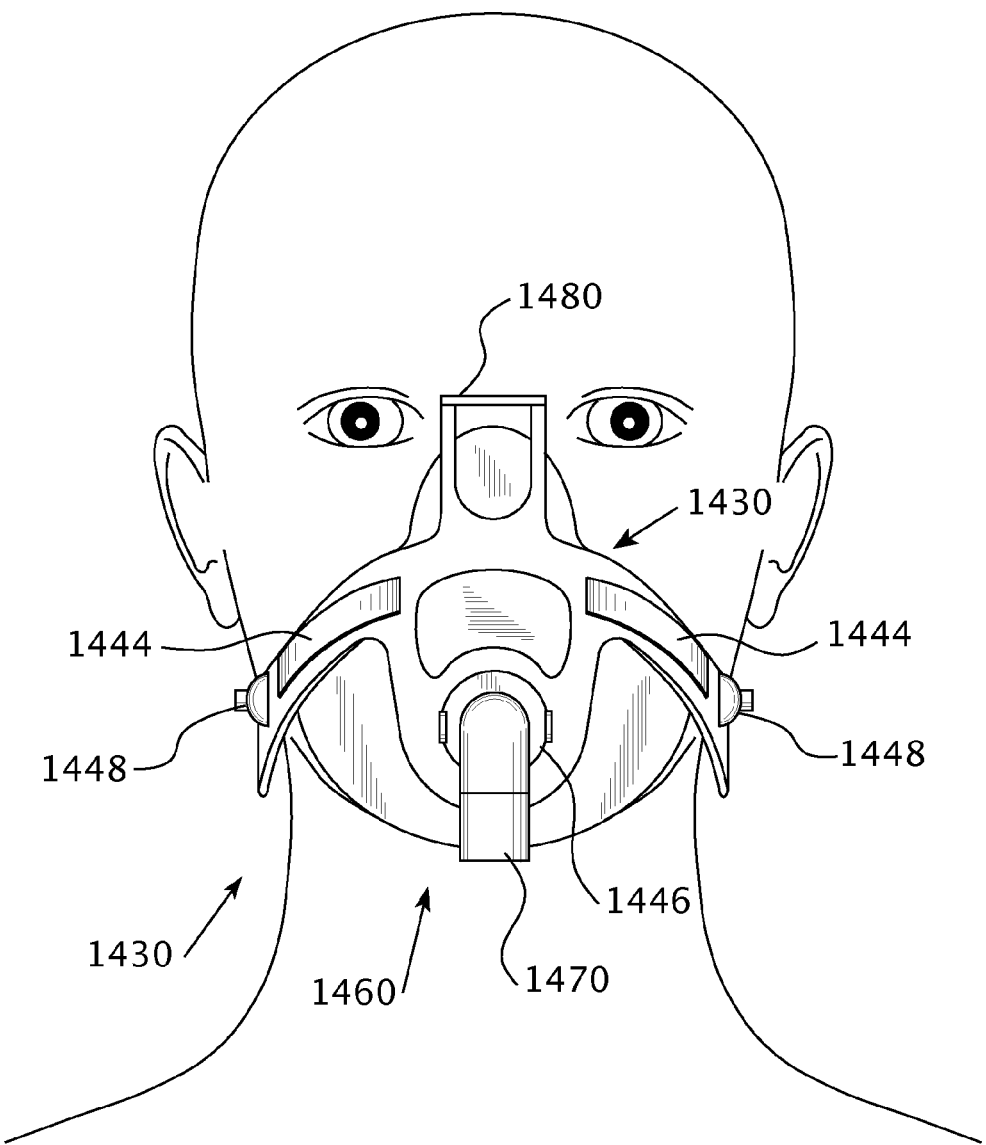

FIGS. 55-57 illustrate a fourteenth embodiment of a patient interface device 1430 according to the principles of the present invention. Patient interface device 1430 includes a body portion 1440 and a patient interface portion 1460. Body portion 1440 includes a chin support 1442 (shown in dashed lines), a pair of arms 1444, and a circuit coupling portion 1446 that is coupled to the pair of arms. Attachment structures 1445 are provided on arms 1444 to coupled the chin support to the body portion. In addition, attachment elements 1448 are also provided on arms 1444 to couple a headgear strap (not shown) to the body member.

Patient interface device 1430 is generally similar to patient interface devices 1230 and 1330 of FIGS. 48-54 in that it too is a full-face type of nasal interface, covering both the nares and mouth. This embodiment illustrates ever further possible variations that can be provided in the features that make up the patient interface device. A patient circuit coupling 1470 is coupled to circuit coupling portion 1446 so that a flow of gas can be communicated between a patient circuit (not shown) and the interior of patient interface portion 1460. In the illustrated exemplary embodiment, patient circuit coupling 1470 is an elbow coupling that rotatably and releasably attaches to circuit coupling portion 1446.

In this embodiment, body portion 1430 includes a forehead support portion 1480 that extends to the forehead area of the user. Forehead support can have any one of a variety of different features, sizes, configurations, including, for example, making the forehead support adjustable relative to the remainder of the body member. U.S. Pat. No. 7,069,932, the contents of which are incorporated herein by reference, teaches examples of adjustable forehead support assemblies suitable for use in the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device comprising:
   (a) a body portion comprising:
      (1) a pair of arms,
      (2) a chin support, wherein a first end portion of each arm in the pair of arms is coupled to an opposite end of the chin support, and wherein the chin support is adapted to be disposed under the mandible of a user responsive to the patient interface device being donned by such a user, and
      (3) a circuit portion operatively coupled to a second end portion of each arm in the pair of arms, the circuit portion including a first support and a second support;

(b) a first nasal cushion adapted to be coupled the first support; and (c) a second nasal cushion adapted to be coupled the second support, wherein the first and the second nasal cushions are independently removable from the respect first or second support.

2. The patient interface device of claim 1, wherein the circuit portion as a generally Y-shape, and wherein the first nasal cushion and the second nasal cushion are disposed at respective ends of the Y-shape.

3. The patient interface device of claim 1, wherein the first support and the first nasal cushion define a first ball and socket connection, and wherein the second support and the second nasal define a second ball and socket connection.

4. The patient interface device of claim 1, wherein the body portion includes at least one headgear attachment defined on each arm in the pair of arms.

5. The patient interface device of claim 1, wherein the chin support comprises a flexible strap.

6. The patient interface device of claim 1, wherein the pair of arms are (a) integral with the circuit portion, or (b) selectively attachable to the circuit portion.

7. The patient interface device of claim 1, further comprising an oral member adapted to (a) cover a mouth of such a user, or (b) seal an oral passage of such user.

8. The patient interface device of claim 1, further comprising a mouthpiece coupled to the body portion, the mouthpiece having an oral path enabling the circuit portion to communicate with an oral cavity of such a user responsive to the patient interface device being donned by such a user.

9. A patient interface device comprising:
(a) a body portion comprising:
(1) a pair of arms,
(2) a chin support, wherein a first end portion of each arm in the pair of arms is coupled to an opposite end of the chin support, and wherein the chin support is adapted to be disposed under the mandible of a user responsive to the patient interface device being donned by such a user, and
(3) a circuit coupling portion operatively coupled to a second end portion of each arm in the pair of arms;
(b) a conduit member adapted to be selectively coupled to the circuit coupling portion, the conduit member including a patient interface portion adapted to provide a sealed interface with nasal passages of a user.

10. The patient interface device of claim 9, wherein the circuit coupling portion includes a channel adapted to receive a portion of the conduit member.

11. The patient interface device of claim 10, wherein the circuit coupling portion and the conduit member each have a generally Y-shape, and the patient interface portion includes a first nasal cushion and a second nasal cushion disposed at respective ends of the Y-shape of the conduit member.

12. The patient interface device of claim 9, wherein the patient interface includes:
a first support;
a second support;
a first nasal cushion adapted to be coupled the first support; and
a second nasal cushion adapted to be coupled the second support, wherein the first and the second nasal cushions are independently removable from the respect first or second support.

13. The patient interface device of claim 12, wherein the first support and the first nasal cushion define a first ball and socket connection, and wherein the second support and the second nasal define a second ball and socket connection.

14. The patient interface device of claim 9, wherein the body portion includes at least one headgear attachment defined on each arm in the pair of arms.

15. The patient interface device of claim 9, wherein the chin support comprises a flexible strap.

16. The patient interface device of claim 9, wherein the pair of arms are (a) integral with the circuit portion, or (b) selectively attachable to the circuit portion.

17. The patient interface device of claim 9, further comprising an oral member adapted to (a) cover a mouth of such a user, or (b) seal an oral passage of such user.

18. The patient interface device of claim 9, further comprising a mouthpiece coupled to the body portion, the mouthpiece having an oral path enabling the circuit portion to communicate with an oral cavity of such a user responsive to the patient interface device being donned by such a user.

* * * * *